United States Patent
Kang et al.

(10) Patent No.: US 6,268,131 B1
(45) Date of Patent: Jul. 31, 2001

(54) MASS SPECTROMETRIC METHODS FOR SEQUENCING NUCLEIC ACIDS

(75) Inventors: Changwon Kang, Taejon; Young-Soo Kwon, Kwangju; Young Tae Kim, Seoul, all of (KR); Hubert Köster, La Jolla, CA (US); Daniel P. Little, Patton, PA (US); Maryanne J. Little, Groton, MA (US), now by change of name from Maryanne J. O'Donnell; Guobing Xiang, San Diego, CA (US); David M. Lough, Eyemouth (GB); Charles Cantor, Boston, MA (US)

(73) Assignee: Sequenom, Inc., San Diego, CA (US)

( * ) Notice: Subject to any disclaimer, the term of this patent is extended or adjusted under 35 U.S.C. 154(b) by 0 days.

(21) Appl. No.: 08/990,851

(22) Filed: Dec. 15, 1997

(51) Int. Cl.$^7$ .................................................... C12Q 1/68

(52) U.S. Cl. ............................................. 435/6; 435/91.2

(58) Field of Search .................... 435/6, 91.1, 91.2, 435/91.3, 518, 528; 436/518, 528; 536/23.1

(56) References Cited

U.S. PATENT DOCUMENTS

| | | | |
|---|---|---|---|
| 3,776,700 | 12/1973 | Gallant | 422/65 |
| 3,807,235 | 4/1974 | Lefkovitz | 73/863.32 |
| 4,139,346 | 2/1979 | Rabbani | 422/56 |
| 4,442,354 | 4/1984 | Hurst et al. | 250/281 |
| 4,461,328 | 7/1984 | Kenney | 422/100 |
| 4,554,839 | 11/1985 | Hewett et al. | 73/864.16 |
| 4,582,789 | 4/1986 | Sheldon, III et al. | 435/6 |
| 4,683,195 | 7/1987 | Mulis et al. | 435/6 |
| 4,725,677 | 2/1988 | Köster et al. | 536/27 |
| 4,729,947 | 3/1988 | Middendorf et al. | 435/6 |
| 4,731,335 | 3/1988 | Brigati | 436/180 |
| 4,757,141 | 7/1988 | Fung et al. | 536/27 |
| 4,779,467 | 10/1988 | Rainin et al. | 73/863.32 |
| 4,797,355 | 1/1989 | Stabinsky | 435/6 |
| 4,798,706 | 1/1989 | Brigati | 422/102 |
| 4,806,546 | 2/1989 | Carrico et al. | 536/27 |
| 4,843,003 | 6/1989 | Henikoff et al. | 435/91 |
| 4,855,225 | 8/1989 | Fung et al. | 435/6 |
| 4,877,745 | 10/1989 | Hayes et al. | 435/166 |

(List continued on next page.)

FOREIGN PATENT DOCUMENTS

| | | |
|---|---|---|
| 0268237 | 5/1988 | (EP) . |
| 0339781 | 11/1989 | (EP) . |
| 0359225 | 3/1990 | (EP) . |

(List continued on next page.)

OTHER PUBLICATIONS

Kwon et al., Bipartite Molecular Structure of Intrinsic, RNA Hairpin–independent Termination Signal for Phage RNA Polymerases, *J. of Biological Chemistry* 274(41):29149–55 (1999).

International Search Report, PCT/US 98/26718, Dec. 15, 1998.

Green and Toms, "The dissociation of avidin–biotin complexes by guanidinium chloride", *Biochem J.* 130:707–711 (1972).

(List continued on next page.)

*Primary Examiner*—John S. Brusca
*Assistant Examiner*—Jeffrey S. Lundgren
(74) *Attorney, Agent, or Firm*—Stephanie L. Seidman; Heller Ehrman White & McAuliffe LLP

(57) ABSTRACT

A mass spectrometric method for sequencing nucleic acids using RNA polymerases, including DNA-dependent and RNA-dependent RNA polymerases, is provided. The methods use a modified Sanger sequencing strategy in which RNA polymerase is used to generate a set of nested RNA transcripts obtained by base-specific chain termination. These are analyzed by mass spectrometry. A method of identifying transcriptional terminator sequences or attenuator sequences is also provided.

34 Claims, 17 Drawing Sheets

U.S. PATENT DOCUMENTS

| | | | |
|---|---|---|---|
| 4,882,127 | 11/1989 | Rosenthal et al. | 422/50 |
| 4,902,481 | 2/1990 | Clark et al. | 422/101 |
| 4,925,629 | 5/1990 | Schramm | 422/82.05 |
| 4,948,442 | 8/1990 | Manns | 156/73.1 |
| 4,948,882 | 8/1990 | Ruth | 536/27 |
| 4,952,518 | 8/1990 | Johnson et al. | 436/518 |
| 4,994,373 | 2/1991 | Stavrianopoulos et al. | 435/6 |
| 5,000,921 | 3/1991 | Hanaway et al. | 422/100 |
| 5,002,868 | 3/1991 | Jacobson et al. | 435/6 |
| 5,003,059 | 3/1991 | Brennan | 536/27 |
| 5,023,187 | 6/1991 | Koebler et al. | 436/180 |
| 5,045,694 | 9/1991 | Beavis et al. | 250/287 |
| 5,047,215 | 9/1991 | Manns | 422/101 |
| 5,064,754 | 11/1991 | Mills | 435/6 |
| 5,077,210 | 12/1991 | Eigler et al. | 435/176 |
| 5,082,935 | 1/1992 | Cruickshank | 536/27 |
| 5,108,703 | 4/1992 | Pfost et al. | 422/65 |
| 5,118,605 | 6/1992 | Urdea | 435/6 |
| 5,118,937 | 6/1992 | Hillenkamp | 250/282 |
| 5,135,870 | 8/1992 | Williams et al. | 436/86 |
| 5,149,625 | 9/1992 | Church et al. | 435/6 |
| 5,210,412 | 5/1993 | Levis et al. | 250/288 |
| 5,221,518 | 6/1993 | Mills | 422/62 |
| 5,237,016 | 8/1993 | Ghosh et al. | 525/329.4 |
| 5,242,974 | 9/1993 | Holmes | 525/54.11 |
| 5,262,128 | 11/1993 | Leighton et al. | 422/100 |
| 5,283,342 | 2/1994 | Gustavson et al. | 548/304.1 |
| 5,288,644 | 2/1994 | Beavis et al. | 436/94 |
| 5,312,233 | 5/1994 | Tanny et al. | 417/316 |
| 5,338,688 | 8/1994 | Deeg et al. | 436/180 |
| 5,380,833 | 1/1995 | Urdea | 536/22.1 |
| 5,381,008 | 1/1995 | Tanner et al. | 250/288 |
| 5,382,793 | 1/1995 | Weinberger et al. | 250/288 |
| 5,410,068 | 4/1995 | Coull et al. | 548/545 |
| 5,430,136 | 7/1995 | Urdea et al. | 536/243 |
| 5,436,327 | 7/1995 | Southern et al. | 536/25.34 |
| 5,439,649 | 8/1995 | Tseung et al. | 422/99 |
| 5,457,041 | 10/1995 | Ginaven et al. | 435/172.1 |
| 5,474,895 | 12/1995 | Ishii et al. | 435/6 |
| 5,478,893 | 12/1995 | Ghosh et al. | 525/329.4 |
| 5,484,701 | 1/1996 | Cocuzza et al. | 435/6 |
| 5,503,980 | 4/1996 | Cantor | 435/6 |
| 5,506,348 | 4/1996 | Pieles | 536/23.1 |
| 5,512,295 | 4/1996 | Kornberg et al. | 424/450 |
| 5,512,439 | 4/1996 | Hornes et al. | 435/6 |
| 5,514,548 | 5/1996 | Krebber et al. | 435/6 |
| 5,527,675 | 6/1996 | Coull et al. | 435/6 |
| 5,541,313 | 7/1996 | Ruth | 536/24.3 |
| 5,545,539 | 8/1996 | Miller | 435/91.2 |
| 5,547,835 | 8/1996 | Koster | 435/6 |
| 5,571,669 | 11/1996 | Lu et al. | 435/6 |
| 5,580,733 | 12/1996 | Levis et al. | 435/6 |
| 5,589,136 | 12/1996 | Northrup et al. | 422/102 |
| 5,599,500 | 2/1997 | Jones | 422/62 |
| 5,601,982 | 2/1997 | Sargent et al. | 435/6 |
| 5,604,099 | 2/1997 | Erlich et al. | 435/6 |
| 5,605,662 | 2/1997 | Heller | 422/68.1 |
| 5,605,798 | 2/1997 | Köster | 435/6 |
| 5,622,824 | 4/1997 | Köster et al. | 435/6 |
| 5,624,711 | 4/1997 | Sundberg et al. | 427/261 |
| 5,631,134 | 5/1997 | Cantor | 435/6 |
| 5,641,959 | 6/1997 | Holle et al. | 250/287 |
| 5,643,798 | 7/1997 | Beavis et al. | 436/94 |
| 5,654,545 | 8/1997 | Holle et al. | 250/287 |
| 5,663,242 | 9/1997 | Ghosh et al. | 525/329.4 |
| 5,670,322 | 9/1997 | Eggers et al. | 435/6 |
| 5,670,353 | 9/1997 | Ahlquist et al. | 459/572 |
| 5,670,381 | 9/1997 | Jou et al. | 436/518 |
| 5,677,195 | 10/1997 | Winkler et al. | 436/518 |
| 5,691,141 | 11/1997 | Köster | 435/6 |
| 5,696,249 | 12/1997 | Gold et al. | 536/23.1 |
| 5,700,642 | 12/1997 | Monforte et al. | 435/6 |
| 5,716,825 | 2/1998 | Hancock et al. | 435/286.5 |
| 5,742,049 | 4/1998 | Holle et al. | 250/282 |
| 5,746,373 | 5/1998 | Sanada | 239/102.2 |
| 5,757,392 | 5/1998 | Zhang | 347/14 |
| 5,795,714 | 8/1998 | Cantor et al. | 435/6 |
| 5,807,522 | 9/1998 | Brown et al. | 422/50 |
| 5,830,655 | 11/1998 | Monforte et al. | 435/6 |
| 5,864,137 | 1/1999 | Becker et al. | 250/287 |

FOREIGN PATENT DOCUMENTS

| | | |
|---|---|---|
| 0396116 | 11/1990 | (EP) . |
| 0455905 | 11/1991 | (EP) . |
| 0456304 | 11/1991 | (EP) . |
| 0500506 | 8/1992 | (EP) . |
| 0701001 | 3/1996 | (EP) . |
| 0785278 | 7/1997 | (EP) . |
| 2017105 | 3/1979 | (GB) . |
| 8800201 | 1/1988 | (WO) . |
| 8903432 | 4/1989 | (WO) . |
| 8907149 | 8/1989 | (WO) . |
| 8909282 | 10/1989 | (WO) . |
| 8911270 | 11/1989 | (WO) . |
| 8912694 | 12/1989 | (WO) . |
| 9001564 | 2/1990 | (WO) . |
| 9003382 | 4/1990 | (WO) . |
| 9007582 | 7/1990 | (WO) . |
| 9014148 | 11/1990 | (WO) . |
| 9015883 | 12/1990 | (WO) . |
| 9105060 | 4/1991 | (WO) . |
| 9106678 | 5/1991 | (WO) . |
| 9111533 | 8/1991 | (WO) . |
| 9112341 | 8/1991 | (WO) . |
| 9202635 | 2/1992 | (WO) . |
| 9203575 | 3/1992 | (WO) . |
| 9207879 | 5/1992 | (WO) . |
| 9210092 | 6/1992 | (WO) . |
| 9213629 | 8/1992 | (WO) . |
| 9306925 | 4/1993 | (WO) . |
| 9309668 | 5/1993 | (WO) . |
| 9411530 | 5/1994 | (WO) . |
| 9411735 | 5/1994 | (WO) . |
| 9416101 | 7/1994 | (WO) . |
| 9421822 | 9/1994 | (WO) . |
| 9504524 | 2/1995 | (WO) . |
| 9513538 | 5/1995 | (WO) . |
| 9514108 | 5/1995 | (WO) . |
| 9531429 | 11/1995 | (WO) . |
| 9605323 | 2/1996 | (WO) . |
| 9637630 | 5/1996 | (WO) . |
| 9629431 | 9/1996 | (WO) . |
| 9632504 | 10/1996 | (WO) . |
| 9636731 | 11/1996 | (WO) . |
| 9708306 | 3/1997 | (WO) . |
| 9716699 | 5/1997 | (WO) . |
| 9733000 | 9/1997 | (WO) . |
| 9737041 | 10/1997 | (WO) . |
| 9742348 | 11/1997 | (WO) . |
| 9743617 | 11/1997 | (WO) . |
| 9812355 | 3/1998 | (WO) . |
| 9820166 | 5/1998 | (WO) . |

OTHER PUBLICATIONS

Green, Avidin, *Adv. Protein Chem.* 29:85–133 (1975).

Greene, *Protective Groups in Organic Synthesis,* 2nd Edition, Wiley & Sons (1991).

Gross J. et al., "Investigations of the metastable decay of DNA under ultraviolet matrix–assistd laser desorption/ionization conditions with post–source–decay analysis and hydrogen/deuterium exchange", *J Am Soc Mass Spectrom.* 9(9):866–78 (1998).

Gruić–Sovuji I. et al., "Detection of noncovalent tRNA.aminoacyl–tRNA synthease complexes by matrix–assisted laser desorption/ionization mass spectrometry", *J Biol Chem.* 272(51):32084–91 (1997).

Gruić–Sovulj I. et al., "Matrix–assisted laser desorption/ ionisation mass spectrometry of transfer ribonucleic acids isolated from yeast", *Nucleic Acids Res.* 25(9):1859–61 (1997).

Hager et al., "Use of mono Q high–resolution ion–exchange chromatography to obtain highly pure and active *Escherichia coli* RNA polymerase", *Biochemistry* 29:7890–7894 (1990).

Hahner S. et al., "Matrix–assisted laser desorption/ionization mass spectrometry (MALDI) of endonuclease digests of RNA", *Nucleic Acids Res.* 25(10):1957–64 (1997).

Haralambidis et al., "Preparation of base–modified nucleosides suitable for non–radioactive label attachment and their incorporation into synthetic oligodeoxyribonucleotides", *Nucleic Acids Res.* 15:4857–4876 (1987).

Hayashi et al., "Immobilization of thiol proteases onto porous poly(vinyl alcohol) beads", *Polymer Journal,* 25:5, 489–497 (1993).

Hazum et al., "A photocleavable protecting group for the thiol function of cysteine", *Pept., Proc. Eur. Pept. Symp., 16th,* Brunfeldt, K (Ed), pp. 105–110 (1981).

He et al., "Rapid mutagenesis and purification of phage RNA polymerases", *Protein Expr. Purif* 9:142–151 (1996).

Hermanson, *Bioconjugate Techniques,* Academic Press (1996).

Higgins et al., "Competitive oligonucleotide single–base extension combined with mass spectrometric detection for mutation screening", *Biotechniques* 23(4):710–4 (1997).

Higuchi et al., "A general method of in vitro preparation and mutagenesis of DNA fragments: Study of protein and DNA interactions", *Nucleic Acids Res.* 16:7351–7367 (1988).

Lagerstrom et al., "Capture PCR: Efficient amplification of DNA fragments adjacent to a known sequence in human and YAC DNA", *PCR Methods and Applications* Cold Spring Harbor Lab. Press 1:111–119 (1991).

Lamture et al., "Direct detection of nucleic acid hybridization on the surface of a charge coupled device", *Nucl. Acids Res.* 22:2121–2125 (1994).

Landegren et al., "DNA Diagnostics—Molecular techniques and automation", *Science* 242:229–237 (1988).

Lawrance et al., "Megabase–scale mapping of the HLA gene complex by pulsed field gel electrophoresis", *Science* 235(4797):1387–1390 (1987).

Leonard et al., "Crystal and molecular structure of r(CGC-GAAUUAGGG): an RNA duplex containing two G(anti).A(anti) base pairs", *Structure* 2(6):483–94 (1994).

Li et al., "High–Resolution MALDI Fourier Transform Mass Spectrometry of Oligonucleotides", *Anal Chem.* 68(13):2090–2096 (1996).

Li et al., "Analysis of single mammalian cell lysates by mass spectrometry", *J. Am. Chem. Soc.* 118:1662–1663 (1996).

Lim and Pene, "Optimal conditions for supercoil DNA sequencing with the *Escherichia coli* DNA polymerase I large fragment", *Gene Anal. Techn.* 5:32–39 (1988).

Lim, Janghoo et al., "DNA sequencing by base–specific abortion of the bacteriophase transcription", Biochemical Society of ROK Annual Fall Meeting, Abstracts p. 191, Taejon, Korea, 10.15–16 (1998).

Little et al., "Identification of apolipoprotein E polymorphisms using temperature cycled primer oligo base extension and mass spectrometry", *Eur J clin Chem Clin Biochem.* 35(7):545–548 (1997).

Little et al., "Mass spectrometry from miniaturized arrays for full comparative DNA analysis", *Nature Med* 3(12):1413–1416 (1997).

Little et al., "MALDI on a Chip: Analysis of Arrays of Low–Femtomole to Subfemtomole Quantities of Synthetic Oligonucleotides and DNA Diagnostic Products Dispensed by a Piezoelectric Pipet", *Anal chem* 69:4540–4546 (1997).

Little et al., "Verification of 50–to 100–mer DNA and RNA sequences with high–resolution mass spectrometry", *Proc. Natl Acad Sci USA* 92(6):2318–22 (1995).

Little et al., "Direct detection of synthetic and biologically generated double–stranded DNA by MALDI–TOF MS", *J. Mass Spec* 17:1–8 (1997).

*Molecular Cloning: A laboratory manual,* 2nd ed., Ch. 11: Synthetic oligonucleotide probes, Sambrook, Cold Spring Harbor Laboratory Press New York, pp. 11.1–11.61 (1989).

Montforte et al., RNA folding during transcription by *Escherichia coli* RNA polymerase analyzed by RNA self–cleavage, *Biochemistry* 29:7882–7890 (1990).

Monteforte et al., Analysis of DNA adducts and mutation in transgenic mice exposed to benzo[a]pyrene, *Environmental Molec. Mutagenesis 21 Supp* 22:49 (1993).

Murray, "DNA sequencing by mass spectrometry", *J. Mass. Spect. 31*:1203–1215 (1996).

Nakamaye et al., "Direct sequencing of polymerase chain reaction amplified DNA fragments through the incorporation of deoxymucleoside $\alpha$–thiotriphosphates", *Nucleic Acids Res.* 16(21):9947–9959 (1988).

Nelson et al., "Volatlization of High Molecular Weight DNA by Pulsed Laser Ablation of Frozen Aqueous Solutions", *Science* 246:1585–1587 (1989).

Nelson et al., "Time–of–flight mass spectrometry of nucleic acids by laser ablation and ionization from a frozen aqueous matrix", *Rapid Communications in Mass Spectrometry* 4:348–351 (1990).

Newton et al., "The production of PCR products with 5' single–stranded tails using primers that incorporate novel phosphoramidite intermediates", *Nucl. Acids. Res.* 21:1155–1162 (1993).

Nikiforov and Rogers, "The use of 96–well polystyrene plates for DNA hybridization–based assays: An evaluation of different approaches to oligonucleotide immobilzation", *Anal. Biochem.* 227:201–209 (1995).

Nordhoff et al., "Ion stability of nucleic acids in infrared matrix–assisted laser desorption/ionization mass spectrometry", *Nuc Acids Res.* 21(15):3347–3357 (1993).

Nordoff et al., "Matrix–assisted laser desorption/ionization mass spectrometry of nucleic acids with wavelength in the ultraviolet and infrared", *Rapid Comm. Mass Spectrom.* 6:771–776 (1992).

O'Donnell et al., "High–Density, Covalent Attachment of DNA to Siliocn Wafers for Analysis by MALDI–TOF Mass Spectrometry", *Analytical Chemistry* 69(13):2438–2443 (1997).

O'Donnell et al., "MassArray as an Enabling Technology for the Industrial–Scale Analysis of DNA", *Genetic Engineering News 17*(21) (1997).

O'Donnell–Maloney et al., "Microfabrication and array technologies for DNA sequencing and diagnostics", *Genetic Analysis: Biomolecular Engineering 13*:151–157 (1996).

Olejnik et al, "Photocleavable biotin phosphoramidite for 5'–end labeling, affinity purification and phosphorylation of synthetic oligonucleotides", *Nucleic Acids Res. 24*:351–366 (1996).

*Oligonucleotides and Analogues: A Practical Approach,* Eckstein, edr., Oxford University Press Ch. 3, pp. 56–57, 137–139, 255–259 (1991).

*Oligonucleotides and Analogues, A Practical Approach,* F. Eckstein, editor, IRL Press Oxford, 1991.

Ornstein et al., "Sequencing DNA using $^{35}$S–labeling: A troubleshooting guide", *Biotechniques 3*:476–483 (1985).

Overberg et al., "Laser Desorption Mass Spectrometry. Part II Performance and Applications of Matrix–Assisted Laser Desorption/Ionization of Large Biomolecules", *Mass Spect in the Biolog Science: A Tutorial* 181–197 (1992).

Perrouault et al., "Sequence–specific artificial photo–induced endonucleases based on triple helix–forming oligonucleotides", *Nature 344* (6264):358–360 (1990).

Pieles et al., "Matrix–assisted laser desorption ionization time–of–flight mass spectrometry: a powerful tool for the mass and sequence analysis of natural and modified oligonucleotides", *Nucleic Acids Res. 21*(14):3191–3196 (1993).

Pierce Immuno Technology Catalog, p. 57 (1993).

Pierce Catalog, pp. T123–T154, 1994.

Pitulle et al, "Initiator oligonucleotides for the combination of chemical of enzymatic RNA synthesis", *Gene,* Elsevier Science Publishers B.V., 101–105 (1992).

Pon, et al., "Derivation of controlled pore glass beads to rsolid phase oligonucleotide synthesis", *BioTechniques,* 6:8, 770–775 (1988).

Prober et al., "A system for rapid DNA sequencing with fluorescent chain–terminating dideoxynucleotides", *Science 238*:336–341 (1987).

Raftery, et al., "Characterzation of a mutant recombination S100 protein using electrospray ionization mass spectrometry", *Rapid Comm. Mass Spec. 11*:405–409 (1997).

Rasmussen et al., "Covalent immobilization of DNA onto polystyrene microwells: The molecules are only bound at the 5'end", *Anal. Biochem. 198*:138–142 (1991).

Stahl et al., "Solid Phase DNA Sequencing using the Biotin–Avidin System", *Nucleic Acids Research,* vol. 16, No. 7, pp. 3025–3039 (1988).

Still et al., "Rapid chromatographic technique for preparative separations with moderate resolution", *J. Org. Chem. 43*(14):2923–2925 (1978).

Strezoska et al., "DNA sequencing by hybridization: 100 bases read by a non–gel–based method", *Proc. Natl. Acad. Sci. 88*:10089–10093 (1991).

Studier et al., "The genetics and physiology of bacteriophage T7$^1$", *Virology,* 39:562–574 (1969).

Swerdlow and Gesteland, "Capillary gel electrophoresis for rapid, high resolution DNA sequencing", *Nucleic Acids Res. 18*(6):1415–1419 (1990).

Tabor and Richardson, "DNA sequence analysis with a modified bacteriophage T7 DNA polymerase", *Proc. Natl. Acad. Sci. 84*:4767–4771 (1987).

Tang et al., "Detection of 500–nucleotide DNA by laser desorption mass spectrometry", *Rapid Commun. Mass Spectrom. 8*:727–730 (1994).

Tang et al., "Matrix–assisted laser desorption/ionization mass spectrometry of immobilized duplex DNA probes", *Nucleic Acids Research 23*:3126–3131 (1995).

Telesnitsky et al., "Terminator–distal sequences determine the in Vitro efficiency of the early terminators of bacteriophages T3 and T7", *Biochemistry* 28:5210–5218 (1989).

Thuong and Asseline, Oligonucleotides attached to intercalators, photoreactive and cleavage agents, *Oligonucleotides and Analogues: A Practical Approach,* Eckstein, edr., Oxford University Press Ch. 12, pp. 283–308 (1991).

Tolson et al., "Sequencing RNA by a combination of exonuclease digestion and uridine specific chemical cleavage using MALDI–TOF", *Nucleic Acids Res.* 26(2):446–51 (1998).

Tomer et al., "Coaxial Continuous Flow Fast Atom Bombardment for High–Molecular Weight Peptides: Comparison with Static Fast Atom Bombardment and electrospray Ionization", *Bio Mass Spect 20*:783–788 (1991).

Tong et al., "Solid–phase method for the purification of DNA sequencing reactions", *Anal. Chem.* 64:2672–2677, (1992).

Trainor, "DNA Sequencing: Automation, and the Human Genome", *Anal. Chem.* 62:418–426 (1990).

Tyagarajan et al., "RNA folding during transcription by T7 RNA polymerase analyzed using the self–cleaving transcript assay", *Biochemistry* 30:10920–10924 (1985).

Agrawal et al., "Efficient methods for attaching non–radioactive labels to the 5' ends of synthetic oligodeoxyribonucleotides", *Nucleic Acids Res. 14*:6227–6245 (1986).

Alderton et al., "Magnetic bead purification of M13 DNA sequencing templates", *Anal. Biochem. 201*:166–169 (1992).

Andersen, et al., "Electrospray ionization and matrix assisted laser desorption/ionization mass spectrometry: Powerful analytical tools in recombinant protein chemistry". *Nature Biotech. 14*:449–457 (1996).

Ansorge et al., "Automated DNA sequencing: ultrasensitive detection of fluorescent bands during electrophoresis", *Nucleic Acids Res. 15*:4593–4602 (1987).

Ardrey, Bob, "Electrospray mass spectrometry", *Spectroscopy Europe* 4(4):10–18 (1992).

Arlinghaus et al., "Applications of resonance ionization spectroscopy for semiconductor, environmental and biomedical analysis, and for DNA sequencing", SPIE, vol. 1435, *Opt. Methods Ultrasensitive Detect. Anal. Tech. Appl.* pp. 26–35 (1991).

Arshady, Reza, "Beaded polymer supports and gels: II. Physico–chemical criteria and functionalization", *Journal of Chromatography,* 586:199–219 (1991).

Arshady, Reza, "Beaded polymer supports and gels: I. Manufacturing techniques", *Journal of Chromatography,* 586:181–197 (1991).

Axelrod et al., "Transcription from bacteriophage T7 and SP6 RNA polymerase promoters in the presence of 3'–Deoxyribonucleoside 5'–triphosphate chain terminators", *Biochemistry* 245716–5723 (1985).

Bains, "DNA sequencing by mass spectrometry: Outline of a potential future application", *Chimicaoggi* 9:13–16 (1991).

Bains, "Setting a sequence to sequence a sequence", *Biotechnology 10*:757–758 (1992).

Bannwarth, "Solid–phase synthesis of oligodeoxynucleotides containing phosphoramidate internucleotide linkages and their specific chemical cleavage", *Helvetica Chimica Acta* 71:1517–1527 (1988).

Barr et al., "7–Deaza–2'–deoxyguanosine–5'–triphosphate: Enhanced resolution in M13 dideoxy sequencing", *Biotechinques* 4:428–432 (1986).

Barrell, "DNA sequencing: Present limitations and prospects for the future", *FASEB J.* 5: 40–45 (1991).

Barton et al., "Assays for poliovirus polymerase, $3D^{Pol}$, and authentic RNA replication in HeLa S10 extracts", *Methods Enzymol.* 275:35–57 (1996).

Bartra et al., "A fast procedure for the reduction of azidas and nitro compounds based on the reducing ability of $Sn(SR)_3$–species", *Tetrahedron* 46:587–594 (1990).

Batista–Viera et al., "A new method for reversible immobilization of thiol biomolecules bsed on solid–phase bound thiolsulfonate groups", *App. Biochem and Biotech,* 31:175–195 (1991).

Beaucage et al., "The synthesis of modified oligonucleotides by the phosphoramidite approach and their applications", *Tetrahedron* 49:6123–6194 (1993).

Beck et al., "Chemiluminescent detection of DNA: application of DNA sequencing and hybridization", *Nucleic Acids Res.* 17(13):5115–5123 (1989).

Beck and Köster, "Applications of dioxetane chemiluminescent probes to molecular biology", *Anal. Chem.* 62:2258–2270 (1990).

Berenkamp et al., "Infrared MALDI mass spectrometry of large nucleic acids", *Science* 281(5374):260–2 (1998).

Bevers S. et al., "Importance of specific adenosine N3–nitrogens for efficient cleavage by a hammerhead ribozyme", *Biochemistry* 35(20):6483–90 (1996).

Birnboim and Doly, "A rapid alkaline extraction procedure for screening recombinant plasmid DNA", *Nucl. Acids Res.* 7:1513–1523 (1979).

Braun et al., "Improved Analysis of Microsatellites Using Mass Spectrometry", *Genomics* 46:18–23 (1997).

Brennan et al., "New methods to sequence DNA by mass spectrometry", *SPIE*, vol. 1206, *New Technol. Cytom. Mol. Biol.* pp. 60–77 (1990).

Broude et al., "Enhanced DNA sequencing by hybridization", *Proc. Natl. Acad. Sci.* 91:3072–3076 (1994).

Brown et al., "A single–bead decode strategy using electrospray ionization mass spectrometry and a new photolabile linker: 3–Amino–3–(2–nitrophenyl)propionic acid", *Molec. Diversity* 1:4–12 (1995).

Brumbaugh et al., "Continuous, on–line DNA sequencing using oligodeoxynucleotide primers with multiple fluorophores", *Proc. Natl. Acad. Sci. USA* 85:5610–5614 (1988).

Burgers et al., "Diastereomers of 5'–O–Adenosyl 3'–O–Uridyl phosphorothioate: chemical synthesis and enzymatic properties", *Biochemistry* 18(4):592–596 (1979).

Burgess and Jendrisak, "A procedure for the rapid, large–scale purification of *Escherichia coli* DNA–dependent RNA polymerase involving polymin P precipitation and DNA–cellulose chromatography", *Biochemistry* 14:4634–4638 (1975).

Chan et al., "Dissection of the his leader pause site by base substitution reveals a multipartite signal that includes a pause RNA hairpin", *J. Mol. Biol.* 233:25–42 (1993).

Chen and Seeburg, "Supercoil sequencing: A fast and simple method for sequencing plasmid DNA", *DNA* 4(2):165–170 (1985).

Chrisey et al., "Covalent attachment of synthetic DNA to self–assembled monlayer films", *Nucl. Acids Res.* 24:3031–3039 (1996).

Chrisey et al., "Fabrication of patterned DNA surfaces", *Nucl. Acids. Res.* 24:3040–3047 (1996).

Chu et al., "Synthesis of an amplifiable reporter RNA for bioassays", *Nucleic Acids Res.* 14:5591–5603 (1986).

Church et al., "Multiplex DNA Sequencing", *Science* 240:185–188 (1988).

Connolly, B. A., "Oligonucleotides containing modified bases", *Oligonucleotides and Analogues, A Practical Approach*, Edited by F. Eckstein, Oxford University Press, Ch. 7, pp. 40–45, Chapter 7 pp. 155–183 (1991).

Covey et al., "The determination of protein, oligonucleotide and peptide molecular weights by ionspray mass spectrometry", *Rapid Communications in Mass Spectrometry* 2(11): 249–256 (1988).

Crain, "Mass spectrometric techniques in nucleic acid research", *Mass Spectr. Rev.* 9:505–554 (1990).

d'Aubenton Carafa et al., "Prediction of Rho–independent *Escherichia coli* transcription terminators", *J. Mol. Biol.* 216:835–858 (1990).

Damha, Masad J. et al., "An Improved Procedure for Derivatization of Controlled–Pore Glass Beads for Solid–Phase Oligonucleotide Synthesis", *Nucleic Acids Research* vol. 18, No. 13 (1990), pp.3813–3821.

Das et al., "Expression, purification, and characterization of rhabdovirus polymerase", *Methods Enzymol.* 275:99–122.

Deiman et al., "Efficient transcription of the tRNA–like structure of turnip yellow mosaic virus by a template–dependent and specific viral RNA polymerase obtained by a new procedure", *J. Virol Meth.* 64:181–195 (1997).

Drmanac, et al., "Sequencing of megabase plus DNA by hybridization: Theory of the method", *Genomics* 4:114–128 (1989).

Eckstein and Goody, "Synthesis and properties of diastereoisomers of adenosine 5'–(O–1–thiotriphosphate) and adenosine 5'–(O–2–thiotriphosphate)", *Biochemistry* 15(8):1685–1691 (1976).

Eckstein, F., "Phosphorothioate analogues of nucleotides", *Accounts Chem, Res.* 12:204–210 (1979).

Eckstein, Nucleoside phosphorothioates, *Ann. Rev. Biochem.* 54:367–402 (1985).

Edmonds et al., "Thermospray liquid chromatography–mass spectrometry of nucleosides and of enzymatic hydrolysates of nucleic acids", *Nucleic Acids Research* 13(22):8197–8206 (1985).

Eggers et al., "A microchip for quantitative detection of molecules utilizing luminescent and radioisotope reporter groups", *BioTechniques* 17:516–524 (1994).

Eoyang et al., *Procedures in Nucleic Acid Research,* Cantoni and Davies eds. V.2:829–839 (1971).

Eperon, I. C., "Rapid preparation of bacteriophage DNA for sequence analysis in sets of 96 clones, using filtration", *Anal. Biochem.* 156:406–412 (1986).

Fattom et al., "Comparative immunogenicity of conjugates composed of the *Staphylococcus aureus* type 8 capsular polysaccharide bound to carrierpic acid dihydrazide or N–succinimidyl–3–(2–pyridyldithio)propionate", *Infection Immunol.* 60:584–589, (1992).

Finn et al., "Ligands for insulin receptor isolation", *Biochemistry* 23:2554–2558, (1984).

Foster, *Organic Charge Transfer Complexes,* Academic Press (1969).

Frank and Köster, "DNA chain length markers and the influence of base composition on electrophoretic mobility of oligodeoxyribonucleotides in polyacrylamide–gels", *Nucl. Acids Res.* 6:2069–2087 (1979).

Fu et al., "Sequencing exons 5 to 8 of the p53 gene by MALDI–TOF mass spectrometry", *Nat Biotechnol* 16(4):381–4 (1998).

Fu et al., "Efficient preparation of short DNA sequence ladders potentially suitable for MALDI–TOF DNA sequencing", *Genet Anal.* 12(3–4):137–42 (1996).

Fu et al., "A DNA sequencing strategy that requires only five bases of known terminal sequencing for priming", *Proc. Natl. Acad. Sci.* 92:10162–10166 (1995).

Fujita et al., "Surprising lability of biotin–strepavidin bond during transcription of biotinylated DNA bound to paramagnetic beads", *BioTechniques* 14:608–617 (1993).

Ganem et al., "Detection of oligonucleotide duplex forms by ion–spray mass spectrometry", *Tetrahedron Letters* 34(9):1445–1448, (1993).

Ghosh and Musso, "Covalent attachment to solid supports", *Nucl. Acids Res.* 15:5353–5372 (1987).

Giacomoni, Purification and DNA–binding properties of RNA polymerase from *Bacillus subtilis, Eur. J. biochem.* 106:579–591 (1980).

Gildea et al., "A versatile acid–labile linker for modification of synthetic biomolecules", *Tetrahedron Letters* 31:7095–7398 (1990).

Goldmacher et al., "Photoactivation of toxin conjugates", *Bioconjugate Chem.* 3:104–107, (1992).

Green and Jorgenson et al., "Variable–wavelength on–column fluorescence detector for open–tubular zone electrophoresis", *J. Chromatography* 352:337–343 (1986).

Higuchi et al., "Kinetic PCR analysis: Real–time monitoring of DNA amplification reactions", *Bio/Technology* 11:1026–1030 (1993).

Hillenkamp et al., "Matrix Assisted UV_Laser Desorption/ionization: A New Approach to Mass Spectrometry of Large Biomolecules", *Bio Mass Spectr.,* Burlingame and McCloskey (eds.), pp. 49–61, Elsevier Science Publishers B.V., Amsterdaman (1989).

Hillenkamp and Ehring, "Laser desorption mass spectrometry Part 1: Basic mechanisms and techniques", *Mass Spectrometry in the Biological Sciences: A tutorial*, pp. 165–179 (1992).

Hobbs and Eckstein, "A general method for the synthesis of 2'–azido–2'–deoxy–and 2'–amino–2'–deoxyribofuranoxyl purines", *J. Org. Chem.* 42:714–719 (1976).

Horn and Urdea, "Forks and combs and DNA: the synthesis of branched oligodeoxyribonucleotides", *Nucleic Acids Res.* 17(17):6959–6967 (1989).

Kornes and Korsnes, "Magnetic DNA hybridization of oligonucleotide probes attached to superparamagnetic beads and their use in the isolation of Poly(A) mRNA from eukaryotic cells", *GATA* 7:145–150, (1990).

Hsiung N. et al., "A new simpler photoaffinity analogue of peptidyl tRNA", *Nucleic Acids Res.* 1(12):1753–62 (1974).

Hultman et al., "Direct solid phase sequencing of genomic and plasmid DNA using magnetic beads as solid support", *Nucl. Acids Res.* 17:4937–4946 (1989).

Huth–Fehre et al., "Matrix–assisted laser desorption mass spectrometry of oligodeoxythymidulic acids", *Rapid Communications in Mass Spectrometry* 6(3):209–213 (1992).

Hyman, "A new method of sequencing DNA", *Anal. Biochem.* 174:423–436 (1988).

Ikehara and Maruyama, "Studies of nucleosides and nucleotides. LXXIX. Purine cyclonucleosides. (37). The total synthesis of an antibiotic 2'–amino–2'–deoxyguanosine", *Chem. Pharm. Bull. Japan* 26:240–244 (1978).

Imazawa and Eckstein, "Facile synthesis of 2'–amino–2'–deoxyribofurnaosyl purines", *J. Org. Chem.* 44:2039–2041 (1979).

Innis et al., "DNA sequencing with *Thermus aquaticus* DNA polymerase and direct sequencing of polymerase chain reaction–amplified DNA", *Proc. Natl. Acad. Sci. USA* 85:9436–9440 (1988).

Ish–Horowicz and Burke, "Rapid and efficient cosmid clong", *Nucl. Acids Res.* 13:2989–2998, (1981).

Jacobson, et al., "Applications of mass spectrometry to DNA sequencing", *GATA* 8:223–229 (1991).

Jäschke, A. et al., "Synthesis and properties of oligodeoxyribonucleotide–polyethylene glycol conjugates", *Nucleic Acids Res.* 22(22):4810–7 (1994).

Jett et al., "High–Speed DNA Sequencing: An Approach Based Upon fluorescence Detection of Single Molecules", *J. Bio Strut & Dynam.* 7(2):301–09 (1989).

Jurinke C. et al., "Analysis of ligase chain reaction products via matrix–assisted laser desorption/ionization time–of–flight–mass spectrometry", *Anal Biochem.* 237(2):174–81 (1996).

Jurinke C. et al., "Application of nested PCR and mass spectrometry for DNA–based virus detection: HBV–DNA detected in the majority of isolated anti–HBc positive sera", *Genet Anal.* 14(3):97–102 (1998).

Jurinke C. et al., "Recovery of nucleic acids from immobilized biotin–streptavidin complexes using ammonium hydroxide and applications in MALDI–TOF mass spectrometry", *Anal. Chem.* 69(5):904–10 (1997).

Jurinke C. et al., "Detection of hepatitis B virus DNA in serum samples via nested PCR and MALDI–TOF mass spectrometry", *Genet Anal.* 13(3):67–71 (1996).

Kang, Changwon, "New technology for human genome project: Mass spectrometric analysis of genomic polymorphism", [Plenary Lecture] Endocinology Update, Program p. 1–2, 11.6–7 (1998).

Khrapko et al., "An oligonucleotide hybridization approach to DNA sequencing", *FEB* 256(1,2):118–122 (1989).

Khrapko et al., "A method for DNA sequencing by hybridization with oligonucleotide matrix", *J. DNA Sequencing and Mapping* 1:375–388 (1991).

Kieser, "Factors affecting the isolation of CCC DNA from *Streptomyces lividans* and *Escherichia coli*", *Plasmid* 12:19–36 (1984).

Kim, Young–tae "Transcription of nicked DNA templates", M.S. Thesis, KAIST, Korea (1998).

Kirpekar et al., "7–deaza purine bases offer a higher ion stability in the analysis of DNA by matrix–assisted laser desorption/ionization mass spectrometry" *Rapid Commun. Mass Spectrom.* 9:525–531 (1995).

Kirpekar et al., "DNA sequence analysis by MALDI mass spectrometry", *Nucleic Acids Res.* 26(11):2554–9 (1998).

Kirpekar F. "Matrix–assisted laser desorption/ionization mass spectrometry of enzymatically synthesized RNA up to 150 kDa", *Nucleic Acids Res.* 22(19):3866–70 (1994).

Koleske et al., "Purification of yeast RNA polymerase II holoenzymes", *Methods Enzymol.* 273:176–184 (1996).

Köster et al., "A strategy for rapid and efficient DNA sequencing by mass spectrometry", *Nature Bio* 14:1123–1128 (1996).

Köster et al., "N–acyl protecting groups for deoxynucleotides: A quantitative and comparative study", *Tetrahedron* 37:363–369 (1981).

Köster et al., "Well–defined insoluble primers for the enzymatic synthesis of oligo–and polynucleotides", *Hoppe Seylers Z. Physiol. Chem.* 359(11):1579–1589 (1978).

Köster et al., "Oligonucleotide synthesis and multiplex DNA sequencing using chemiluminescent detection", *Nucl. Acids Res. Symposium Series No.* 24:318–321, (1991).

Kozal et al., "Extensive polymorphisms observed in HIV–1 clade B protease gene using high–density oligonucleotide arrays", *Nature Medicine* 2(7):753–759 (1996).

Kramer et al., Evolution in vitro: Sequence and phenotype of a mutant RNA resistant to ethidium bromide, *J. Mol. Biol.* 89:719–736 (1977).

Kussmann, et al., "Matrix–assisted laser desorption/ionization mass spectrometry sample preparation techniques designed for various peptide and protein analytes", *J. Mass Spec.* 32:593–601 (1997).

Kwon, Young–Soo (1998), "Intrinsic transcription termination of bacteriophage RNA polymerases: Characterization of two types of termination signal", Ph.D. Thesis, KAIST, Korea (1998).

Labeit et al., "Laboratory methods: A new method of DNA sequencing using deoxynucleoside α–thiotriphosphates", *DNA* 5:173–177 (1986).

Liu et al., "Probing RegA/RNA interactions using electrospray ionization–fourier transform ion cyclotron resonance–mass spectrometry", *Anal Biochem* 262(1):67–76 (1998).

Lund et al., "Assessment of methods for covalent binding of nucleic acids to magnetic beads, Dynabeads$^{tm}$ and the characteristics of the bound nucleic acids in hybridization reactions", *Nucl. Acids Res.* 16:10861–10880 (1988).

Maldonado et al., "Purification of human RNA polymerase II and general transcription factors", *Methods Enzymol.* 274:72–100 (1996).

Manoharan et al., "A 2'–O–thiol tether in the ribose moiety of nucleic acids for conjugation chemistry", *Gene*, 149:147–156 (1994).

Marshall and Hodgson, "DNA chips: An array of possibilities", *Nature Biotechnology* 16:27–31 (1998).

Martin, "New technologies for large–genome sequencing", *Genome* 31:1073–1080 (1989).

Matteucci et al., "Synthesis of deoxyoligonucleotides on a polymer support", *J. A. Chem. Soc.* 103:3185–3191, 1981.

Matthews et al., "Analytical strategies for the use of DNA probes", *Analytical Biochemistry* 169:1–25 (1988).

Maxam and Gilbert, "Sequencing end–labeled DNA with base–specific chemical cleavages", *Methods in Enzymology* 65:499–560 (1980).

McCray and Trentham, "Properties and uses of photoreactive caged compounds", *Annu. Rev. Biophys. Biophys. Chem.* 18:239–270 (1989).

Milligan et al., "Oligoribonucleotide synthesis using T7 RNA polymerase and synthetic DNA templates", *Nucleic Acids Res.* 15(21):8738–8798 (1987).

Miyazaki, et al., "The first Japanese case of Hb Santa Ana, an unstable abnormal hemoglobin, identified rapidly by electrospray ionization mass spectrometry", *Internal Medicine* 36:365–370 (1997).

Mizusawa, Saeko et al., "Improvement of the dideoxy chain termination method of DNA sequencing by use of deoxy–7–deazaguanosine triphosphate in place of dGTP".

Moini et al., "A Moving Belt Device to Couple High–Performance Liquid Chromatography and Chemical Reaction Interface Mass Spectrometry", *Bio Mass Spect.* 20:308–312 (1991).

Reynolds et al., "Parameters affecting transcription termination by *Escherichia coli* RNA", *J. Mol. Biol.* 224:53–63 (1992).

Reynolds et al., "Parameters affecting transcription termination by *Escherichia coli* RNA Polymerase", *J. Mol. Biol.* 224:31–51 (1992).

Rink, "Solid–phase synthesis of protected peptide fragments using a trialkoxy–diphenyl–methlester resin", *Tetrahedron Lett.* 28:3787–3790 (1987).

Running and Urdea, "A procedure for productive coupling of synthetic oligonucleotides to polystyrene microtiter wells for hybridization capture", *Biotechniques* 8:276–277 (1990).

Ruppert et al., "A filtration method for plasmid isolation using microtiter filter plates", *Anal. Biochem.* 230:130–134 (1995).

Ruppert et al., "Preparation of plasmid DNA as Sequencing Templates in a Microtiter Plate Format", Paper presented, Cold Spring Harbor Laboratory.

Ruppert et al., "A rapid and high throughput method for plasmid isolations", Presented: Automation in Mapping and DNA Sequencing Conference, Aug. 31–Sep. 2, 1994.

Sadhukhan et al., "Chromatographic separation of DNA dependent RNA polymerases and molecular properties of RNA polymerase II from a Leishmania Spp", *Mol. Cell. Biochem.* 171:105–114 (1997).

Saha et al., "Diisopropylsilyl–linked oligonucleotide analogs: Solid phase synthesis and physicochemical properties", *J. Org. Chem.* 58:7827–7831 (1993).

Saiki et al., "Genetic analysis of amplified DNA with immobilized sequence–specific oligonucleotide probes", *Proc. Natl. Acad. Sci.* 86:6230–6234 (1989).

Sanger et al., "DNA sequencing with chain–terminating inhibitors", *Proc. Natl. Acad. Sci.* 74:5463–67 (1977).

Sasaki et al., "Introduction of an azide group into some uridine derivatives via 2',3'–benzoxonium and 2',3'–azidonium intermediates", *J. Org. Chem.* 41:3138–3143 (1976).

Schmidt et al., "Binding of rho Factor to *Escherichia coli* RNA polymerase mediated by nusA protein", *J. Mol. Biol.* 259:15000–15002 (1984).

Schneider and Chait, "Increased stability of nucleic acids containing 7–deaza–guanosine and 7–deaza–adenosine may enable rapid DNA sequencing by matrix–assisted laser desorption mass spectrometry", *Nucleic Acids Res.* 23(9):1570–1575 (1995).

Schram, Karl H., "Mass Spectrometry of Nucleic Acid Components", *Bio Appl of Mass Spect.* 34:203–287 (1990).

Seela et al., "98. 1,7–Dideaza–2',3'–dideoxyadenosine: Synthesis of Pyrrolo[2,3–b]pyridine 2',3'–dideoxyribofuranosides and participation of purine N(1) during HIV–1 reverse transcriptase inhibition", *Helevica Chimica Acta* 74:1048–1058 (1991).

Seela and Kehne, "Palindromic octs–and dodecanucleotides containing 2'–deoxytubercidin: Synthesis, hairpin formation, and recognition by the endodeoxyribonuclease EcoRI", *Biochemistry* 26:2232–2238 (1987).

Senter et al., "Novel photocleavable protein crosslinking reagents and their use in the preparation of antibody–toxin conjugates", *Photochem. Photobiol.* 42:231–237, (1985).

Sequenom Signs Agreement With Bruker–Franzen Analytik to Develop Mass Spectrometer for DNA Massaray Analysis, Press Release: Jan. 12, 1998, http://www.sequenom.com/pressrelease.htm.

Sequenom Advances the Industrial Genomics Revolution with the Launch of Its DNA MassArray™ Automated Process Line, Press Release: Sep. 28, 1998, http://www.sequenom.com/pressrelease.htm.

Sequenom Reports DNA MassArray™ Technology More Sensitive Than Electrophoretic Methods in Detecting Gene Mutations: Automated DNA Analysis System Can Speed Up Microsatellite Analyses, Press Release: Dec. 15, 1997, http://www.sequenom.com/pressrelease.htm.

Sequenom Uses DNA MassArray™ to Sequence Section of Human Cancer–Related p53 Gene, Press Release: Mar. 27, 1998, http://www.sequenom.com/pressrelease.htm.

Sequenom Reports On Use of Its DNA MassArray™ Technology to Analyze Genes Associated with Alzheimer's Disease adn Arteriosclerosis: Technology Has Applications in Drug Development, Press Release: Sep. 22, 1997, http:/www.sequenom.com/pressrelease.htm.

Shaler et al., "Analysis of enzymatic DNA sequencing reactions by matrix–assisted laser desorption/ionization time–of–flight mass spectrometry", *Rapid Commun Mass Spectrom* 9(10):942–947 (1995).

Shaler et al., "Effect of Impurities on the matrix–Assisted Laser Desorption Mass Spectra of Single–Stranded Oligodeoxynucleotides", *Anal. Chem.* 68:576–579 (1996).

Siegert et al., "Matrix–assisted laser desorption/ionization time–of–flight mass spectrometry for the detection of polymerase chain reaction products containing 7–deazapurine moieties", *Analytical Biochemistry* 243:55–65 (1996).

Singh et al., "Oligonucleotides, part 5 +: synthesis and fluorescence studies on DNA oligomers d(AT)$_5$ containing adenines covalently linked at C–8 with dansyl fluorophore", *Nucleic Acids Res.* 18(11):3339–3345 (1990).

Sinha et al., "Polymer support oligonucleotide synthesis XVIII: use of β–cyanoethyl–N,N–dialkylamino–/N–morpholino phosphoramidite of deoxynucleosides for the synthesis of DNA fragments simplifying deprotection and isolation of the final product", *Nucleic Acids Res.* 12:4539–4557 (1984).

Sinha et al., "β–cyanoethyl N,N–dialkylamino/N–morpholinomonochloro phosphoamidites, new phosphitylating agents facilitating ease of deprotection and work–up of synthesized oligonucleotides", *Tetrahedron Lett.* 24:5843–5846 (1983).

Siuzdak, Gary, "The emergence of mass spectrometry in biochemical research", *Proc. natl. Acad. Sci. USA* 91:11290–11297 (1994).

Slim et al., "Configurationally defined phosphorothioate–containing oligoribonucleotides in the study of the mechanism of cleavage of hammerhead ribozymes", *Nucleic Acids Res.* 19:1183–1188 (1991).

Smith, Cassandra L., "cDNA Fingerprinting of Breast Cancer Tumor Cells", Boston Univ., MA (1996).

Smith et al., Fluorescence detection in automated DNA sequence analysis, *Nature* 321:674–679 (1986).

Smith, R. D., "New Developments in Biochemical Mass Spectrometry: Electrospray Ionization", *Anal. Chem.* 62:882–899 (1990).

Smith, Richard D. et al., "Capillary zone electrophoresis–mass spectrometry using an electrospray ionization interface", *Anal. Chem.* 60:436–441 (1988).

Sowa and Ouchi, "The facile synthesis of 5'–nucleotides by the selective phosphorylation of a primary hydroxyl group of nucleosides with phosphoryl chloride", *Bull Chem. Soc. Japan* 48:2084 (1975).

Sproat et al., "The synthesis of protected 5'–amino–2', 5'–dideoxyribonucleoside–3'–O–phosphoramidites: applications of 5'–amino–oligodeoxyribonucleotides", *Nucleic Acids Res.* 15:6181–6196 (1987).

Sproat et al., "The synthesis of protected 5'–mercapto–2', 5'–dideoxynucleoside–3'–O–phosphoramidites; uses of 5'mercapto–oligodeoxynucleotides", *Nucleic Acids Res.* 15:4837–4848 (1987).

St. Clair A. et al., "Synthesis and triplex forming properties of an acyclic N7–glycosylated guanine nucleoside", *Nucleosides Nucleotides* 17(5):925–37 (1998).

Urdea et al., A comparison of non–radioisotopic hybridization assay methods using fluorescent, chemiluminescent and enzyme labeled synthetic oligodeoxyribonucleotide probes, *Nucleic Acids Res.* 16(11):4937–4957 (1998).

Valaskovic et al., "Attomole protein characterization by capillary electrophoresis–mass spectrometry", *Science* 273:1199–1202 (1996).

Valaskovic, et al., Attomole–sensitivity electrospray source for large–molecule mass spectrometry, *Anal. Chem.* 67:3802–3805 (1995).

van den Boom et al., "Combined amplification and sequencing in a single reaction using two DNA polymerases with differential incorporation rates for dideoxynucleotides", *J. Biochem Biophys Methods* 35(2):69–79 (1997).

Verheyden et al., Synthesis of some pyrimidine 2'–amino–2'–deoxynucleosides, *J. Org. Chem.* 36:250–254 (1971).

Vieria and Messing, The pUC plasmids, and M13mp7–derived system for insertion mutagenesis and sequencing with synthetic universal primers, *Gene* 19:259–268 (1982).

Wallace, "Ink–jet based fluid microdispensing in biochemical applications", *Laboratory Automation News* 1(5):6–9 (1996).

Wang, Solid phase synthesis of protected peptides via photolytic cleavage of the α–methylphenacyl ester anchoring linkage, *J. Org. Chem.* 41(20):3258–3261 (1976).

Wellhöner et al., Uptake and concentration of bioactive macromolecules by K562 cells via the t'ransferrin cycle utilizing an acid–labile transferrin conjugate, *J. Biol. Chem.* 256:4309–4314, (1991).

Williams, Time of flight mass spectrometry of DNA laser–ablated from frozen aqueous solutions: applications to the Human Genome Project, *Intl. J. Mass Spectrom. and Ion Processes* 131:335–344 (1994).

Wilson et al., "Stability of *Escherichia coli* transcription complexes near an intrinsic terminator", Institute of Molecular Biology and Department of Chemistry, University of Oregon, Eugene, OR 36–51 (1994).

Wolter et al., Negative Ion FAB mass spectrometric analysis of non–charged key intermediates in oligonucleotide synthesis: Rapid indentification of partially protected dinucleoside monophosphates, *Biomedical Environmental Mass Spectrometry* 14:111–116 (1987).

Wong, Conjugation of proteins to solid matrices, *Chemistry of Protein Conjugation and Cross–Linking* 12:295–317 (1993).

Wu et al., "Matrix–assisted Laser Desorption Time–of–flight Mass Spectrometry of Oligonucleotides Using 3–Hydroxypicolinic Acid as an Ultraviolet–sensitive Matrix", *Rapid Comm Mass Spec* 7:142–146 (1993).

Wu et al., "Allele–specific enzymatic amplification of β–globin genomic DNA for diagnosis of sickle cell anemia," *Proc. Natl. Acad. Sci. USA* 86:2757–2760 (1989).

Wu et al., "Time–of–Flight Mass Spectrometry of Underivatized Single–Stranded DNA Oligomers by Matrix–Assisted Laser Desorption", *Anal. Chem.* 66:1637–1645 (1994).

Yamashita et al. Electrospray ion source. Another variation on the free–jet theme, *J. Phys. Chem.* 88:4451–4459, (1984).

Yates, III, Mass spectrometry and the age of the proteome, *J. Mass Spec.* 33:1–19 (1998).

Yen et al., Synthesis of water–soluble copolymers containing photocleavable bonds, *Makromol. Chem.* 190:69–82 (1989).

Zhang et al., Single–base mutational analysis of cancer and genetic diseases using membrane bound modified oligonucleotides, *Nucl. Acids Res.* 19:3929–3933 (1991).

Zimmerman et al., Automated preparation and purification of M13 templates for DNA sequencing, *Meth. Mol. Cell. Biol.* 1:29–34 (1989).

Zuckermann et al., Efficient methods for attachment of thiol speciifc probes to the 3'–ends of synthetic oligodeoxyribonucleotides, *Nucleic Acids Research,* 15:13, 5305–5321 (1987).

| k1 6968 Da 170 RP | k2 6968 Da 100 RP | k3 6988 Da 90 RP | k4 6977 Da 100 RP | k5 6971 Da 170 RP | k6 6968 Da 110 RP | k7 6972 Da 160 RP | k8 6978 Da 110 RP | k9 6952 Da 250 RP | k10 6965 Da 300 RP |
|---|---|---|---|---|---|---|---|---|---|
| l1 6965 Da 130 RP | l2 6989 Da 140 RP | l3 6982 Da 210 RP | l4 6996 Da 50 RP | l5 6982 Da 160 RP | l6 6968 Da 180 RP | l7 6984 Da 130 RP | l8 6968 Da 200 RP | l9 6996 Da 80 RP | l10 6968 Da 100 RP |
| m1 6966 Da 190 RP | m2 6979 Da 120 RP | m3 6975 Da 120 RP | m4 6968 Da 190 RP | m5 6976 Da 110 RP | m6 6986 Da 120 RP | m7 6973 Da 160 RP | m8 6978 Da 160 RP | m9 6975 Da 230 RP | m10 6955 Da 250 RP |
| n1 6961 Da 340 RP | n2 6971 Da 180 RP | n3 6970 Da 150 RP | n4 6960 Da 300 RP | n5 6985 Da 120 RP | n6 6953 Da 210 RP | n7 6971 Da 140 RP | n8 6962 Da 160 RP | n9 6957 Da 150 RP | n10 6960 Da 160 RP |
| o1 6965 Da 140 RP | o2 6960 Da 230 RP | o3 6976 Da 200 RP | o4 6953 Da 250 RP | o5 6983 Da 110 RP | o6 6967 Da 250 RP | o7 6970 Da 150 RP | o8 6973 Da 70 RP | o9 6953 Da 140 RP | o10 6952 Da 140 RP |
| p1 6976 Da 140 RP | p2 6981 Da 90 RP | p3 6972 Da 180 RP | p4 6969 Da 90 RP | p5 6984 Da 130 RP | p6 6968 Da 100 RP | p7 6958 Da 290 RP | p8 6981 Da 100 RP | p9 6978 Da 110 RP | p10 6965 Da 150 RP |
| q1 6976 Da 170 RP | q2 6985 Da 100 RP | q3 6990 Da 120 RP | q4 6989 Da 90 RP | q5 6984 Da 90 RP | q6 6969 Da 170 RP | q7 6979 Da 70 RP | q8 6968 Da 140 RP | q9 6973 Da 120 RP | q10 6950 Da 120 RP |
| r1 6966 Da 130 RP | r2 6960 Da 150 RP | r3 6969 Da 100 RP | r4 6964 Da 180 RP | r5 6966 Da 130 RP | r6 6970 Da 110 RP | r7 6972 Da 90 RP | r8 6939 Da 130 RP | r9 6951 Da 230 RP | r10 6965 Da 200 RP |
| s1 6963 Da 130 RP | s2 6953 Da 210 RP | s3 6970 Da 120 RP | s4 6971 Da 170 RP | s5 6957 Da 130 RP | s6 6956 Da 160 RP | s7 6966 Da 140 RP | s8 6975 Da 120 RP | s9 6951 Da 230 RP | s10 6969 Da 120 RP |
| t1 6974 Da 90 RP | t2 6958 Da 160 RP | t3 6959 Da 120 RP | t4 6952 Da 100 RP | t5 6959 Da 110 RP | t6 6954 Da 100 RP | t7 6950 Da 160 RP | t8 6974 Da 140 RP | t9 6967 Da 150 RP | t10 6950 Da 230 RP |

LASER POWER = 41000 FOR ALL SPECTRA.
EACH SPECTRUM THE SUM OF 10-30 SINGLE SHOTS.

Start of Transcription ⇩          Nick +7 ⇩

MASS SPECTROMETRIC METHODS FOR SEQUENCING NUCLEIC ACIDS

BACKGROUND OF THE INVENTION

Methods of sequencing DNA are typically performed by either the chemical degradation method of Maxam and Gilbert (*Methods in Enzymol.* 65:499–560 (1980)) or the enzymatic dideoxynucleotide termination method of Sanger et al. (*Proc. Natl. Acad. Sci. U.S.A.* 74:5463–67 (1977)). In the chemical method, base specific modifications result in a base specific cleavage of the radioactive or fluorescently labeled DNA fragment. With the four separate base specific cleavage reactions, four sets of nested fragments are produced which are separated according to length by polyacrylamide gel electrophoresis (PAGE). After autoradiography, the sequence can be read directly since each band (fragment) in the gel originates from a base specific cleavage event. Thus, the fragment lengths in the four "ladders" directly translate into a specific position in the DNA sequence.

In the enzymatic chain termination method, the four base specific sets of DNA fragments are formed by starting with a primer/template system elongating the primer into the unknown DNA sequence area and thereby copying the template and synthesizing a complementary strand using DNA polymerases, such as Klenow fragment of *E. coli* DNA polymerase I, a DNA polymerase from *Thermus aquaticus*, Taq DNA polymerase, or a modified T7 DNA polymerase, Sequenase (e.g., Tabor et al., (1987) *Proc. Natl. Acad. Sci. U.S.A.* 84:4767–4771), in the presence of chain-terminating reagents. Here, the chain-terminating event is achieved by incorporating into the four separate reaction mixtures in addition to the four normal deoxynucleoside triphosphates, dATP, dGTP, dTTP and dCTP, only one of the chain-terminating dideoxynucleoside triphosphates, ddATP, ddGTP, ddTTP or ddCTP, respectively, in a limiting small concentration. The four sets of resulting fragments produce, after electrophoresis, four base specific ladders from which the DNA sequence can be determined. Undesirably, most methods for sequencing DNA require the use of polyacrylamide gel electrophoresis (i.e., PAGE) that can result in sequencing artifacts or require detectable labels, such as radioisotopes, enzymes, or fluorescent or chemiluminescent moieties.

Using DNA sequencing methodologies, the entire sequence of the human genome will be determined. The knowledge of the complete sequence of the human genome DNA will certainly help to understand, to diagnose, to prevent and to treat human diseases. To be able to tackle successfully the determination of the approximately 3 billion base pairs of the human genome in a reasonable time frame and in an economical way, rapid, reliable, sensitive and inexpensive methods needed to be and still need to be developed.

Therefore it is an object herein to provide additional methods for sequencing. In particular, it is an object herein to provide mass spectrometric methods of sequencing nucleic acids using RNA polymerase. It is a further object herein to provide methods of sequencing nucleic acids in an array format using RNA polymerase in which nucleic acid probes are immobilized to supports at high densities to facilitate mass spectrometric detection. It is also an object herein to provide methods for identifying transcriptional terminator sequences using mass spectrometric methods.

SUMMARY OF THE INVENTION

Improved methods for sequencing nucleic acids is provided. In particular, a mass spectrometric method for sequencing nucleic acids using RNA polymerases, including DNA-dependent and RNA-dependent RNA polymerases, is provided. The methods utilize a modified Sanger sequencing strategy in which RNA polymerase is used to generate a set of nested RNA transcripts obtained by base-specific chain termination. These are analyzed by mass spectrometry.

In certain embodiments, a double stranded nucleic acid molecule encoding a promoter sequence is isolated from a natural source (e.g., bacteria, viruses, bacteriophages, plants or eukaryotic organisms) or assembled from synthetic sequences and is engineered using recombinant DNA means to contain a single stranded region of at least a 5 nucleotides at the 3'-end of the coding strand. This single stranded region is designed such that it is complementary to a region of the nucleic acid to be sequenced or to a common overlapping sequence (e.g., a restriction endonuclease site). In preferred embodiments, the promoter-containing nucleic acid is covalently coupled via the 3'-end of the noncoding strand or 5'-end of the coding strand to a solid support and, more preferably, is a 5'- or 3'-thiolated DNA linked at high densities to a aminosilane-treated solid support. The linkage may be in the absence or presence of a linker group and is preferably arranged in an array format.

The nucleic acid to be sequenced containing at least a partially single stranded 3'-end is hybridized to the complementary sequences of the promoter-containing DNA. The nucleic acid to be sequenced may be single stranded or double stranded. The hybridization of the two nucleic acid molecules introduces one or more "nicks" in the hybrid at the junction(s) of the adjacent nucleic acid molecules. In certain embodiments, nicks in the coding or non-coding strand, preferably the coding strand, are ligated by the addition of an appropriate nucleic acid ligase prior to initiating transcription (i.e., DNA or RNA ligase).

Transcription is initiated from the promoter by the addition of the appropriate RNA polymerase in the presence of ribonucleoside triphosphates and a selected base-specific chain terminating 3'-deoxyribonucleoside triphosphate. In preferred embodiments, the transcription mixture also contains inosine 5'-triphosphate to reduce the secondary structure of the RNA product and may further contain modified ribonucleoside triphosphates, such as 4-thio uridine 5'triphosphate (UTP), 5-bromo UTP or 5'-iodo CTP to increase the fidelity of termination and turnover of the RNA polymerase enzyme thereby increasing the amount of RNA transcript available for analysis.

The resulting RNA transcripts are analyzed by mass spectrometry. In preferred embodiments, the sample further contains a matrix material and is analyzed by matrix-assisted laser desorption/ionization mass spectrometry (MALDI) and preferably further uses time-of-flight (TOF) analysis. The sequence of the nucleic acid is obtained by aligning the observed mass of the chain-terminated RNA transcripts obtained from sequencing reactions containing each of the four chain-terminating bases.

In other embodiments, the method of sequencing may be used for diagnostic applications to determine the presence of genetic alterations in a known target nucleic acid. For example, a region of the target nucleic acid is amplified and the nucleic acid strand corresponding to the noncoding strand is isolated. The nucleic acid probe containing the promoter may be isolated from a natural source or assembled synthetically by hybridizing two complementary oligonucleotides to form a promoter sequence. A single stranded region of at least 5 nucleotides that is complementary to a region of the nucleic acid to be sequenced or to a common sequence is introduced by recombinant means at the 3'-end of the coding strand. In preferred embodiments, the promoter-containing nucleic acid is covalently coupled via the 3'-end of the noncoding strand or 5'-end of the coding strand to a solid support and, more preferably, is a 5'- or 3'-thiolated DNA linked at high densities to a aminosilane-treated solid support. The linkage may be in the absence or presence of a linker group and is preferably arranged in an array format.

A single stranded 3' overhang of the nucleic acid to be sequenced, in single stranded or double stranded form, is hybridized to the complementary sequences of the noncoding strand and, in some embodiments, the nick(s) between one or more nucleic acid strands is/are ligated prior to transcription. Transcription is initiated using the appropriate RNA polymerase in the presence of ribonucleoside triphosphates and a selected base-specific chain terminating 3'-deoxyribonucleoside triphosphate. In preferred embodiments, the transcription mixture may also contain inosine 5'-triphosphate andlor one or more modified ribonucleoside triphosphates to facilitate analysis of the RNA transcripts. The RNA transcripts are analyzed by mass spectrometry, preferably using MALDI-TOF.

When used in array formats, a panel of promoter-containing nucleic acid probes may be constructed such that the single stranded complementary regions of the target nucleic acid may be permuted along the entire sequence, e.g., the coding sequence of a gene, allowing for the determination of the nucleic acid sequence of the entire gene during a single reaction sequence.

Methods of identifying transcriptional terminator and attenuator sequences are also provided. By modifying the standard transcription conditions described herein, transcriptional terminator sequences, e.g., rho-dependent and rho-independent terminators, may be identified using mass spectrometric methods. In practicing the methods, a single stranded region of the 3'-end of the nucleic acid to be sequenced is hybridized to a complementary sequence at the 3'-end of the coding strand a promoter-containing nucleic acid probe. In preferred embodiments, the promoter-containing nucleic acid is covalently coupled via the 5'-end of the noncoding strand or 3'-end of the coding strand to a solid support and, more preferably, is a 5'- or 3'-thiolated DNA linked at high densities to a aminosilane-treated solid support. The linkage may be in the absence or presence of a linker group and is preferably arranged in an array format.

Transcription is initiated in the absence or presence of modified RNA triphosphate analogs that increase the efficiency of RNA polymerase termination at such terminator sequences, such as 4-thio UTP, 5-bromo UTP or 5'-iodo CTP. In certain embodiments, nicks in one or more strand may be ligated by the addition of an appropriate nucleic acid ligase prior to initiating transcription (i.e., adding a DNA or RNA ligase). The mass of the terminated RNA transcripts is determined by mass spectrometry. The observed mass is indicative of the location of the terminator-dependent arrest of transcription and by comparing the alignment of the sequence immediately preceding the site of transcriptional termination from distinct genomic locations, terminator and attenuator sequences may be identified for different RNA polymerases.

The above and further features and advantages of the instant invention will become clearer from the following Figures, Detailed Description and claims.

BRIEF DESCRIPTION OF THE DRAWINGS

FIG. 12 depicts molecular weights determined for the sample material having spectra identified in FIG. 11.

FIG. 13 is a schematic of a 4×4 (16-location) DNA array on the surface of a silicon wafer with the thiol-containing oligonucleotide molecules denoted "Oligomer 1", (5'-CTGGATGCGTCGGATCATCTTTTTT-(S)-3'; SEQ ID NO: 5), Oligomer 2 (5'-(S)-CCTCTTGGGAAcTGTGTAGTATT-3'; SEQ ID NO: 6) and "Oligomer 3" (SEQ ID NO: 1; a free thiol derivative "TCUC" oligonucleotide of EXAMPLE 1) covalently bound to 16 locations on the surface of the silicon wafer essentially as described in EXAMPLE 2.

FIG. 14 is a schematic of the hybridization of specific oligonucleotides to each of the 16 locations of the DNA hybridization array of FIG. 13 with the Oligomer 1 complementary oligonucleotide (5'-GATGATCCGACGCATCAGAATGT-3'; SEQ ID NO: 7) bound to Oligomer 1, the Oligomer 2 complementary oligonucleotide (5'-AATACTACACAG-3'; SEQ ID NO: 8) bound to Oligomer 2 and the Oligomer 3 complementary oligonucleotide (5'-CCGGGTACCGAGCTCGAATTC-3'; SEQ ID NO: 2) bound to Oligomer 3.

FIG. 17 shows the nucleotide sequence of a DNA molecule (SEQ ID No: 10) assembled by hybridizing a 55-mer oligonucleotide to a complementary 25-mer oligonucleotide (SEQ ID No: 11) and a complementary 30-mer oligonucleotide ISEQ ID No: 12). The resulting double stranded DNA encodes a SP6 promoter (nt 1-18 of SEQ ID No: 10) and has a single nick in the coding strand of the molecule at nt +7 relative to the start of transcription from the SP6 promoter. The position of the nick and the start of transcription initiation from the SP6 promoter are indicated.

DETAILED DESCRIPTION AND PREFERRED EMBODIMENTS

Definitions

Figure 1:
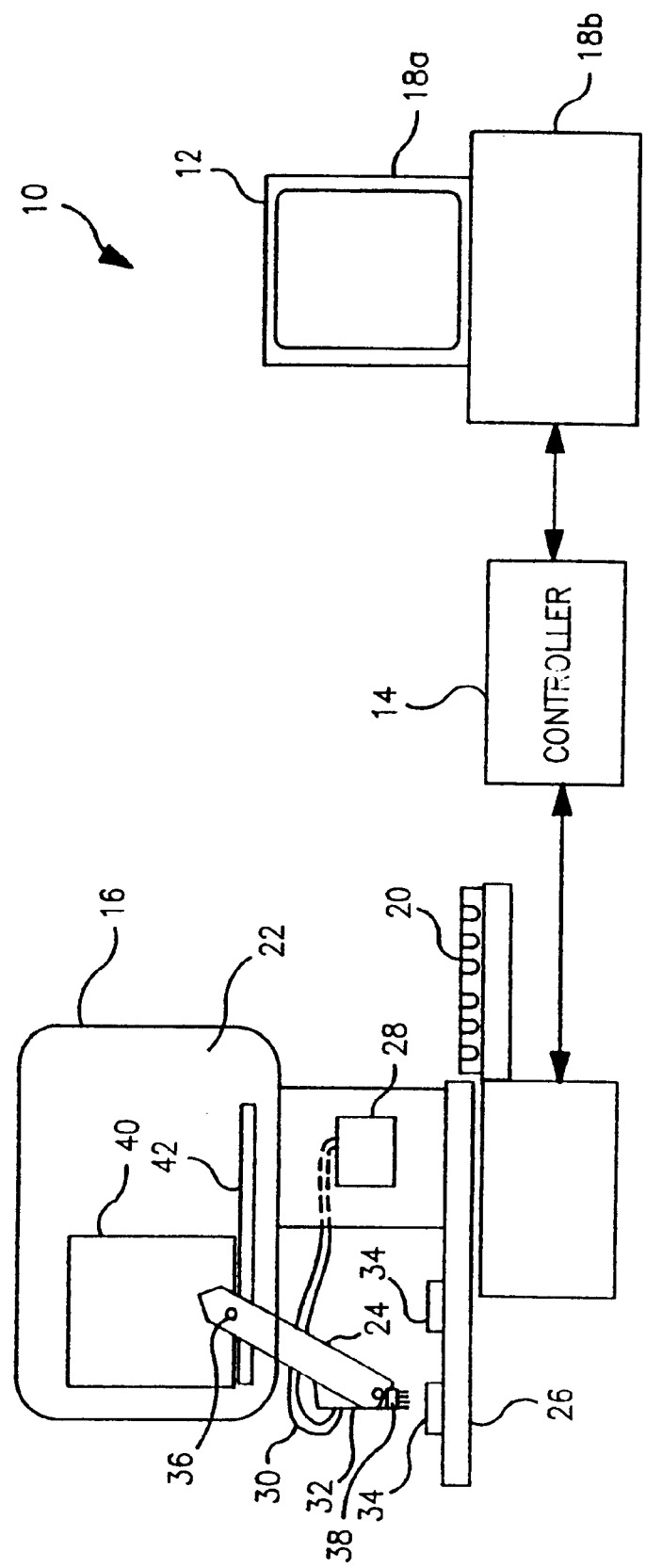
FIG. 1 illustrates a system for preparing arrays of a sample material for analysis.

Unless defined otherwise, all technical and scientific terms used herein have the same meaning as is commonly understood by one of skill in the art to which this invention belongs. All patents and publications referred to herein, such as U.S. Pat. No. 5,547,835, are incorporated by reference herein.

As used herein, the term "nucleic acid" refers to oligonucleotides or polynucleotides such as deoxyribonucleic acid (DNA) and ribonucleic acid (RNA) as well as analogs of either RNA or DNA, for example, made from nucleotide analogs, any of which are in single or double-stranded form. Nucleic acid molecules can be synthetic or can be isolated from a particular biological sample using any number of procedures which are well-known in the art, the particular procedure chosen being appropriate for the particluar biological sample.

As used herein, nucleotides include nucleoside mono-, di-, and triphosphates. Nucleotides also include modified nucleotides such as phosphorothioate nucleotides and deazapurine nucleotides. A complete set of chain-elongating nucleotides refers to four different nucleotides that can hybridize to each of the four different bases comprising the DNA template.

As used herein, a nucleic acid promoter-containing probe refers to a nucleic acid fragment that includes a double-stranded region encoding a promoter and a single-stranded region that contains at least 5 nucleotides at the 3'-end of the coding strand relative to the promoter that is complementary to a single stranded region at the 3'-end of a nucleic acid to be sequenced.

As used herein, the target nucleic acid is the nucleic acid that is sequenced. The target nucleic acid will contain or will be modified to contain at least about 5 nucleotides whose sequence is known for hybridization to the immobilized nucleic acid promoter-containing probe.

As used herein, nucleic acid synthesis refers to any process by which oligonucleotides or polynucleotides are generated, including, but not limited to processes involving chemical or enzymatic reactions.

As used herein, a base-specifically terminated ribonucleotides is one that generated during transcription by incorporation a nucleotide that results in transcription termination. Base-specifically terminating ribonucleoside triphophates, which produce base-specifically terminated ribonucleotides, are known to those of skill in the art. Examples of base-specifically terminating ribonucleoside triphosphates include, but are not limited to: 3'-deoxyribonucleoside triphosphates, such as 3'-dGTP, and others described herein and known to those of skill in the art.

As used herein, complementary when referring to two nucleotide sequences, means that the two sequences of nucleotides are capable of hybridizing, preferably with less than 25%, more preferably with less than 15%, even more preferably with less than 5%, most preferably with no mismatches between opposed nucleotides. Preferably the two molecules will hybridize under conditions of high stringency.

As used herein: stringency of hybridization in determining percentage mismatch is as follows:

1) high stringency: 0.1×SSPE, 0.1% SDS, 65° C.
2) medium stringency: 0.2×SSPE, 0.1% SDS, 50° C.
3) low stringency: 1.0×SSPE, 0.1% SDS, 50° C.

It is understood that equivalent stringencies may be achieved using alternative buffers, salts and temperatures.

As used herein, the term "array" refers to an ordered arrangement of members or positions. The array may contain any number of members or positions and can be in any variety of shapes. In preferred embodiments, the array is two-dimensional and contains n×m members, wherein m and n are integers that can be the same or different. In particularly preferred embodiments, n and m are each 4 or a multiple thereof.

The term "cross-linking agent" is art-recognized, and, as used herein, refers to reagents which can immobilize a nucleic acid to an insoluble-support, preferably through covalent bonds. Thus, appropriate "cross-linking agents" for use herein includes a variety of agents that are capable of reacting with a functional group present on a surface of the insoluble support and with a functional group present in the nucleic acid molecule. Reagents capable of such reactivity include homo- and hetero-bifunctional reagents, many of which are known in the art. Heterobifunctional reagents are preferred.

As used herein, the term "thiol-reactive functionality," refers to a functionality which is capable of rapid reaction with a nucleophilic thiol moiety to produce a covalent bond (e.g., a disulfide or thioether bond). In general, thiol groups are good nucleophiles, and preferred thiol-reactive functionalities are reactive electrophiles. A variety of thiol-reactive functionalities are known in the art, and include, for example, haloacetyls (preferably iodoacetyl), diazoketones, epoxy ketones, α, β-unsaturated carbonyls (e.g., α, β-enones) and other reactive Michael acceptors (including maleimide), acid halides, benzyl halides, and the like. In certain embodiments, a free thiol group of a disulfide can react with a free thiol group (i.e., by disulfide bond formation, including by disulfide exchange). A "thiol-reactive" cross-linking agent, as used herein, refers to a cross-linking reagent (or surface) which includes, or can be modified to include, at least one thiol-reactive functionality. It will be understood that reaction of a thiol group can be temporarily prevented by blocking with an appropriate protecting group, as is conventional in the art (see e.g., T. W. Greene and P. G. M. Wuts "Protective Groups in Organic Synthesis," 2nd ed. John Wiley & Sons, (1991)).

As used herein, a selectively cleavable linker is a linker that is cleaved under selected conditions, such as a photocleavable linker, a chemically cleavable linker and an enzymatically cleavable linker (i.e., a restriction endonuclease site or a ribonucleotide/RNase digestion). The linker is interposed between the support and immobilized DNA.

As used herein, the terms "protein", "polypeptide" and "peptide" are used interchangeably when referring to a translated nucleic acid (e.g. a gene product).

As used herein, "sample" shall refer to a composition containing a material to be detected. In a preferred embodiment, the sample is a "biological sample" (i.e., any material obtained from a living source (e.g. human, animal, plant, bacteria, fungi, protist, virus). The biological sample can be in any form, including solid materials (e.g. tissue, cell pellets and biopsies) and biological fluids (e.g. urine, blood, saliva, amniotic fluid and mouth wash (containing buccal cells)). Preferably solid materials are mixed with a fluid.

As used herein, "substrate" or "solid support" shall mean an insoluble support onto which a sample is deposited according to the materials as described herein. Examples of appropriate substrates include beads (e.g., silica gel, controlled pore glass, magnetic, Sephadex/Sepharose, cellulose), capillaries, flat supports such as glass fiber filters, glass surfaces, metal surfaces (steel, gold, silver, aluminum, copper and silicon), plastic materials including multiwell plates or membranes (e.g., of polyethylene, polypropylene, polyamide, polyvinylidenedifluoride), pins (e.g., arrays of pins suitable for combinatorial synthesis or analysis or beads in pits of flat surfaces such as wafers (e.g., silicon wafers) with or without plates.

As used herein, RNA polymerase refers to DNA-dependent RNA polymerases and RNA-dependent RNA polymerases. Any RNA polymerase that recognizes a specific promoter sequence and is capable of initiating transcription and elongating a RNA transcript is contemplated within the scope of the term herein. Exemplary RNA polymerases that may be used in the methods provided herein include, but are not limited to those obtained from: 1) archeabacteria, such as Halobacterium, Methanobacterium, Methanococcus, Sulfolobales and Thermoplasma; 2) eubacteria, such as gram negative bacteria, e.g., *Escherichia coli* and strains of Salmonella and Shigella, gram positive bacteria, e.g., *Bacillus subtilis* and *Staphlococcus aureus;* 3) bacteriophages, such as T7, T3, SP6, SP6 nicked and N4; 4) DNA viruses; 5) RNA viruses, such as influenza virus; 6) plants, such as wheat; and 7) eukaryotic RNA polymerase II isolated from fungii, e.g., *Saccharomyces cerevisae* and higher eukaryotic organisms, e.g., mammals. Also included within the scope of the term RNA polymerase as used herein is the RNA phage Qβ replicase.

As used herein, a promoter region refers to the portion of DNA of a gene that controls expression of DNA to which it is operatively linked. The promoter region includes specific sequences of DNA that are sufficient for RNA polymerase recognition, binding and transcription initiation. This portion of the promoter region is referred to as the promoter. In addition, the promoter region includes sequences that modulate this recognition, binding and transcription initiation activity of the RNA polymerase. These sequences may be cis acting or may be responsive to trans acting factors. Promoters, depending upon the nature of the regulation, may be constitutive or regulated. A constitutive promoter is always turned on. A regulatable promoter requires specific signals to be turned on or off. A developmentally regulated promoter is one that is turned on or off as a function of development. The promoter can be of a consensus sequence or variant. When a non-wild-type promoter is used, transcription will occur at a rate sufficient to produce a detectable transcript, and is typically at least about 5–10% of the rate at which transcription would have occurred if a wild-type or native promoter had been used by the RNA polymerase to transcribe the nucleic acid in vitro.

As used herein, a "promoter-containing nucleic acid" is a nucleic acid that contains a sequence of nucleotides that directs the site-specific binding of an RNA polymerase molecule to form an open transcription initiation complex that is capable of initiating RNA synthesis in the presence of ribonucleotide triphosphates (i.e., encodes a functional promoter sequence).

As used herein, a "coding strand" refers to the nucleic acid strand of a promoter-containing nucleic acid that has the same polarity as a corresponding mRNA molecule initiated from that promoter.

As used herein, a "matrix material" refers to a material used in mass spectrometry that is a proton donating, UV absorbing material, usually organic acid, that forms crystalline matrix-nucleic acid structures that are readily ionizable during MALDI. An exemplary matrix material is a solution of 3-hydroxypicolinic acid (3-HPA, 0.7 M in 50% acetonitrile, 10% ammonium citrate).

Methods For Sequencing

Mass spectrometric methods of sequencing nucleic acids are provided. The sequencing methods use immobilized nucleic acid promoter-containing probes that contain a double stranded region encoding a promoter and a single stranded region for hybridizing target nucleic acids. The nucleic acid sequence is determined by generating a set of nested base-specific chain terminated RNA transcripts that are analyzed using mass spectrometry.

When analyzing nucleic acids using mass spectrometry herein, RNA is presently preferred to DNA. While DNA is often the preferred vehicle for sequence, the methods herein are advantageously use RNA. It is appears that RNA fragments are more stable during matrix-assisted laser desorption/ionization (MALDI) mass spectrometry than DNA fragments. Without being bound by any theory, the enhanced stability may result from the presence of the 2'-hydroxyl group on the sugar moiety of RNA, which helps to reduce depurination during the MALDI process.

RNA Polymerases and Promoters

Any RNA polymerase capable of directing the in vitro transcription of an RNA molecule is contemplated for use in the methods described herein. Methods for isolating and purifying RNA polymerase molecules are well known to those of skill in the art: Qβ replicase (e.g., see U.S. Pat. No. 5,696,249, Re: 35,443 and Eoyang et al. (1971) in *Procedures in Nucleic Acid Research,* Cantoni and Davies, eds., Volume 2, pp. 829–839, Harper and Rowe, N.Y.); bacteria (e.g., *E. coli,* see Burgess and Jendrisak (1975) *Biochemistry* 14:4634–4638 and Hager et al. (1 990) *Biochemistry* 29:7890–7894; Leishmania, e.g., see Sadhukhan et al. (1997) *Mol. Cell. Biochem.* 171:105–114; *Bacillus subtilis,* Giacomoni (1980) *Eur. J. Biochem.* 106:579–591); phage (e.g., T7, McDonnell et al. (1977) *J. Mol. Biol.* 89:719–736 and Studier et al. (1969) *Virology* 39:562–574; see also He et al. (1997) *Protein Expr. Purif.* 9: 142–151); viruses (e.g., rhabdovirus, see Das et al. (1996) *Methods Enzymol.* 275:99–122; turnip mosiac virus, see Deidman et al. (1997) *J. Viral Meth.* 64:184–195; vaccinia, Gershon et al. (1996) *Methods Enzymol.* 275:35–57); and mammalian (e.g., yeast poll, Koleske et al. (1996) *Methods Enzymol.* 273:176–184; human poIII, Maldonado et al. (1996) *Methods Enzymol.* 274:72–100). In addition, a number of prokaryotic, eukaryotic, bacteriophage and viral RNA polymerases are commercially available (e.g., sold by Stratagene, La Jolla, Calif.; Boehringer Mannheim, Indianapolis, Ind. ; Pharmacia, Uppsala, Sweden; and Sigma Chemical Corp, St. Louis, Mo.).

In practicing the methods, DNA-dependent RNA polymerases and RNA-dependent RNA polymerases may be used. For example, RNA polymerases that may be used in the methods provided herein include, but are not limited to those obtained from: 1) archeabacteria, such as Halobacterium, Methanobacterium, Methanococcus, Sulfolobales and Thermoplasma; 2) eubacteria, such as gram negative bacteria, e.g., *Escherichia coli* and strains of Salmonella and Shigella, gram positive bacteria, e.g., *Bacillus subtilis* and *Staphlococcus aureus;* 3) bacteriophages, such as T7, T3, SP6 and N4; 4) DNA viruses; 5) RNA viruses, such as influenza virus; 6) plants and plant viruses, such as wheat and turnip mosiac virus; and 7) eukaryotic RNA polymerase II isolated from fungii, e.g., *Saccharomvces cerevisae* and higher eukaryotic organisms, e.g., mammals (e.g., for a review see In *RNA Polymerase and the Regulation of Transcription,* Rezinkoff et al., eds, Elsevier, N.Y.). Also included for use herein is the Qβ replicase from the Qβ RNA phage (e.g., see U.S. Pat. Nos. 5,670,353, 5,696,249 and Re: 35,443).

The selection of the appropriate RNA polymerase for any given nucleic acid template to be sequenced is within the skill of the skilled artisan and varies according to the nucleic acid molecule to be sequenced. The selection may be determined empirically following the teachings known to those of skill in the art, including those described herein.

Each nucleic acid promoter-containing probe used in the sequencing methods described herein contains a promoter. The promoters used in the methods herein may be obtained from any source, i.e., recombinant or naturally-occurring promoter elements, or may be assembled from synthetic nucleic acid oligonucleotide sequences. For example, the nucleic acid containing a promoter may be obtained directly from a variety of different organisms, such as bacteria, viruses and eukaryotic organisms, by cloning or may be obtained from commercially available expression vectors (e.g., T7, T3, SP6 and $\lambda_{PL}$ and $\lambda_{PR}$ promoters; Boehringer Mannheim and Pharmacia; bla or lac promoters, RSV-LTR promoter and F9-1 promoter; Stratagene). The selection of the appropriate promoter will depend on the nucleic acid to be sequenced, sequencing conditions, and most importantly, on the RNA polymerase selected for transcription.

Immobilization of Nucleic Acid Promoter-containing Probes

In preferred embodiments, the nucleic acid promoter-containing probe is immobilized, directly or by means of a cross-linking agent, to a solid support provided herein. Preferred solid supports are those which can support linkage of nucleic acids thereto at high densities, preferably such that the covalently bound nucleic acids are present on the substrate at a density of at least about 20 fmol/mm$^2$, more preferably at least about 75 fmol/mm$^2$, still more preferably at least about 85 fmol/mm$^2$, yet more preferably at least about 100 fmol/mm$^2$, and most preferably at least about 150 fmol/mm$^2$. Among the most preferred substrates for use in the particular methods of immobilizing nucleic acids to substrates provided herein is silicon, whereas less preferred substrates include polymeric materials such as polyacrylamide. Substrates for use in methods of producing arrays provided herein include any of a wide variety of insoluble support materials including, but not limited to silica gel, controlled pore glass, cellulose, glass fiber filters, glass surfaces, metal surfaces (steel, gold, silver, aluminum, silicon and copper), plastic materials (e.g., of polyethylene, polypropylene, polyamide, polyvinyldenedifluoride) and silicon.

In embodiments of the methods in which a cross-linking reagent is not employed, a modified nucleic acid is reacted directly with a appropriately functionalized surface to yield immobilized nucleic acid. Thus, for example, an iodoacetyl-modified surface (or other thiol-reactive surface functionality) can react with a thiol-modified nucleic acid to provide immobilized nucleic acids.

In embodiments using a cross-linking agent, the cross-linking agent is selected to provide a high density of nucleic acids immobilized on the insoluble support. The cross-linking agent (and other reagents used to functionalize the support surface or the nucleic acid molecule) can be selected to provide any desired spacing of the immobilized nucleic acid molecules from the support surface, and to provide any desired spacing of the immobilized nucleic acids from each other. Thus, steric encumbrance of the nucleic acid molecules can be reduced or eliminated by choice of an appropriate cross-linking agent. In certain embodiments, the cross-linking reagent can be selected to provide multiple reactive functionalities as used in dendrimer synthesis for attachment of multiple nucleic acids to a single cross-linking moiety. Preferably, the cross-linking agent is selected to be highly reactive with the nucleic acid molecule, to provide rapid, complete, and/or selective reaction. In preferred embodiments, the reaction volume of the reagents (e.g., the thiol group and the thiol-reactive functionality) is small.

Modified Nucleic Acid Promoter-containing Probes and Linkers

Preferred nucleic acid promoter-containing probes for use herein are "thiol-modified nucleic acids," i.e., nucleic acids derivatized to contain at least one reactive thiol moiety. As described in further detail in Example 1, below, nucleic acids containing at least one reactive thiol are preferably made by treating a nucleic acid containing a 3' or 5' disulfide with a reducing agent, which preferably will not compete in subsequent reactions (i.e. will not react with an iodoacetimido functionality). Disulfide-derivatized nucleic acids can be synthesized according to a variety of methods. For example, a nucleic acid can be modified at the 3'- or 5'-terminus by reaction with a disulfide-containing modifying a reagent. Alternatively, a thiolated primer can by enzymatically or non-enzymatically attached to the nucleic acid. A 5'-phosphoramidate functionality can also provide an attachment point for a thiol or disulfide-containing cytosine or deoxycytosine. Examples of reducing agents appropriate for reduction of a disulfide-modified nucleic acid include: tris-(2-carboxyethyl)phosphine (TCEP) (preferably a concentration in the range of 1–100 mM (most preferably about 10 mM)) is reacted at a pH in the range of 3–6 (most preferably about 4.5), a temperature in the range of 20–45° C. (most preferably about 37° C.) for a time period in the range of about 1 to about 10 hrs (most preferably for about 5 hrs); dithiothreitol (preferably a concentration in the range of 25 to 100 mM (depending on whether the reactant is isolated) is reacted at a pH in the range of 6–10 (most preferably about 8) and at a temperature in the range of 25–45° C. (most preferably about 37° C.)) for a time in the range of about 1 to about 10 hrs (most preferably about 5 hrs). TCE provides an advantage in the low pH at which it is reactive. This low pH effectively protonates thiols, thus suppressing nucleophilic reactions of thiols and resulting in fewer side reactions than with other disulfide reducing agents which are employed at higher pH.

As further described in Example 1, below, a preferred bifunctional cross-linking agent is N-succinimidyl(4-iodacetyl) aminobenzoate (SIAB). Other crosslinking agents include, but are not limited to, dimaleimide, dithio-bis-nitrobenzoic acid (DTNB), N-succinimidyl-S-acetylthioacetate (SATA), N-succinimidyl-3-(2-pyridyidithio propionate (SPD P), succinimidyl 4-(N-maleimidomethyl) cyclohexane-1-carboxylate (SMCC) and 6-hydrazinonicotimide (HYNIC) may also be used in the novel process. For further examples of cross-linking reagents, see, e.g., Wong "Chemistry of Protein Conjugation and Cross-Linking," CRC Press (1991), and Hermanson, "Bioconjugate Techniques" Academic Press (1995).

In other embodiments, the nucleic acid is immobilized using the photocleavable linker moiety that is cleaved during mass spectrometry. Exemplary photolabile cross-linker include, but are not limited to, 3-amino-(2-nitrophenyl) propionic acid (Brown et al. (1995) Molecular Diversity, pp.4–12 and Rothschild et a. (1996) Nucleic Acids Res. 24:361–66).

A nucleic acid promoter-containing probe can be directly linked to a solid support via a reversible or irreversible bond between an appropriate functionality (L') on the target nucleic acid molecule (T) and an appropriate functionality (L) on the capture molecule. A reversible linkage can be such that it is cleaved under the conditions of mass spectrometry (i.e., a photocleavable bond such as a charge transfer complex or a labile bond being formed between relatively stable organic radicals).

Furthermore, the linkage can be formed with L' being a quaternary ammonium group, in which case, preferably, the surface of the solid support carries negative charges which repel the negatively charged nucleic acid backbone and thus facilitate the desorption required for analysis by a mass spectrometer. Desorption can occur either by the heat created by the laser pulse and/or, depending on L,' by specific absorption of laser energy which is in resonance with the L' chromophore.

Thus, the L-L' chemistry can be of a type of disulfide bond (chemically cleavable, e.g., by mercaptoethanol or dithioerythrol; a biotin/streptavidin system; a heterobifunctional derivative of a trityl ether group; see, e.g., Köster et al. (1990) "A Versatile Acid-Labile Linker for Modification of Synthetic Biomolecules," Tetrahedron Letters 31:7095) that can be cleaved under mildly acidic conditions as well as under conditions of mass spectrometry, a levulinyl group cleavable under almost neutral conditions with a hydrazinium/acetate buffer, an arginine-arginine or lysine-lysine bond cleavable by an endopeptidase enzyme like trypsin or a pyrophosphate bond cleavable by a pyrophosphatase, or a ribonucleotide bond in between the oligodeoxynucleotide sequence, which can be cleaved, for example, by a ribonuclease or alkali.

The functionalities, L and L,' can also form a charge transfer complex and thereby form the temporary L-L' linkage. Since in many cases the "charge-transfer band" can be determined by UV/vis spectrometry (see, e.g., Organic Charge Transfer Complexes by R. Foster, Academic Press, 1969), the laser energy can be tuned to the corresponding energy of the charge-transfer wavelength and, thus, a specific desorption off the solid support can be initiated. Those skilled in the art will recognize that several combinations can serve this purpose and that the donor functionality can be either on the solid support or coupled to the nucleic acid molecule to be detected or vice versa.

In yet another approach, a reversible L-L' linkage can be generated by homolytically forming relatively stable radicals. Under the influence of the laser pulse, desorption (as discussed above) as well as ionization will take place at the radical position. Those skilled in the art will recognize that other organic radicals can be selected and that, in relation to the dissociation energies needed to homolytically cleave the bond between them, a corresponding laser wavelength can be selected (see e.g., Reactive Molecules by C. Wentrup, John Wiley & Sons, 1984).

As noted, at least three version of immobilization are contemplated herein: 1) the target nucleic acid is amplified or obtained (the target sequence or surrounding DNA sequence must be known to make primers to amplify or isolated); 2) the primer nucleic acid is immobilized to the solid support and the target nucleic acid is hybridized thereto to form a promoter sequence; or 3) a double stranded nucleic acid encoding a promoter (amplified or isolated) is immobilized through linkage to one predetermined strand, and in vitro transcription is initiated in the presence of a predetermined deoxy ribonucleotide.

In the embodiments where the primer nucleic acid is immobilized on the solid support and the target nucleic acid is hybridized thereto, the inclusion of the cleavable linker allows the primer DNA to be immobilized at the 5'-end so that free 3'-OH is available for "hybridizing" target DNA to the free DNA strand and initiating transcription to.

Any linker known to those of skill in the art for immobilizing nucleic acids to solid supports may be used herein to link the nucleic acid to a solid support. The preferred linkers herein are the selectively cleavable linkers, particularly those exemplified herein. Other linkers include, acid cleavable linkers, such as bismaleimideothoxy propane and acid-labile trityl linkers. Acid cleavable linkers, photocleavable and heat sensitive linkers may also be used, particularly where it may be necessary to cleave the targeted agent to permit it to be more readily accessible to reaction.

Acid Cleavable Linkers

Acid cleavable linkers include, but are not limited to, bismaleimideothoxy propane; and adipic acid dihydrazide linkers (see, e.g., Fattom et al. (1992) Infection & Immun. 60:584–589) and acid labile transferrin conjugates that contain a sufficient portion of transferrin to permit entry into the intracellular transferrin cycling pathway (see, e.g., Welhöner et al. (1991) J. Biol. Chem. 266:4309–4314).

Photocleavable Linkers

Photocleavable linkers are linkers that are cleaved upon exposure to light (see, e.g., Goldmacher et al. (1992) Bioconj. Chem. 3:104–107), thereby releasing the targeted agent upon exposure to light.

Photocleavable linkers that are cleaved upon exposure to light are known (see, e.g., Hazum et al. (1981) in Pept.,

*Proc. Eur. Pept. Symp.*, 16*th*, Brunfeldt, K (Ed), pp. 105–110, which describes the use of a nitrobenzyl group as a photocleavable protective group for cysteine; Yen et al. (1989) *Makromol. Chem* 190:69–82, which describes water soluble photocleavable copolymers, including hydroxypropylmethacrylamide copolymer, glycine copolymer, fluorescein copolymer and methylrhodamine copolymer; Goldmacher et al. (1992) *Bioconj. Chem.* 3:104–107, which describes a cross-linker and reagent that undergoes photolytic degradation upon exposure to near UV light (350 nm); and Senter et al. (1985) *Photochem. Photobiol* 42:231–237, which describes nitrobenzyloxycarbonyl chloride cross linking reagents that produce photocleavable linkages), thereby releasing the targeted agent upon exposure to light. In preferred embodiments, the nucleic acid is immobilized using the photocleavable linker moiety that is cleaved during mass spectrometry.

Chemically Cleavable Linkers

A variety of chemically cleavable linkers may be used to introduce a cleavable bond between the immobilized nucleic acid and the solid support. Acid-labile linkers are presently preferred chemically cleavable linkers for mass spectrometry, especially MALDI-TOF MS, because the acid labile bond is cleaved during conditioning of the nucleic acid upon addition of the 3-HPA matrix solution. The acid labile bond can be introduced as a separate linker group, e.g., the acid labile trityl groups or may be incorporated in a synthetic nucleic acid linker by introducing one or more silyl internucleoside bridges using diisopropylsilyl, thereby forming diisopropylsilyl-linked oligonucleotide analogs. The diisopropylsilyl bridge replaces the phoshodiester bond in the DNA backbone and under mildly acidic conditions, such as 1.5% trifluoroacetic acid (TFA) or 3-HPA/1% TFA MALDI-TOF matrix solution, results in the introduction of one or more intra-strand breaks in the DNA molecule. Methods for the preparation of diisopropylsilyl-linked oligonucleotide precursors and analogs are known to those of skill in the art (see e.g., Saha et al. (1993) *J. Org. Chem.* 58:7827–7831). These oligonucleotide analogs may be readily prepared using solid state oligonucleotide synthesis methods using diisopropylsilyl derivatized deoxyribonucleosides.

Modification of Nucleic Acids

A. Mass Modification

In certain embodiments, nucleic acids modified at positions other than the 3'- or 5'-terminus can be used. Modification of the sugar moiety of a nucleotide at positions other than the 3' and 5' position is possible through conventional methods. Also, nucleic acid bases can be modified, e.g., as described in F. Eckstein, ed., "*Oligonucleotides and Analogues: A Practical Approach*," IRL Press (1991). Such a linker arm can be modified to include a thiol moiety. Alternatively, backbone-modified nucleic acids can be used so that the thiol group can be attached to the nitrogen center provided by the modified phosphate backbone.

In preferred embodiments, modification of a nucleic acid, e.g., as described above, does not substantially impair the ability of the nucleic acid or nucleic sequence to hybridize to its complement. Thus, any modification should preferably avoid substantially modifying the functionalities of the nucleic acid which are responsible for Watson-Crick base pairing. The nucleic acid can be modified such that a non-terminal thiol group is present, and the nucleic acid, when immobilized to the support, is capable of self-complementary base pairing to form a "hairpin" structure having a duplex region.

B. Other Modifying RNA Analogs

In practicing the methods described herein, a set of nested base-specific chain terminated RNA transcripts are generated during transcription by the incorporation of a modified base-specific chain terminating ribonucleotide analog. Any ribonucleoside triphosphate analog that results in the sequence-specific arrest of transcription elongation upon incorporation into an RNA molecule by an RNA polymerase may be used in the methods herein. Presently preferred ribonucleotide analogs are 3'-deoxyribonucleotides. The utilization of 3'-deoxyribonucleoside triphosphates by RNA polymerases has been reported to result in base-specific termination of transcription (e.g., see Axelrod et al. (1985) *Biochemistry* 24:5716–5723; Tyagarajan et al. (1985) *Biochemistry* 30:10920–10924).

In certain embodiments, in addition to a base-specific chain terminating ribonucleoside triphosphate analog, additional ribonucleotide analogs can be added to reduce the secondary structure of the resulting RNA transcript. For example, the incorporation of riboinosine using inosine 5'-triphosphate is known to reduce the secondary structure of RNA products. In the presence of a dinucleotide guanine initiator, inosine 5'-triphosphate can effectively substitute for GTP in in vitro transcription reactions (e.g., Axelrod et al. (1985) *Biochemistry* 24:5716–5723).

In addition, modified ribonucleotide analogs may be added to the transcription mixture to increase the efficiency of transcriptional termination and/or transcript release to promote and facilitate the rate enzyme turnover. For example, the addition of 4-thio UTP, 5-bromo UTP, 5-iodo CTP alter the hydrogen bonding of the nucleic acid facilitating, at least with some RNA polymerases, transcriptional termination and transcript release.

Solid Supports and Substrates

Examples of insoluble supports and substrates for use herein include, but are not limited to, beads (silica gel, controlled pore glass, magnetic beads, Sephadex/Sepharose beads, cellulose beads, etc.), capillaries, flat supports such as glass fiber filters, glass surfaces, metal surfaces (steel, gold, silver, aluminum, silicon and copper), plastic materials including multiwell plates or membranes (e.g., of polyethylene, polypropylene, polyamide, polyvinyldenedifluoride), wafers, combs, pins (e.g., arrays of pins suitable for combinatorial synthesis or analysis) or beads in pits of flat surfaces such as wafers (e.g., silicon wafers), with or without filter plates.

Mass Spectrometry

Once transcription is complete, the nucleic acids can be analyzed by any of a variety of means including, for example, spectrometric techniques such as UV/VIS, IR, fluorescence, chemiluminescence, or NMR spectroscopy, mass spectrometry, or other methods know in the art, or combinations thereof. Preferred mass spectrometer formats include the ionization (I) techniques, such as matrix assisted laser desorption (MALDI), continuous or pulsed electrospray (ESI) and related methods (e.g. Ionspray or Thermospray), or massive cluster impact (MCI); these ion sources can be matched with detection formats including linear or reflectron time-of-flight (TOF), single or multiple quadruple, single or multiple magnetic sector, Fourier Transform ion cyclotron resonance (FTICR), ion trap, and combinations thereof to yield a hybrid detector (e.g., ion-trap/time-of-flight). For ionization, numerous matrix/wavelength combinations (MALDI) or solvent combinations (ESI) can be employed.

Preparation of DNA Arrays

In preferred embodiments, nucleic acid promoter-containing probes are immobilized at high densities to the surface of a solid support in an array format. Particularly suitable methods for forming these DNA arrays are those described herein and U.S. application Ser. Nos. 08/746,053, 08/787,639 and 08/786,988. The subject matter of each pending U.S. applications is herein incorporated by reference in its entirety.

FIG. 1 illustrates one system for preparing arrays of sample material for analysis by a diagnostic tool. FIG. 1 depicts a system 10 that includes a data processor 12, a motion controller 14, a robotic arm assembly 16, a monitor element 18A, a central processing unit 18B, a microliter plate of source material 20, a stage housing 22, a robotic arm 24, a stage 26, a pressure controller 28, a conduit 30, a mounting assembly 32, a pin assembly 38, and substrate elements 34. In the view shown by FIG. 1, it is also illustrated that the robotic assembly 16 can include a moveable mount element 40 and a horizontal slide groove 42. The robotic arm 24 can optionally pivot about a pin 36 to increase the travel range of the arm 24 so that arm 24 can disposes the pin assembly 38 above the source plate 20.

The data processor 12 depicted in FIG. 1 can be a conventional digital data processing system such as an IBM PC compatible computer system that is suitable for processing data and for executing program instructions that will provide information for controlling the movement and operation of the robotic assembly 16. It will be apparent to one skilled in the art that the data processor unit 12 can be any type of system suitable for processing a program of instructions signals that will operate the robotic assembly that is integrated into the robotic housing 16. Optionally the data processor 12 can be a micro-controlled assembly that is integrated into robotic housing 16. In further alternative embodiments, the system 10 need not be programmable and can be a singleboard computer having a firmware memory for storing instructions for operating the robotic assembly 16.

In the embodiment depicted in FIG. 1, there is a controller 14 that electronically couples between the data processor 12 and the robotic assembly 16. The depicted controller 14 is a motion controller that drives the motor elements of the robotic assembly 16 for positioning the robotic arm 24 at a selected location. Additionally, the controller 14 can provide instructions to the robotic assembly 16 to direct the pressure controller 28 to control the volume of fluid ejected from the individual pin elements of the depicted pin assembly 38. The design and construction of the depicted motion controller 14 follows from principles well known in the art of electrical engineering, and any controller element suitable for driving the robotic assembly 16 can be practiced without departing from the scope thereof.

The robotic assembly 16 depicted in FIG. 1 electronically couples to the controller 14. The depicted robotic assembly 16 is a gantry system that includes an XY table for moving the robotic arm about a XY plane, and further includes a Z axis actuator for moving the robotic arm orthogonally to that XY plane. The robotic assembly 16 depicted in FIG. 1 includes an arm 24 that mounts to the XY stage which moves the arm within a plane defined by the XY access. In the depicted embodiment, the XY table is mounted to the Z actuator to move the entire table along the Z axis orthogonal to the XY plane. In this way, the robotic assembly provides three degrees of freedom that allows the pin assembly 38 to be disposed to any location above the substrates 34 and the source plate 20 which are shown in FIG. 1 as sitting on the stage 26 mounted to the robotic assembly 16.

The depicted robotic assembly 16 follows from principles well known in the art of electrical engineering and is just one example of a robotic assembly suitable for moving a pin assembly to locations adjacent a substrate and source plate such as the depicted substrate 34.

Accordingly, it will be apparent to one of ordinary skill in the art that alternative robotic systems can be practiced following the descriptions herein without departing from the scope thereof.

FIG. 1 depicts an embodiment of a robotic assembly 16 that includes a pressure controller 28 that connects via a conduit 30 to the mount 32 that connects to the pin assembly 38. In this embodiment the mount 32 has an interior channel for fluidicly coupling the conduit 30 to the pin assembly 38. Accordingly, the pressure controller 28 is fluidicly coupled by the conduit 30 and the mount 32 to the pin assembly 38. In this way the controller 14 can send signals to the pressure controller 28 to control selectively a fluid pressure delivered to the pin assembly 38.

Figure 2:
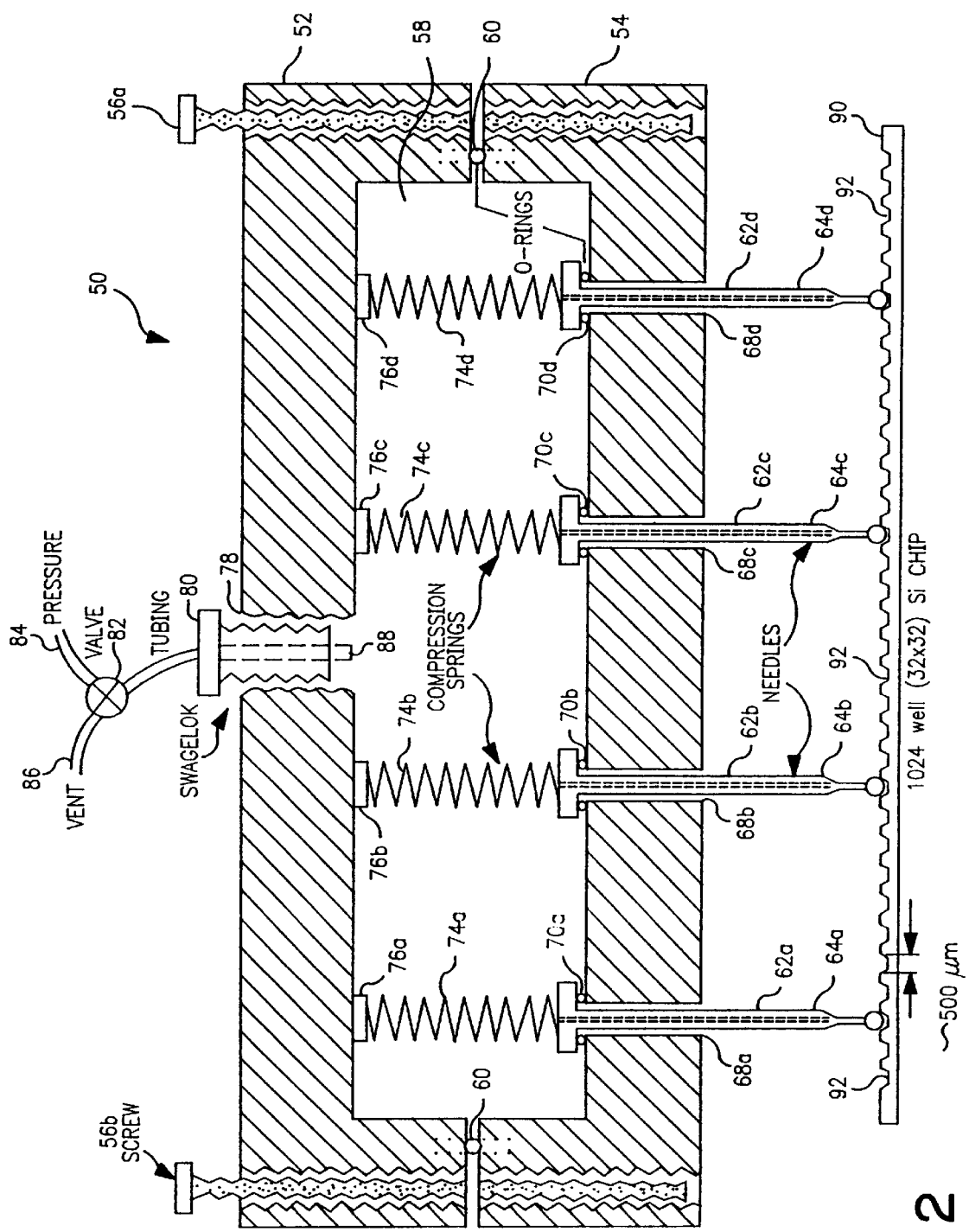
FIG. 2 illustrates a pin assembly suitable for use with the system depicted in FIG. 1 for implementing a parallel process of dispensing material to a surface of a substrate.

FIG. 2 depicts one embodiment of a pin assembly 50 suitable for practice with the system depicted in FIG. 1 which includes the pressure controller 28. In the depicted embodiment, the pin assembly 50 includes a housing formed from an upper portion 52 and a lower portion 54 that are joined together by the crews 56A and 56B to define an interior chamber volume 58. FIG. 2 further depicts that to fluidicly seal the interior chamber volume 58 the housing can include a seal element depicted in FIG. 2 as an O-ring gasket 60 that sites between the upper block and the lower block 54 and surrounds completely the perimeter of the interior chamber volume 58. FIG. 2 further depicts that the pin assembly 50 includes a plurality of vesicles 62A–62D, each of which include an axial bore extending therethrough to form the depicted holding chambers 64A–64D. Each of the depicted vesicles extends through a respective aperture 68A–68D disposed within the lower block 54 of the housing.

As further shown in the depicted embodiment, each of the vesicles 62A–62D has an upper flange portion that sits against a seal element 70A–70D to form a fluid-tight seal between the vesicle and the lower block 54 to prevent fluid from passing through the apertures 68A–68D. To keep the seal tight, the depicted pin assembly 50 further includes a set of biasing elements 74A–74D depicted in FIG. 2 as springs which, in the depicted embodiments, are in a compressed state to force the flange element of the vesicles 62A–62D against their respective seal elements 70A–70D. As shown in FIG. 2, the biasing elements 74A–74D extend between the vesicles and the upper block 52. Each of the springs 74A–74D can be fixedly mounted to a mounting pad 76A–76D where the spring elements can attach to the upper block 52. The upper block 52 further includes an aperture 78 depicted in FIG. 2 as a centrally disposed aperture that includes a threaded bore for receiving a swagelok 80 that can be rotatably mounted within the aperture 78.

As further depicted in FIG. 2, the swagelok 80 attaches by a conduit to a valve 82 than can connect the swagelok 80 to a conduit 84 that can be coupled to a pressure source, or alternatively can couple the swagelok 80 to a conduit 86 that provides for venting of the interior chamber 58. A central bore 88 extends through the swagelok 80 and couples to the tubing element which further connects to the valve 82 to thereby fluidicly and selectively couple the interior chamber volume 58 to either a pressure source, or a venting outlet.

The pin assembly 50 described above and depicted in FIG. 2 disposed above a substrate element 90 that includes a plurality of wells 92 that are etched into the upper surface of the substrate 90. As illustrated by FIG. 2, the pitch of the vesicles 62A–62D is such that each vesicle is spaced from the adjacent vesicles by a distance that is an integral multiple of the pitch distance between wells 92 etched into the upper surface of the substrate 90. As will be seen from the following description, this spacing facilitates the parallel dispensing of fluid, such that fluid can be dispensed into a plurality of wells in a single operation. Each of the vesicles can be made from stainless steel, silica, polymeric material or any other material suitable for holding fluid sample. In one example, 16 vesicles are employed in the assembly, which are made of hardened beryllium copper, gold plated over nickel plate. They are 43.2 mm long and the shaft of the vesicle is graduated to 0.46 mm outer diameter with a concave tip. Such a pin was chosen since the pointing accuracy can be approximately 501 micrometers. However, it will be apparent that any suitable pin style can be employed for the device, including but not limited to flat, star-shaped, concave, pointed solid, pointed semi-hollow, angled on one or both sides, or other such geometries.

Figure 3:
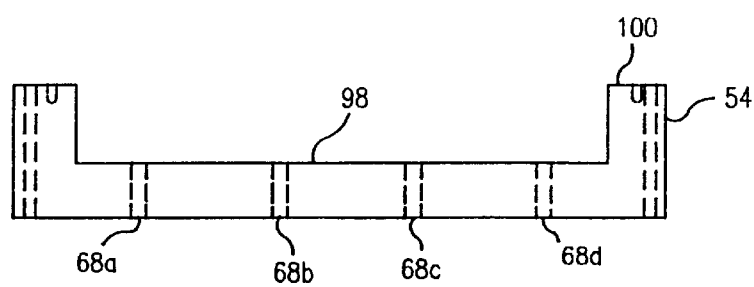
FIG. 3 depicts a bottom portion of the assembly shown in FIG. 2.

FIG. 3 shows from a side perspective the lower block 54 of the pin assembly 50 depicted in FIG. 2. FIG. 3 shows approximate dimensions for one pin assembly. As shown, the lower block 54 has a bottom plate 98 and a surrounding shoulder 100. The bottom plate 98 is approximately 3 mm in thickness and the shoulder 100 is approximately 5 mm in thickness.

Figure 4:
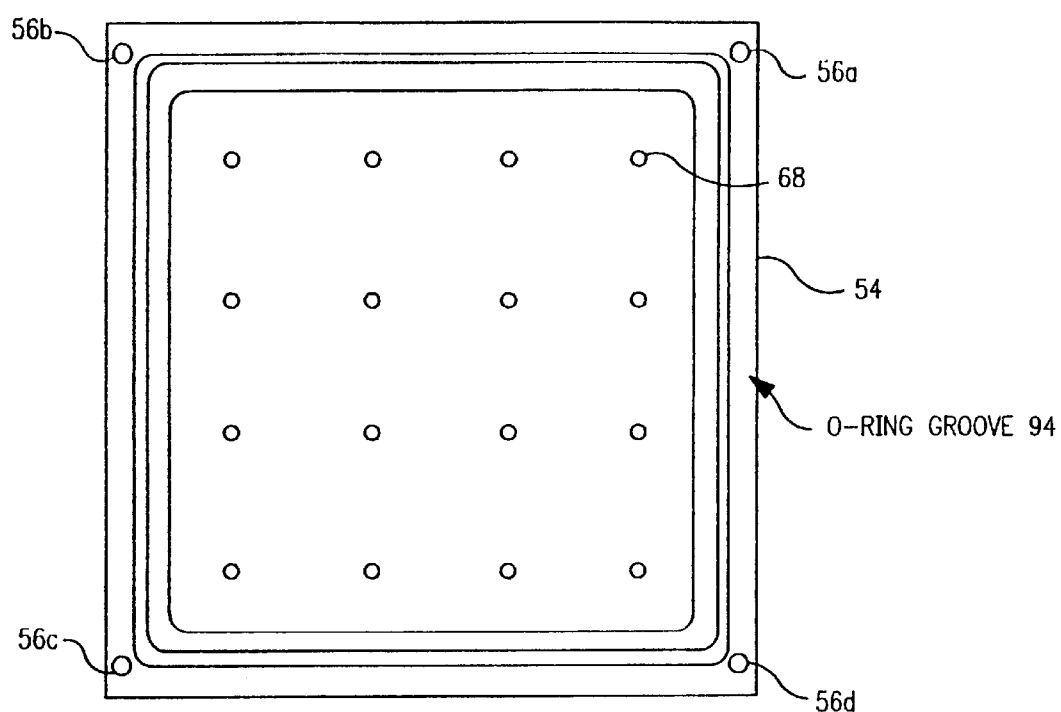
FIG. 4 depicts an alternative view of the bottom portion of the pin assembly depicted in FIG. 2.

FIG. 4 shows from an overhead perspective the general structure and dimensions for one lower block 54 suitable for use with the pin assembly for use with the pin assembly 50 shown in FIG. 2. As shown in FIG. 4, the lower block 54 includes a four-by-four matrix of apertures 68 to provide 16 apertures each suitable for receiving a vesicle. As described above with reference to FIG. 2, the spacing between the aperture 68 is typically an integral multiple of the distance between wells on a substrate surface as well as the wells of a source plate. Accordingly, a pin assembly having the lower block 54 as depicted in FIG. 4 can dispense fluid in up to 16 wells simultaneously. FIG. 4 also shows general dimensions of one lower block 54 such that each side of block 54 is generally 22 mm in length and the pitch between aperture 68 is approximately 4.5 mm. Such a pitch is suitable for use with a substrate where fluid is to be dispensed at locations approximately 500 µm apart, as exemplified by the substrate 90 of FIG. 2. FIG. 4 also shows that the lower block 54 can include an optional O-ring groove 94 adapted for receiving an O-ring seal element, such as the seal element 60 depicted in FIG. 2. It is understood that such a groove element 94 can enhance and improve the fluid seal formed by the seal element 60.

The pinblock can be manufactured of stainless steel as this material can be drilled accurately to about +25 µm, but a variety of probe materials can also be used, such as G10 laminate, PMMA or other suitable material. The pin block can contain any number of apertures and is shown with 16 receptacles which hold the 16 pins in place. To increase the pointing accuracy of each pin, an optional alignment place can be placed below the block so that about 6 mm of the pin tip is left exposed to enable dipping into the wells of a microtiter plate. The layout of the probes in the depicted tool is designed to coordinate with a 384-well microtiter plate, thus the center-to-center spacing of the probes in 4.5 mm. An array of 4×4 probes was chosen since it would produce an array that would fit in less than one square inch, which is the travel range of an xy stage of a MALDI TOF MS employed by the assignee. The pintool assembly is completed with a stainless steel cover on the top side of the device which is then attached onto the Z-arm of the robot.

With references to FIG. 5, the robotic assembly 16 employs a pin tool assembly 38 that is configured similarly as the pin tool assembly 50 depicted in FIG. 2. The pressure controller 28 selectively controls the pressure within chamber 58. With this embodiment, a control program operates on the data processor 12 to control the robotic assembly 16 in a way that the assembly 16 prints an array of elements on the substrates 34.

Figure 5A:
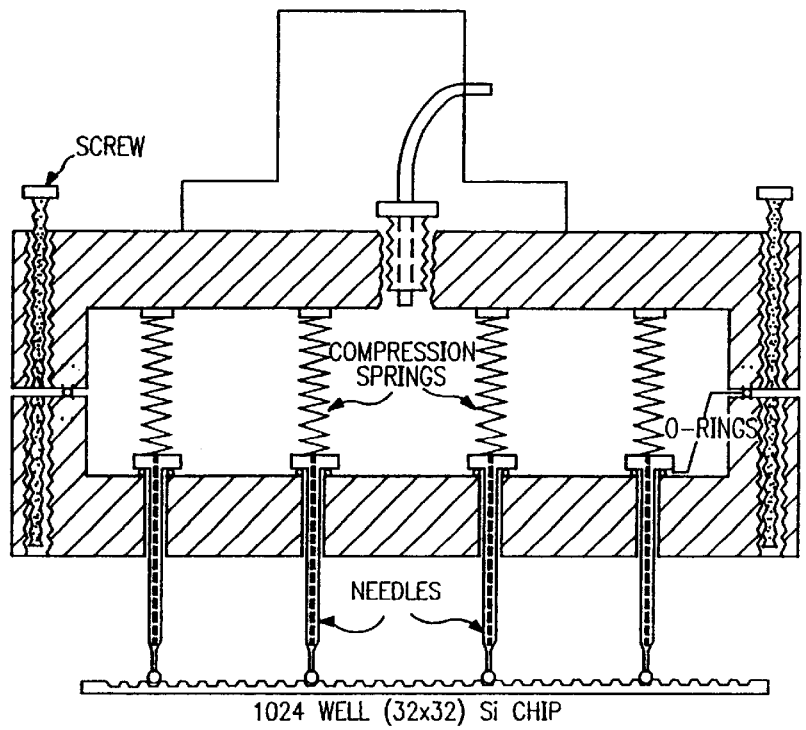
FIGS. 5A–5D depict a method for preparing an array of sample material.

In a first step, FIG. 5A, the program can direct the robotic assembly 16 to move the pin assembly 38 to be disposed above the source plate 20. The robotic assembly 16 will then dip the pin assembly into the source plate 20 which can be a 384 well DNA source plate. As shown in FIG. 4 the pin assembly can include 16 different pins such that the pin assembly 50 will dip 16 pins into different 16 wells of the 384 well DNA source plate 20. Next the data processor 12 will direct the motion controller 14 to operate the robotic assembly 16 to move the pin assembly to a position above the surface of the substrate 34. The substrate 34 can be any substrate suitable for receiving a sample of material and can be formed of silicon, plastic, metal, or any other such suitable material. Optionally the substrate will have a flat surface, but can alternatively include a pitted surface, a surface etched with wells or any other suitable surface typography. The program operating on data processor 12 can then direct the robotic assembly, through the motion controller 14, to direct the pressure controller 28 to generate a positive pressure within the interior chamber volume 58. In this practice, the positive interior pressure will force fluid from the holding chambers of vesicles 62 to eject fluid from the vesicles and into a respective well 92 of the substrate 90.

The program operating on data processor 12 can also direct the controller 14 to control the pressure controller 28 to control filling the holding chambers with source material from the source plate 20. The pressure controller 28 can generate a negative pressure within the interior chamber volume 58 of the pin assembly. This will cause fluid to be drawn up into the holding chambers of the vesicles 62A–62D. The pressure controller 28 can regulate the pressure either by open-loop or closed-loop control to avoid having fluid overdrawn through the holding chambers and spilled into the interior chamber volume 58. Loop control systems for controlling pressure are well known in the art and any suitable controller can be employed. Such spillage could cause cross-contamination, particularly if the source material drawn from the source plate 20 varies from well to well.

In an alternative embodiment, each of the holding chambers 64A–64D is sufficiently small to allow the chambers to be filled by capillary action. In such a practice, the pin assembly can consist of an array of narrow bore needles, such as stainless steel needles, that extend through the apertures of the lower block 54. The needles that are dipped into source solutions will be filled by capillary action. In one practice, the length of capillary which is to be filled at atmospheric pressure is determined approximately by:

$$H = \frac{2\gamma}{PGR}$$

where H equals Height, gamma equals surface tension, P equals solution density, G equals gravitational force and R equals needle radius. Thus the volume of fluid held by each vesicle can be controlled by selecting the dimensions of the interior bore. It is understood that at room temperature water will fill a 15 cm length of 100 $\mu$m radius capillary. Thus, a short bore nanoliter volume needle will fill to full capacity, but should not overflow because the capillary force is understood to be too small to form a meniscus at the top of the needle orifice. This prevents cross-contamination due to spillage. In one embodiment, the vesicles of the pin assembly can be provided with different sized interior chambers for holding and dispensing different volumes of fluid.

In an alternative practice, to decrease the volume of liquid that is drawn into the holding chambers of the vesicles, a small positive pressure can be provided within the interior chamber volume 58 by the pressure controller 28. The downward force created by the positive pressure can be used to counter the upward capillary force. In this way, the volume of fluid that is drawn by capillary force into the holding chambers of the vesicles can be controlled.

Figure 5B:
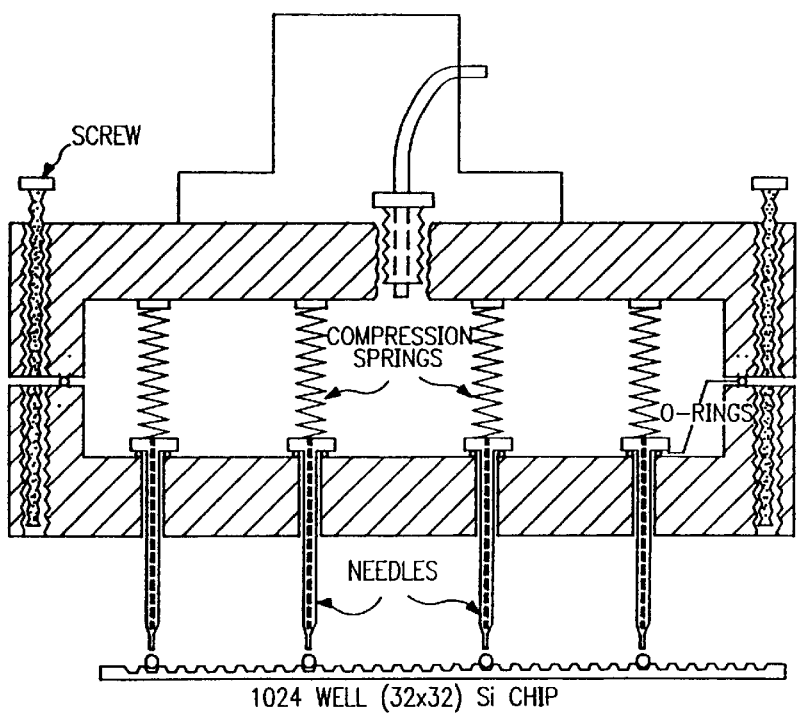

FIG. 5B shows that fluid within the holding chambers of the needle can be dispensed by a small positive pressure introduced through the central bore 88 extending through a swagelok 80. By regulating the pressure pulse that is introduced into the interior chamber volume 58, fluid can be ejected either as a spray or by droplet formation at the needle tip. It is understood that the rate of dispensing, droplet versus spray, depends in part upon the pressure applied by the pressure controller 28. In one practice, pressure is applied in the range of between 10 and 1,000 Torr of atmospheric pressure.

To this end the data processor 12 can run a computer program that controls and regulates the volume of fluid dispensed. The program can direct the controller 28 to eject a defined volume of fluid, either by generating a spray or by forming a drop that sits at the end of the vesicle, and can be contacted with the substrate surface for dispensing the fluid thereto.

Figure 5C:
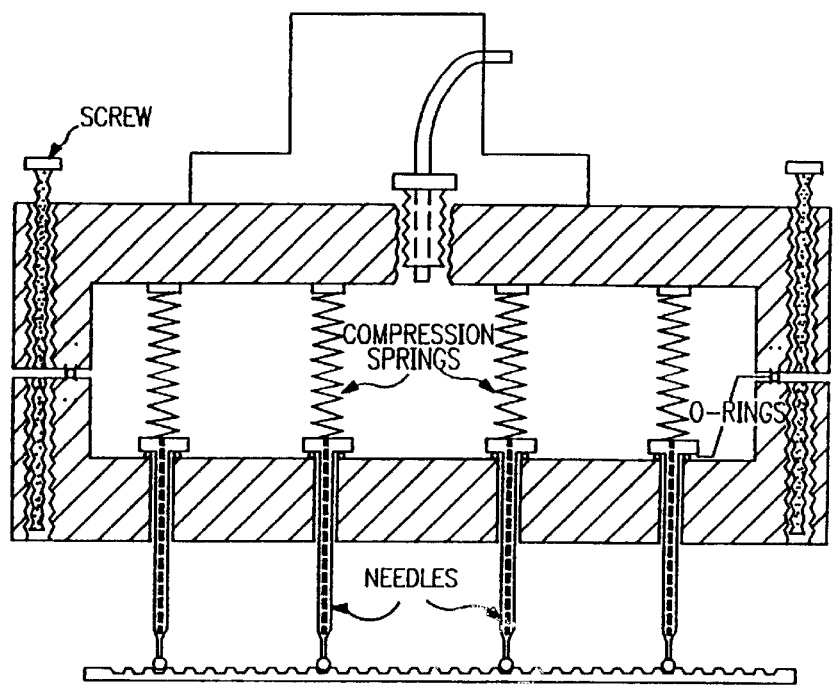
Figure 5D:
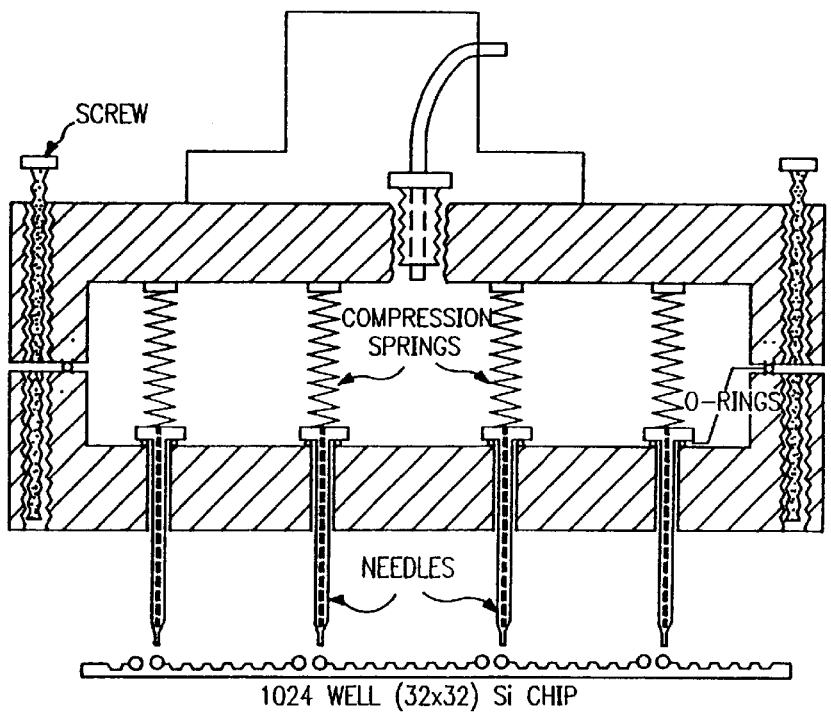

FIGS. 5C and 5D show the earlier steps shown in FIGS. 5A–5B can again be performed, this time at a position on the substrate surface that is offset from the earlier position. In the depicted process, the pin tool is offset by a distance equal to the distance between two wells 92. It will be apparent that other offset printing techniques can be employed without departing from the scope of the invention.

It will be understood that several advantages of the pin assembly depicted in FIG. 2 are achieved. For example, rinsing between dispensing events is straightforward, requiring only single or multiple pin fillings and emptying events with a rinse solution. Moreover, since all holding chambers fill to full capacity, the accuracy of the volumes dispensed varies only according to needle inner dimensions which can be carefully controlled during pin production. Further the device is cost effective, with the greatest expense attributed to the needles, however because no contact with a surface is required, the needles are exposed to little physical strain or stress, making replacement rare and providing long life.

Alternatively, deposition of sample material onto solid support surface can include techniques that employ pin tool assemblies that have solid pin elements extending from a block wherein a robotic assembly dips the solid pin elements of the pin assembly into a source of sample material to wet the distal ends of the pins with the sample materials. Subsequently the robotic assembly can move the pin assembly to a location above the substrate and then lower the pin assembly against the surface of the substrate to contact the individual wetted pins against the surface for spotting material of the substrate surface.

Figure 6A:
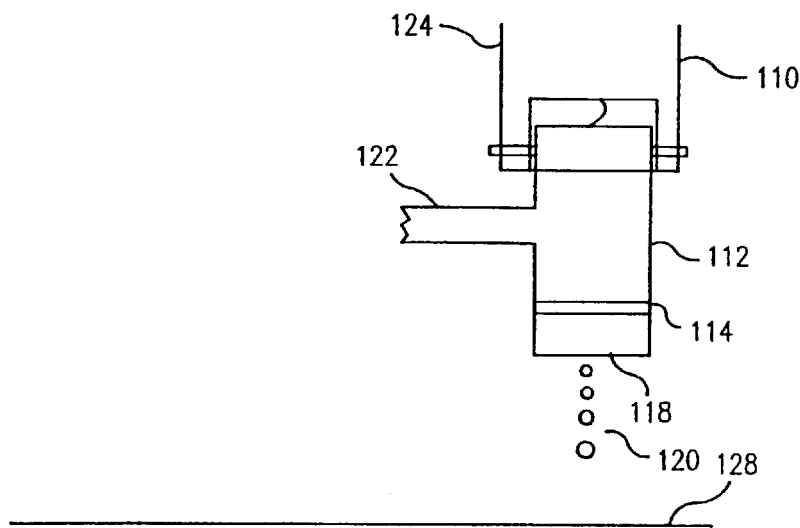
FIGS. 6A–6B depict an alternative assembly for dispensing material to the surface of a substrate.
Figure 6B:
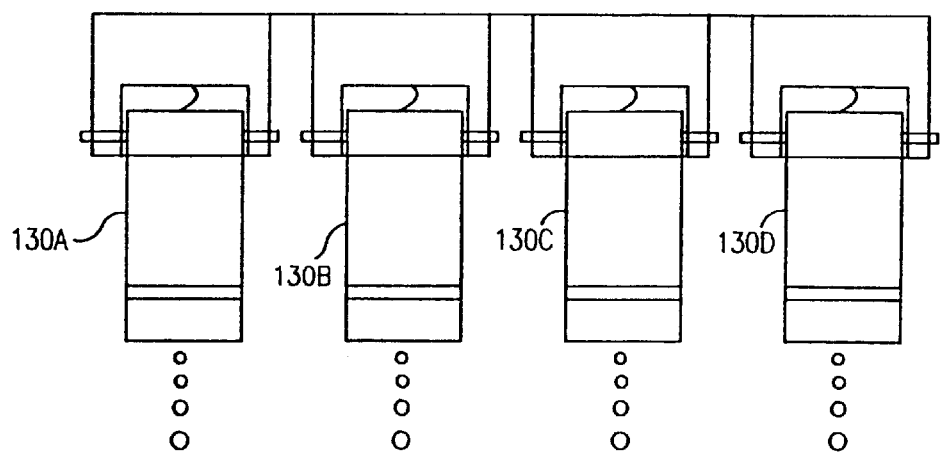

FIGS. 6A and 6B depict another alternative system for dispensing material on or to the surface of the substrate. In particular, FIG. 6A depicts a jet printing device 110 which includes a capillary element 112, a transducer element 114 and orifice (not shown) 118, a fluid conduit 122, and a mount 124 connecting to a robotic arm assembly, such as the robotic arm 24 depicted in FIG. 1. As further shown in FIG. 6A the jet assembly 110 is suitable for ejecting from the orifice 118 a series of drops 120 of a sample material for dispensing sample material onto the surface 128.

The capillary 112 of the jet assembly 110 can be a glass capillary, a plastic capillary, or any other suitable housing that can carry a fluid sample and that will allow the fluid sample to be ejected by the action of a transducer element, such as the transducer element 114. The transducer element 114 depicted in FIG. 6A is a piezo electric transducer element which forms around the parameter of the capillary 112 and can transform an electrical pulse received from the pulse generator within a robotic assembly 16 to cause fluid to eject from the orifice 118 of the capillary 112. One such jet assembly having a piezoelectric transducer element is manufactured by MicroFab Technology, Inc., of Germany. Any jet assembly, however, that is suitable for dispensing defined and controlled the volumes of fluid can be used herein including those that use piezoelectric transducers, electric transducers, electrorestrictive transducers, magnetorestrictive transducers, electromechanical transducers, or any other suitable transducer element. In the depicted embodiment, the capillary 112 has a fluid conduit 122 for receiving fluid material. In an optional embodiment, fluid can be drawn into the capillary by action of a vacuum pressure that will draw fluid through the orifice 118 when the orifice 118 is submerged in a source of fluid material. Other embodiments of the jet assembly 110 can be practiced with the invention without departing from the scope thereof.

FIG. 6B illustrates a further alternative assembly suitable for p being carried on the robotic arm of a robotic assembly, such as the assembly 16 depicted in FIG. 1. FIG. 6B illustrates four jet assemblies connected together, 130A–130D. Similar to the pin assembly in FIG. 2, the jet assembly depicted in FIG. 6B can be employed for the parallel dispensing of fluid material. It will be obvious to one of ordinary skill in the art of electrical engineering, that each of the jet assemblies 130A–130D can be operated independently of the others, for allowing the selective dispensing of fluid from select ones of the jet assemblies. Moreover, each of the jet assemblies 130A–130D can be independently controlled to select the volume of fluid that is dispensed from each respected one of the assembly 130A–130D. Other modifications and alterations can be made to the assembly depicted in FIG. 6B without departing from the scope of the invention.

Arrays can be formed on a substrate surface according to any of the techniques discussed above. The sample arrays are then analyzed by mass spectrometry to collect spectra data that is representative of the composition of the samples in the array. It is understood that the above methods provide processes that allow for rapidly dispensing definite and controlled volumes of analyte material. In particular these processes allow for dispensing sub to low nanoliter volumes of fluid. These low volume deposition techniques generate sample arrays well suited for analysis by mass spectrometry. For example, the low volumes yield reproducibility of spot characteristics, such as evaporation rates and reduced dependence on atmospheric conditions such as ambient temperature and light.

Continuing with the example shown in FIG. 5, the arrays can be prepared by loading oligonucleotides (0.1–50 ng/Ill) of different sequences or concentrations into the wells of a 96 well microtiter source plate 20; the first well can be reserved for holding a matrix solution. A substrate 34, such as a pitted silicon chip substrate, can be placed on the stage 26 of the robotics assembly 16 and can be aligned manually to orient the matrix of wells about a set of reference axes. The control program executing on the data processor 12 can receive the coordinates of the first well of the source plate 20. The robotic arm 12 can dip the pin assembly 38 into source plate 20 such that each of the 16 pins is dipped into one of the wells. Each vesicle can fill by capillary action so that the full volume of the holding chamber contains fluid. Optionally, the program executing on the data processor 12 can direct the pressure controller to fill the interior chamber 58 of the pin assembly 38 with a positive bias pressure that will counteract, in part, the force of the capillary action to limit or reduce the volume of fluid that is drawn into the holding chamber.

Optionally, the pin assembly 38 can be dipped into the same 16 wells of the source plate 20 and spotted on a second target substrate. This cycle can be repeated on as many target substrates as desired. Next the robotic arm 12 can dip the pin assembly 38 in a washing solution, and then dip the pin assembly into 16 different wells of the source plate 20, and spot onto the substrate target offset a distance from the initial set of 16 spots. Again this can be repeated for as many target substrates as desired. The entire cycle can be repeated to make a 2×2 array from each vesicle to produce an 8×8 array of spots (2×2 elements/vesicle×16 vesicles=64 total elements spotted). However, it will be apparent to anyone of ordinary skill in the art that process suitable for forming arrays can be practiced without departing from the scope thereof.

Oligonucleotides of different sequences or concentrations can be loaded into the wells of up to three different 384-well microtiter source plates; one set of 16 wells can be reserved for matrix solution. The wells of two plates are filled with washing solution. Five microtiter plates can be loaded onto the stage of the robotic assembly 16. A plurality of target substrates can be placed abutting an optional set of banking or registration pins disposed on the stage 26 and provided for aligning the target substrates along a set of reference axes. If the matrix and oligonucleotide are not pre-mixed, the pin assembly can be employed to first spot matrix solution on all desired target substrates. In a subsequent step the oligonucleotide solution can be spotted in the same pattern as the matrix material to re-dissolve the matrix. Alternatively, a sample array can be made by placing the oligonucleotide solution on the wafer first, followed by the matrix solution, or by pre-mixing the matrix and oligonucleotide solutions.

After depositing the sample arrays onto the surface of the substrate, the arrays can be analyzed using any of a variety of means (e.g., spectrometric techniques, such as UV/VIS, IR, fluorescence, chemiluminescence, NMR spectrometry or mass spectrometry. For example, subsequent to either dispensing process, sample loaded substrates can be placed onto a MALDI-TOF source plate and held there with a set of beveled screw mounted polycarbonate supports. In one practice, the plate can be transferred on the end of a probe to be held onto a 1μm resolution, 1" travel xy stage (Newport) in the source region of a time-of-flight mass spectrometer. It will be apparent to one of ordinary skill in the art that any suitable mass spectrometry tool can be employed with the present invention without departing from the scope thereof.

Preferred mass spectrometer formats for use with the arrays decsribed herein include ionization (I) techniques including but not limited to matrix assisted laser desorption (MALDI), continuous or pulsed electrospray (ESI) and related methods (e.g. Ionspray or Thermospray), or massive cluster impact (MCI); those ion sources can be matched with detection formats including linear or non-linear reflectron time-of-flight (TOF), single or multiple quadruple, single or multiple magnetic sector, Fourier Transform ion cyclotron resonance (FTICR), ion trap, and combinations thereof (e.g., ion-trap/time-of-flight). For ionization, numerous matrix/wavelength combinations (MALDI) or solvent combinations (ESI) can be employed. Subattomole levels of protein have been detected for example, using ESI (Valaskovic, G. A. et al., (1996) *Science* 273:1199–1202) or MALDI (Li, L. et al., (1996) *J. Am. Chem. Soc* 118:1662–1663) mass spectrometry.

Thus, it will be understood that in processes described herein a completely non-contact, high-pressure spray or partial-contact, low pressure droplet formation mode can be employed. In the latter, the only contact that will occur is between the droplet and the walls of the well or a hydrophilic flat surface of the substrate 34. In neither practice need there be any contact between the needle tip and the surface.

Preferred Embodiments

In one preferred embodiment, a double stranded nucleic acid sequence encoding a promoter sequence is isolated from a natural source e.g., bacteria, viruses, bacteriophages, plants or eukaryotic organisms) or assembled from synthetic sequences. A single stranded region of at least a 5 nucleotides at the 3'-end of the coding strand using standard methods known to those of skill in the art (e.g., see Sambrook et al., (1 989) Molecular Cloning, 2nd ed., Cold Spring Harbor Laboratory Press, New York). This single stranded region is designed such that it is complementary to a region of the nucleic acid to be sequenced or to an sequence shared between the two nucleic acid molecules (e.g., restriction endonuclease site).

The nucleic acid to be sequenced containing at least a partially single stranded 3'-end is hybridized according to the conditions described herein and known to those of skill in the art to the complementary sequences of the promoter-containing DNA. The nucleic acid to be sequenced may be single stranded or double stranded. The hybridization of the two nucleic acid molecules introduces one or more "nick" in the hybrid at the junction(s) of the adjacent nucleic acid molecules. Nicks in the coding or non-coding strand, preferably the coding strand, can be ligated by the addition of an appropriate nucleic acid ligase prior to initiating transcription. Methods for ligating nucleic acids are well known to those of skill in the art (e.g., see Sambrook et al., (1989) Molecular Cloning, 2nd ed., Cold Spring Harbor Laboratory Press, New York) and DNA and RNA ligases are commercially available (e.g., Boehringer Mannheim, Indianapolis, Ind.).

Transcription is initiated from the promoter by the addition of the appropriate RNA polymerase in the presence of ribonucleoside triphosphates under conditions described herein and known elsewhere (e.g., In *RNA Polymerase and the Regulation of Transcription,* Rezinkoff et al., eds, Elsevier, N.Y.). In preferred embodiments, a selected base-specific chain terminating 3'-deoxyribonucleoside triphosphate and the transcription mixture also contains inosine 5'-triphosphate to reduce the secondary structure of the RNA product or modified ribonucleoside triphosphates, such as 4-thio UTP, 5-bromo UTP or 5'-iodo CTP to facilitate turnover of the RNA polymerase enzyme and thereby increase the amount of RNA transcript available for analysis.

In other preferred embodiments, the method of sequencing may be used for diagnostic applications to determined the presence of genetic alterations in a known target nucleic acid. For example, a region of the target nucleic acid can be amplified using standard methods, such as PCR or other amplification methods known to those of skill in the art (e.g., see Sambrook et al., (1989) Molecular Cloning, 2nd ed., Cold Spring Harbor Laboratory Press, New York). The amplified nucleic acid can be denaturated and the strand to be sequenced, i.e., the noncoding strand, is isolated or may be used as a double stranded molecule.

Figure 7:
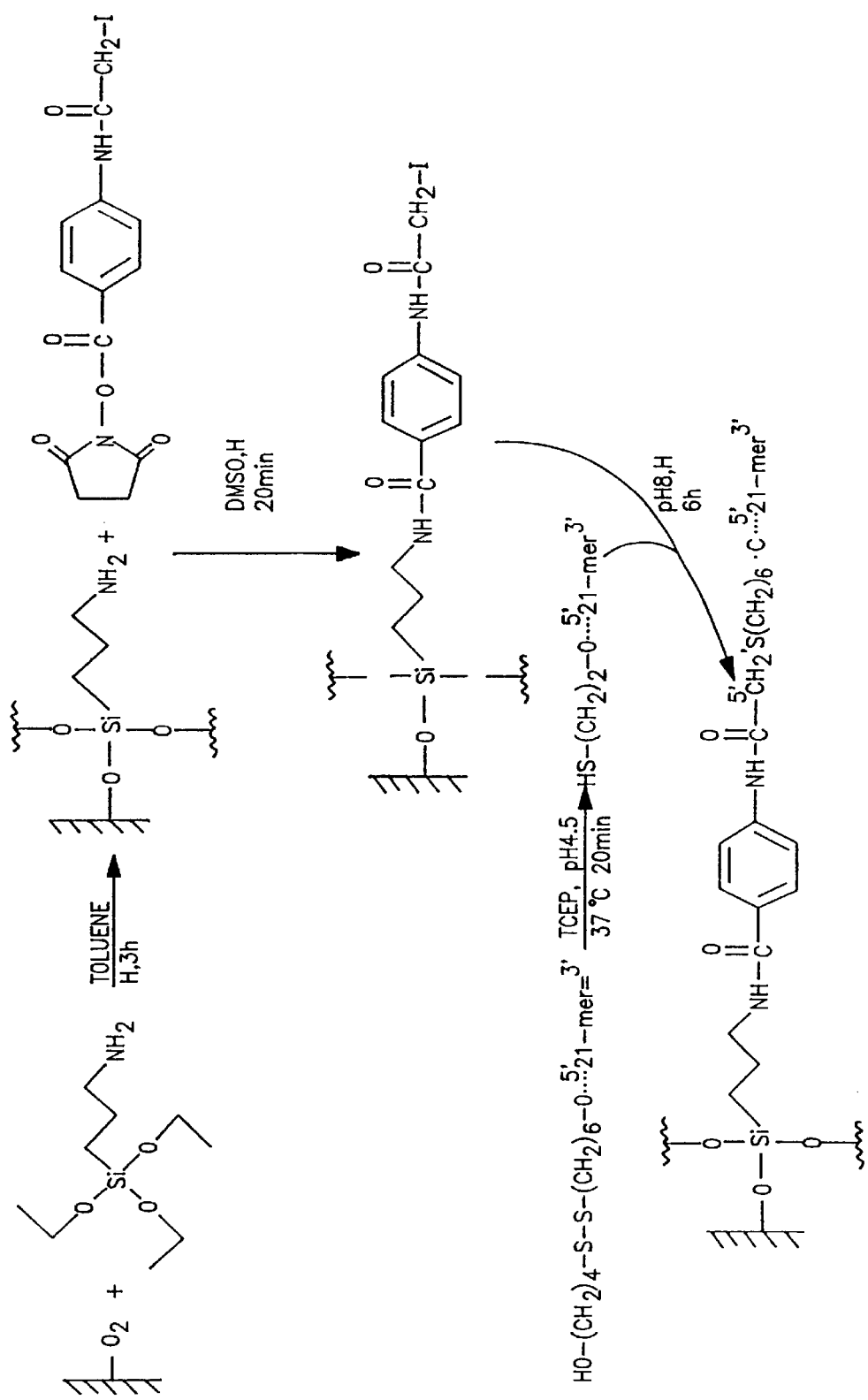
FIG. 7 is a schematic showing covalent attachment of oligodeoxynucleotides to a silicon dioxide surface as described in the methods herein. In particular, silicon dioxide was reacted with 3-minopropyltriethoxysilane to produce a uniform layer of primary amino groups on the surface. A heterobifunctional crosslinking agent was then reacted with the primary amine to incorporate an iodoacetamide-group. An oligodeoxynucleotide containing a 3'- or 5'-disulfide (shown as the 5') was treated with tris-(2-carboxyethyl) phosphine (TCEP) to reduce the disulfide to a free thiol, which was then coupled to the iodoacetamido-surface.

In preferred embodiments, the nucleic acid promoter-containing probe is covalently immobilized on a silica support by functionalization of the support with an amino functionality (e.g., by derivatization of the support with a reagent such as 3-aminopropyl-triethoxysilane (Aldrich Chemical Co., Milwaukee, Wis.); see FIG. 7). Other functionalized oxysilanes or orthosilicates can be used, and are commercially available (e.g., from Gelest, Inc., Tullytown, Pa.). For example, 3-mercaptopropyl-triethoxysilane can be used to functionalize a silicon surface with thiol groups. The amino-functionalized silica can then be reacted with a heterobifunctional reagent such as N-succinimidyl (4-iodacetyl) aminobenzoate (SIAB) (Pierce, Rockford, Ill.). Other homo- and hetero-bifunctional reagents which can be employed are available commercially, e.g., from Pierce. Finally, a nucleic acid functionalized with a thiol group (e.g., at the 5'-terminus) is covalently bound to the derivatived silica support by reaction of the thiol functionality of the nucleic acid molecule with the iodoacetyl functionality of the support.

In certain embodiments, the nucleic acid can be reacted with the cross-linking reagent to form a cross-linker/nucleic acid conjugate, which is then reacted with a functionalized support to provide an immobilized nucleic acid. Alternatively, the cross-linker can be combined with the nucleic acid and a functionalized solid support in one pot to provide substantially simultaneous reaction of the cross-linking reagent with the nucleic acid and the solid support. In this embodiment, it will generally be necessary to use a heterobifunctional cross-linker, i.e., a cross-linker with two different reactive functionalities capable of selective reaction with each of the nucleic acid and the functionalized solid support.

Following the methods described herein, spatially-addressable arrays of nucleic acids immobilized on insoluble supports that are suitable for sequencing of nucleic acids using RNA polymerase can be prepared. For example, the methods can be used to provide arrays of different nucleic acids immobilized on pins arranged in an array. In another embodiment, a photo-cleavable protecting group on the insoluble support can be selectively cleaved (e.g., by photolithography) to provide portions of a surface activated for immobilization of a nucleic acid. For example, a silicon surface, modified by treatment with 3-mercaptopropyl-triethoxysilane to provide thiol groups, can be blocked with a photocleavable protecting group (for examples of photo-cleavable protecting groups, see, e.g., PCT Publication WO 92/10092, or McCray et al., (1989) *Ann. Rev. Biophys. Biophys. Chem.* 18:239–270), and be selectively deblocked by irradiation of selected areas of the surface, e.g., by use of a photolithography mask. A nucleic acid promoter-containing probe modified to contain a thiol-reactive group can then be attached directly to the support, or, alternatively, a thiol-reactive cross-linking reagent can be reacted with the thiol-modified support, followed by (or substantially simultaneously with) reaction with a nucleic acid to provide immobilized nucleic acids. A nucleic acid base or sequence, once immobilized on a support according to the methods described herein, can be further modified according to known methods. for example, the nucleic acid sequence can be lengthened by performing solid-phase nucleic acid synthesis according to conventional techniques, including combinatorial technique.

Preferably the nucleic acids are covalently bound to a surface of the insoluble support through at least one sulfur atom, i.e., the nucleic acids are covalently bound to the surface through a linker moiety which includes at least one sulfur atom. Such covalently bound nucleic acids are readily produced by the methods described herein. In preferred embodiments, the covalently bound nucleic acids are a present on the surface of the insoluble support at a density of at least about 20 fmol/mm$^2$, more preferably at least about 75 fmol/mm$^2$, still more preferably at least about fmol/mm$^2$, yet more preferably at least about 100 fmol/mm$^2$, and most preferably at least about 150 fmol/mm$^2$.

The methods of sequencing nucleic acids described herein may be used for a variety of end use applications. For example, the methods may be used for diagnostic applications for the identification of mutations, such as transitions, transversions, deletions, insertions and the like. The methods may also be used to assist in the diagnosis of a number of genetic disorders, used for genetic screening or the determination of heredity or tissue or organ compatibility.

Methods of Identifying Transcriptional Terminator Sequences

Methods of identifying heretofore unknown transcriptional terminator and attenuator sequences are also provided. Transcriptional terminator sequences are responsible for the sequence specific cessation of RNA elongation and such terminator sequences from a variety of organisms have been reported. For example, bacterial rho-independent terminator sequences have two inverted repeats separate by several base pairs followed by a 5–10 nt polyT stretch. Upon transcription through these sequences, the resulting mRNA transcript forms a RNA hairpin stem-loop secondary structure behind the RNA polymerase molecule that increases pausing of RNA polymerase and/or destabilizes the RNA polymerase-DNA template interaction resulting in termination of the transcript within the DNA polyT stretch. (e.g., see Wilson and von Hippel (19; Reynolds et al. (1992a) *J. Mol. Biol.* 224:53–63; Reynolds et al. (1992b) *J. Mol. Biol.* 224:31–51; Telesnitsky et al. (1989) *Biochemistry* 28:5210–5218; d'Aubenton Carafa et al. (1990) *J. Mol. Biol.* 216:835–858).

Bacterial rho-dependent terminators lack the traditional inverted repeat stem-loop structure and further require additional factors, such as rho protein, to halt transcription (e.g., see Schmidt et al. (1984) *J. Mol. Biol.* 259:15000–15002). Rho-dependent termination is believed to result in the premature termination in bacterial species upon uncoupling of transcription and translation.

By modifying the standard transcription conditions described herein, transcriptional terminator sequences, e.g., rho-dependent and rho-independent terminators, may be identified using mass spectrometric methods. In practicing the methods, a single stranded region of the 3'-end of the nucleic acid to be sequenced is hybridized to a complementary sequence at the 3'-end of the coding strand a promoter-containing nucleic acid probe. In preferred embodiments, the promoter-containing nucleic acid is covalently coupled via the 5'-end of the noncoding strand or 3'-end of the coding strand to a solid support and, more preferably, is a 5'- or 3'-thiolated DNA linked at high densities to a aminosilane-treated solid support. The linkage may be in the absence or presence of a linker group and is preferably arranged in an array format.

Transcription is initiated in the absence or presence of modified RNA triphosphate analogs that increase the efficiency of RNA polymerase termination at such terminator sequences, such as 4-thio UTP, 5-bromo UTP or 5'-iodo CTP. The mass of the specifically terminated RNA transcripts can be detected by mass spectrometry where the observed mass of the RNA is indicative of the location of the terminator-dependent arrest of transcription. By comparing of the alignment of the sequence immediately preceding the site of transcriptional termination from several distinct genomic locations, heretofore unknown terminator sequences may be identified for different RNA polymerases.

In certain embodiments, nicks in one or more strand resulting from the hybridization of the nucleic acid to be sequenced may be ligated by the addition of an appropriate nucleic acid ligase prior to initiating transcription (i.e., adding a DNA or RNA ligase).

The present invention is further illustrated by the following Examples, which area intended merely to further illustrate and should not be construed as limiting. The entire contents of all the of the references (including literature references, issued patents, published patent applications, and co-pending patent applications) cited throughout this application are hereby expressly incorporated by reference.

EXAMPLE 1

High Density Attachment of Nucleic Acids to Silicon Wafers

Materials and Methods

All reagents, unless otherwise noted, were obtained from Aldrich Chemical, Milwaukee, Wis.

Silicon Surface Preparation

Silicon wafers were washed with ethanol, flamed over bunsen burner, and immersed in an anhydrous solution of 25% (by volume) 3-aminopropyltriethoxysilane in toluene for 3 hours. The silane solution was then removed, and the wafers were washed three times with toluene and three times with dimethyl sulfoxide (DMSO). The wafers were then incubated in a 10 mM anhydrous solution of N-succinimidyl (4-iodoacetyl) aminobenzoate (SIAB) (Pierce Chemical, Rockford, Ill.) in anhydrous DMSO. Following the reaction, the SIAB solution was removed, and the wafers were washed three times with DMSO.

Since it was impossible to monitor the condensation of SIAB and the amino group while on the solid support of the wafer, the reaction was performed in solution to determine the optimal reaction time. Thin layer chromatography (TLC) (glass backed silica plates with a 254 nm fluorescent indicator) (Baker, Phillipsburg, NF) was employed using 95:5 chloroform:methanol (Baker, Phillipsburg, N.J.) which enabled separation of the two starting materials. It was possible to visualize the SIAB starting material under long wave ultraviolet light (302 nm); 3-aminopropyltriethoxysilane was not active under ultraviolet light, therefore, the plate was sprayed with a solution of ninhydrin which reacts with primary amines to reveal a purple spot upon heating. A microscale reaction was run in chloroform/DMSO using a slight molar excess of SIAB in comparison to 3-aminopropyltriethoxysilane and monitored with the above mentioned TLC conditions.

Oligonucleotide Modifications

Reduction of the disulfide from 3'- or 5'-disulfide-containing oligodeoxynucleotides (Operon Technologies, Alameda, Calif. or Oligo Etc., Wilsonville, Oreg.) was monitored using reverse-phase FPLC (Pharmacia, Piscataway, N.J.); a shift can be seen in the retention time of the oligodeoxynucleotide upon cleavage of the disulfide. Various reduction methods were investigated to determine the optimal conditions. In one case, the disulfide-containing oligodeoxynucleotide (31.5 nmol, 0.5 mM) was incubated with dithiothreitol (DTT) (Pierce Chemical, Rockford, Ill.) (6.2 mmol, 100 mM) as pH 8.0 and 37° C. With the cleavage reaction essentially complete, the free thiol-containing oligodeoxynucleotide was isolated using a Chromaspin-10 column (Clontech, Palo Alto, Calif.) since DTT may compete in the subsequent reaction. Alternatively, tris-(2-carboxyethyl) phosphine (TCEP) (Pierce Chemical, Rockford, Ill.) has been used to cleave the disulfide. The disulfide-containing oligodeoxynucleotide (7.2 nmol, 0.36 mM) was incubated with TCEP in pH 4.5 buffer at 37° C. It is not necessary to isolate the product following the reaction since TCEP does not competitively react with the iodoacetamido functionality. Varying concentrations of TCEP were used for the cleavage reaction to determine the optimal conditions for the conjugation reaction.

Probe Coupling

To each wafer which had been derivatized to contain the iodoacetamido functionality as described above was added a 10 mM aqueous solution of the free-thiol containing oligodeoxynucleotide in 100 mM phosphate buffer, pH 8; the reaction was allowed to proceed for a minimum of five hours at room temperature in 100% relative humidity. Following the reaction, the oligodeoxynucleotide solution was removed, and the wafers were washed two times in 5 X SSC buffer (75 mM sodium citrate, 750 mM sodium chloride, pH 7) with 50% formamide (USB, Cleveland, Ohio) at 65° C. for 1 hour each.

Radiochemical Determination of Probe Density

In order to determine the amount of DNA covalently attached to a surface or the amount of a complementary sequence hybridized, radiolabeled probes were employed. In cases where a 5'-disulfide-containing oligodeoxynucleotide was to be immobilized, the 3'-terminus was radiolabeled using terminal transferase enzyme and a radiolabeled dideoxynucleoside triphosphate; in a standard reaction, 15 pmol (0.6 $\mu$M) of the 5'-disulfide-containing oligodeoxynucleotide was incubated with 50 $\mu$Ci (16.5 pmol, 0.66 $\mu$M) of ($\alpha$-$^{32}$P) dideoxyadenosine-5'triphosphate (ddATP) (Amersham, Arlington Height, Ill.) in the presence of 0.2 mM 2-mercaptoethanol. Upon the addition of 40 units of the terminal deoxynucleotidyl transferase enzyme (USB, Cleveland, Ohio), the reaction was allowed to proceed for one hour at 37° C. After this time, the reaction was stopped by immersion of the vial in 75° C. water bath for ten minutes, and the product was isolated using a Chromaspin-10 column (Clontech, Palo Alto, Calif.). Similarly, a 5'-disulfide-containing oligodeoxynucleotide was radiolabeled with $^{35}$S.

In cases where a 3'-disulfide-containing oligodeoxynucleotide was to be immobilized, the 5'-terminus was radiolabeled using T4 polynucleotide kinase and a radiolabeled nucleoside triphosphate. For example, 15 pmol (0.6 µM) of the 3'-disulfide-containing oligodeoxynucleotide was incubated with 50 µCi (16.5 pmol, 0.66 µM) of ($\lambda^{32}$P) adenosine-5'triphosphate (ATP) (Amersham, Arlington Height, Ill.) in the presence of 50 mM Tris-HCl, pH 7.6, 10 mM $MgCl_2$, 10 mM 2-mercaptoethanol. Following the addition of 40 units of T4 polynucleotide kinase, the reaction was allowed to proceed for 1 hour at 37° C. The reaction was stopped by immersion of the vial in a 75° C. water bath for ten minutes; the product was then isolated using a Chromaspin-10 column (Clontech, Palo Alto, Calif.).

To determine the density of covalently immobilized probe, the disulfide-containing oligodeoxynucleotide of choice was added to a trace amount of the same species than had been radiolabeled as described above. The disulfide was cleaved, the probe was immobilized on iodoacetamido-functionalized wafers, the wafers were washed, and then exposed to a phosphorimager screen (Molecular Dynamics, Sunnyvale, Calif.). For each different oligodeoxynucleotide utilized, reference spots were made on polystyrene in which the molar amount of oligodeoxynucleotide was known; these reference spots were exposed to the phosphorimager screen as well. Upon scanning the screen, the quantity (in moles) of oligodeoxynucleotide bound to each chip was determined by comparing the counts to the specific activities of the references.

Hybridization and Efficiency

To a wafer that had been functionalized with an immobilized probe was added a solution of a complementary sequence (10 µM) in 1M NaCl and TE buffer. The wafer and solution were heated to 75° C. and allowed to cool to room temperature over 3 hours. After this time, the solution was removed, and the wafer was washed two times with TE buffer.

To determine the amount of oligonucleotide hybridized, immobilization of the probe was first carried out as described above except that the probe was labeled with $^{35}$S rather than $^{32}$P. The density of immobilized probe was determined with the phosphorimager. Next, the same wafer was incubated in TE buffer, 1M NaCl, and its complementary strand (10 µM) which had been radiolabeled with $^{32}$P. Hybridization was carried out as previously described. Following a wash to remove non-specific binding, the wafer and reference were exposed to a phosphorimager screen with a piece of copper foil between the screen and the wafer. The copper foil serves to block the signal from $^{35}$S, while allowing the $^{32}$P signal to pass freely. The molar amount of hybridized oligonucleotide is then determined, thus revealing the percent of covalently immobilized probe that is available for hybridization.

MALDI-TOF Mass Spectrometric Analysis

As described above, wafers containing non-radiolabeled immobilized oligodeoxynucleotide (name: TCUC; sequence: GAATTCGAGCTCGGTACCCGG; molecular weight; 6455Da; SEQ ID NO. 1) were synthesized, and a complementary sequence (name: MJM6; sequence: CCGGGTACCGAGCTCGAATTC; molecular weight: 6415Da; SEQ ID NO. 2) was hybridized. The wafers were washed in 50 mM ammonium citrate buffer for cation exchange to remove sodium and potassium ions on the DNA backbone (Pieles, U. et al., (1993) Nucl. Acids Res., 21:3191–3196). A matrix solution of 3-hydroxypicolinic acid (3-HPA, 0.7 M in 50% acetonitrile, 10% ammonium citrate; Wu, K. J., et al. (1993) Rapid Commun. Mass Spectrom., 7:142–146) was spotted onto the wafer and allowed to dry at ambient temperature. The wafers were attached directly to the sample probe of a Finnigan MAT (Bremen, Germany) Vision 2000 reflectron TOF mass spectrometer using a conducting tape. The reflectron possesses a 5 keV ion source and 20 keV post-acceleration; a nitrogen laser was employed; and all spectra were taken in the positive ion mode.

Results

Surface Chemistry

Employing standard silicon dioxide modification chemistry, a silicon wafer was reacted with 3-aminopropyltriethoxysilane to produce a uniform layer of primary amino groups on the surface. As shown in FIG. 7, the surface was then exposed to a heterobifunctional crosslinker resulting in iodoacetamido groups on the surface. It was possible to determine the optimal reaction time of this reaction in solution using TLC. The SIAB crosslinker was visualized under long wave ultraviolet light (302 nm) to reveal a spot with an $R_f$ value of 0.58. 3-aminopropyltriethoxysilane was not active under ultraviolet light, therefore, ninhydrin was used to reveal a purple spot indicating the presence of a primary amine at the baseline. A microscale reaction was run using a slight molar excess of SIAB in comparison to 3-aminopropyltriethoxysilane; TLC analysis after approximately one minute revealed a new spot visible under long wave ultraviolet light with an $R_f$ value of 0.28. There was no evidence of a purple spot upon spraying with ninhydrin, thus all the 3-aminopropyltriethoxysilane starting material had been consumed in the reaction. UV light also revealed the excess SIAB which remained following the reaction. From these results, it was determined the reaction is complete after approximately one minute. In all cases, the iodoacetamido-functionalized wafers were used immediately to minimize hydrolysis of the labile iodoacetamido-functionality. Additionally, all further wafer manipulations were performed in the dark since the iodoacetamido-functionality is light sensitive.

Disulfide reduction of the modified oligonucleotide was monitored by observing a shift in retention time on reverse-phase FPLC. It was determined that after five hours in the presence of DTT (100 mM) or TCEP (10 mM), the disulfide was fully reduced to a free thiol. If the DTT reaction was allowed to proceed for a longer time, an oligonucleotide dimer formed in which pairs of free thiols had reacted. Such dimerization was also observed when the DTT was removed following the completion of the cleavage reaction. This dimerization was not observed when TCEP was employed as the cleavage reagent since this reaction is performed at pH 4.5, thus the free thiols were fully protonated inhibiting dimerization.

Figure 8:
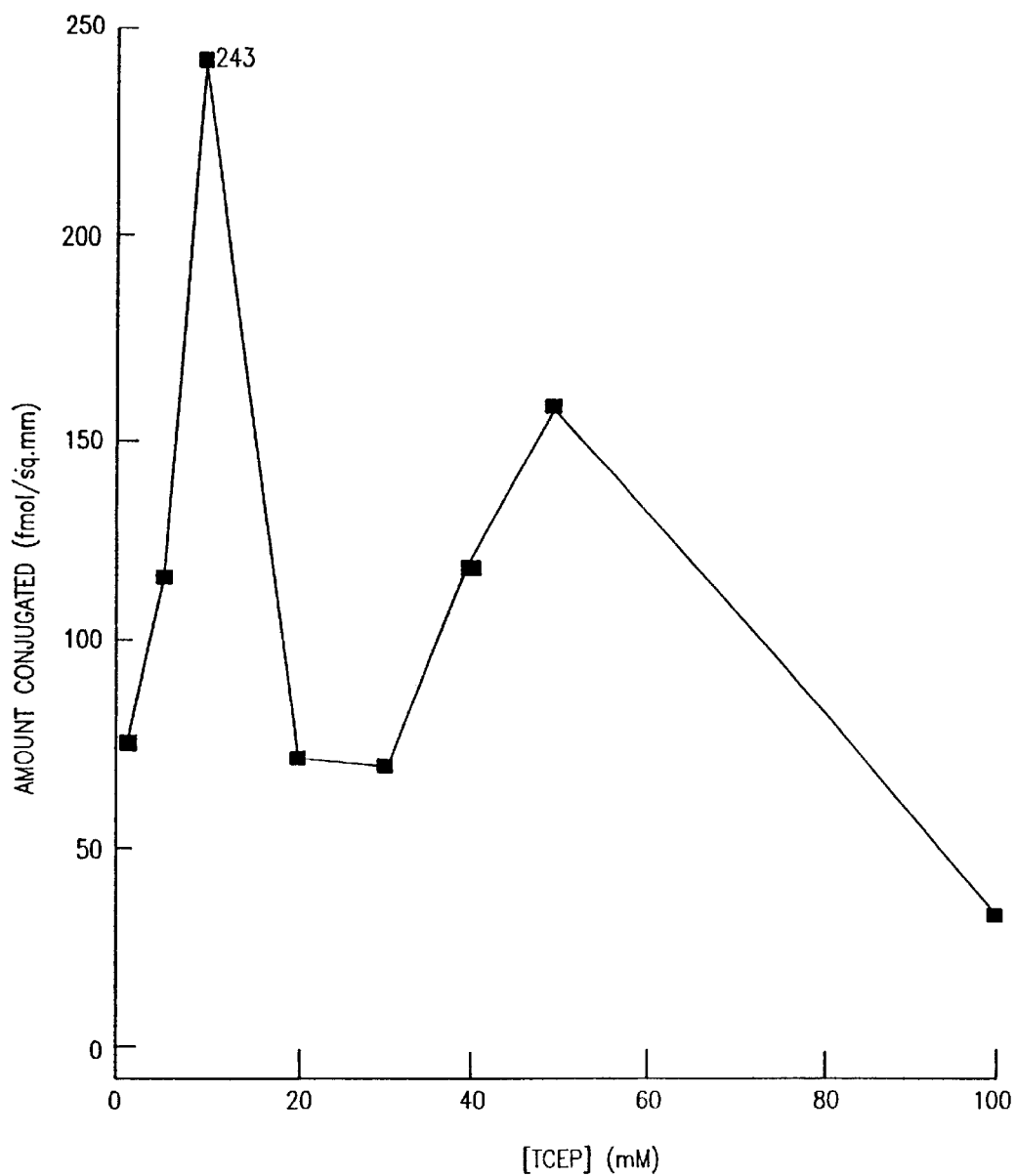
FIG. 8 is a graph which plots conjugation of oligodeoxynucleotide probes to a silicon surface as a function of TCEP concentration used in the disulfide reduction.

Immediately following disulfide cleavage, the modified oligonucleotide was incubated with the iodacetamido-functionalized wafers. To ensure complete thiol deprotonation, the coupling reaction was performed at pH 8.0. The probe surface density achieved by this chemistry of silicon wafers was analyzed using radiolabeled probes and a phosphorimager. The probe surface density was also monitored as a function of the TCEP concentration used in the disulfide cleavage reaction (FIG. 8). Using 10 mM TCEP to cleave the disulfide and the other reaction conditions described above, it was possible to reproducibly yield a surface density of 250 fmol per square mm of surface. Identical experiments as described above were performed except that the oligonucleotide probe lacked a thiol modification; surface densities of less than 5 fmol per square mm of surface proved that non-specific binding is minimal and that probe coupling most likely occurred as proposed in FIG. 7.

Hybridization

After attaching $^{35}$S-labeled probes to the surface of wafers and determining conjugation density as described above, hybridization of $^{32}$P-labeled oligonucleotides was carried out; hybridization efficiency and density were determined using the phosphorimager and copper foil. It was determined experimentally that copper foil blocks 98.4% of an $^{35}$S signal, while fully allowing a $^{32}$P signal to be detected. The complementary sequence reproducibly hybridized to yield 105 fmol per square mm of surface; this corresponds to approximately 40% of the conjugated probes available for hybridization. Similarly, a non-complementary sequence was employed in this scheme yielding less than 5 fmol per square mm of surface in non-specific binding.

It is hypothesized that stearic interference between the tightly packed oligonucleotide on the flat surface inhibits hybridization efficiencies higher that 40%. With this in mind, a spacer molecule was incorporated between the terminus of the hybridizing region of the oligonucleotide and the support. The chosen spacers were a series of poly dT sequences ranging in length from 3 to 25. Upon examination of these samples with radiolabels and the phosphorimager, it was determined that 40% was still the maximum hybridization that could be achieved.

MALDI-TOF MS Analysis

Figure 9:
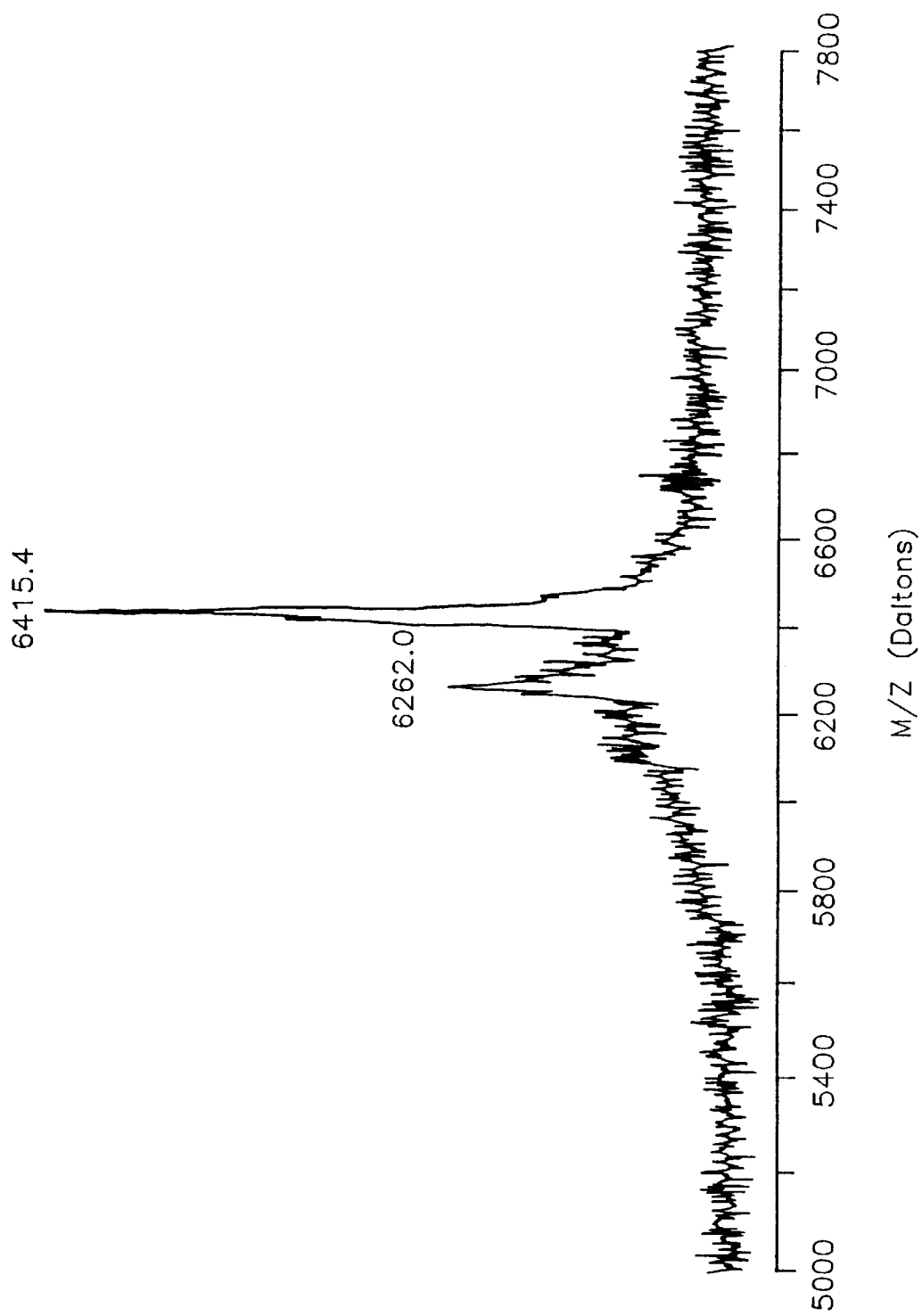
FIG. 9 is a matrix assisted laser desorbtion/ionization-time-of-flight (MALDI-TOF) mass spectrum of a silicon wafer with the oligodeoxynucleotide sequence denoted "TCUC" (5'-GAATTCGAGCTCGGTACCCGG-3'; SEQ ID NO: 1) covalently bound essentially as described in FIG. 7 and the oligodeoxynucleotide sequence denoted "MJM6" (5'-CCGGGTACCGAGCTCGAATTC-3'; SEQ ID NO: 2) hybridized thereto.

Wafers were functionalized with probes, complementary sequences were hybridized, and the samples were analyzed under standard MALDI conditions as described above. Analysis revealed that only the annealed strand (MJM6) was observed in the mass spectrum with an experimental mass-to-charge ratio of 6415.4; the theoretical mass-to-charge ratio is 6415 (FIG. 9). Since there was no signal at a mass-to-charge ratio of 6455, it was determined that the wafer-conjugated strand (TCUC) was not desorbed thus the iodoacetamido linkage was stable enough to withstand the laser and remain intact. There was an additional signal observed at a mass-to-charge ration of 6262.0. This signal results from a depurination of guanosines since it is known that DNA is susceptible to the loss of purine bases during the MALDI process, (Nordoff, E., et al., (1992) *Rapid Commun. Mass Spectrom.* 6:771–776). The sample crystals on the wafer were not homogeneously distributed, thus it was necessary to hunt for a good spot . Because of this non-homogeneity, the mass resolution varied, but it generally ranged from 200–300 for the desorbed oligonucleotide in the mass spectra. In one set of experiments, non-complementary sequences were hybridized to the wafer; following a wash as previously described, analysis by MALDI-TOF MS revealed that minimal non-specific annealing had taken place since no signal was detected.

EXAMPLE 2

Preparation of DNA Arrays Using Serial and Parallel Dispensing Tools

Robot-driven serial and parallel pL-nL dispensing tools were used to generate 10–10$^3$ element DNA arrays on <1" square chips with flat or geometrically altered (e.g. with wells) surfaces for matrix assisted laser desorption ionization mass spectrometry analysis. In the former, a 'piezoelectric pipette' (70 μm id capillary) dispenses single or multiple ~0.2 nL droplets of matrix, and then analyte, onto the chip; spectra from as low as 0.2 fmol of a 36-mer DNA have been acquired using this procedure. Despite the fast (<5 sec) evaporation, micro-crystals of 3-hydroxypicolinic acid matrix containing the analyte are routinely produced resulting in higher reproducibility than routinely obtained with larger volume preparations; all of 100 five fmol spots of a 23-mer in 800 μm wells yielded easily interpreted mass spectra, with 99/100 parent ion signals having signal to noise ratio of >5. In a second approach, probes from 384 well microtiter plate are dispensed 16 at a time into chip wells or onto flat surfaces using an array of spring loaded pins which transfer ~20 nL to the chip by surface contact; MS analysis of array elements deposited with the parallel method are comparable in terms of sensitivity and resolution to those made with the serial method.

Description of the Piezoelectric Serial Dispenser

The experimental system developed from a system purchased from Microdrop GmbH, Norderstedt Germany and can include a piezoelectric element driver which sends a pulsed signal to a piezoelectric element bonded to and surrounding a glass capillary which holds the solution to be dispensed; a pressure transducer to load (by negative pressure) or empty (by positive pressure) the capillary; a robotic xyz stage and robot driver to maneuver the capillary for loading, unloading, dispensing, and cleaning, a stroboscope and driver pulsed at the frequency of the piezo element to enable viewing of 'suspended' droplet characteristics; separate stages for source and designation plates or sample targets (i.e. Si chip); a camera mounted to the robotic arm to view loading to designation plate; and a data station which controls the pressure unit, xyz robot, and piezoelectric river.

Description of the Parallel Dispenser

The robotic pintool consists of 16 probes housed in a probe block and mounted on an X Y, Z robotic stage. The robotic stage was a gantry system which enables the placement of sample trays below the arms of the robot. The gantry unit itself is composed of X and Y arms which move 250 and 400 mm, respectively, guided by brushless linear servo motors with positional feedback provided by linear optical encoders. A lead screw driven Z axis (50 mm vertical travel) is mounted to the xy axis slide of the gantry unit and is controlled by an in-line rotary servo motor with positional feedback by a motor-mounted rotary optical encoder. The work area of the system is equipped with a slide-out tooling plate that holds five microtiter plates (most often, 2 plates of wash solution and 3 plates of sample for a maximum of 1152 different oligonucleotide solutions) and up to ten 20×20 mm wafers. The wafers are placed precisely in the plate against two banking pins and held secure by vacuum. The entire system is enclosed in plexi-glass housing for safety and mounted onto a steel support frame for thermal and vibrational damping. Motion control is accomplished by employing a commercial motion controller which was a 3-axis servo controller and is integrated to a computer; programming code for specific applications is written as needed.

Samples were dispensed with the serial system onto several surfaces which served as targets in the MALDI TOF analysis including (1) A flat stainless steel sample target as supplied for routine use in a Thermo Bioanalysis Vision 2000; (2) the same design stainless steel target with micromachined nanopits; (3) flat silicon (Si) wafers; (4) polished flat Si wafers; (5) Si wafers with rough (3–6 pLm features) pits; (6)(a) 12×12 or ((b) 18×18) mm Si chips with (a) 10×10 (or (b) 16×16) arrays of chemically etched wells, each 800×8001 lm on a side with depths ranging from 99–400 (or(b) 120) micrometer, pitch (a) 1.0 (or(b) 1.125) mm; (7) 15×15 mm Si chips with 28×28 arrays of chemically etched wells, each 450×450 micrometer on a side with depths ranging from 48–300 micrometer, pitch 0.5 mm; (8) flat polycarbonate or other plastics; (9) gold and other metals; (10) membranes; (11) plastic surfaces sputtered with gold or other conducting materials. The dispensed volume is controlled from $10^{-10}$ to $10^{-6}$ L by adjusting the number of droplets dispensed.

Sample Preparation and Dispensing

1. Serial

Oligonucleotides (0.1–50 ng/microliter of different sequence or concentrations were loaded into wells of a 96 well microtiter plate; the first well was reserved for matrix solution. A pitted chip (target 6a in MALDI targets' section) was placed on the stage and aligned manually. Into the (Windows-based) robot control software were entered the coordinates of the first well, the array size (ie number of spots in x and y) and spacing between elements, and the number of 0.2 nL drops per array element. The capillary was filled with ~10 microL rinse $H_2O$, automatically moved in view of a strobe light-illuminated camera for checking tip integrity and cleanliness while in continuous pulse mode, and emptied. The capillary was then filled with matrix solution, again checked at the stroboscope, and then used to spot an array onto flat or pitted surfaces. For reproducibilty studies in different MS modes, typically a 10×10 array of 0.2–20 nL droplets were dispensed. The capillary was emptied by application of positive pressure, optionally rinsed with $H_2O$, and led to the source oligo plate where ~5 $\mu$L of 0.05–2.0 $\mu$M synthetic oligo were drawn. The capillary was then rastered in series over each of the matrix spots with 0.2–20 nL aqueous solution added to each.

2. Parallel

Parallel Programs were written to control array making by offset printing; to make an array of 64 elements on 10 wafers, for example, the tool was dipped into 16 wells of a 3 84 well DNA source plate, moved to the target (e.g. Si, plastic, metal), and the sample spotted by surface contact. The tool was then dipped into the same 16 wells and spotted on the second target; this cycle was repeated on all ten wafers. Next the tool was dipped in washing solution, then dipped into 16 different wells of the source plate, and spotted onto the target 2.25 mm offset from the initial set of 16 spots; again this was repeated on all 10 wafers; the entire cycle was repeated to make a 2×2 array from each pin to produce an 8×8 array of spots (2×2 elements/pin×16 pins=64 total elements spotted).

To make arrays for MS analysis, oligonucleotides of different sequences or concentrations were loaded into the wells of up to three different 384-well microtiter plates, one set of 16 wells was reserved for matrix solution. The wells of two plates were filled with washing solution. The five microtiter plates were loaded onto the slide-out tooling plate. Ten wafers were placed abutting the banking pins on the tooling plate, and the vacuum turned on. In cases where matrix and oligonucleotide were not pre-mixed, the pintool was used to spot matrix solution first on all desired array elements of the ten wafers. For this example, a 16×16 array was created, thus the tool must spot each of the ten wafers 16 times, with an offset of 1.125 mm. Next, the oligonucleotide solution was spotted in the same pattern to re-dissolve the matrix. Similarly, an array could be made by placing the oligonucleotide solution on the wafer first, followed by the matrix solution, or by pre-mixing the matrix and oligonucleotide solutions.

Mass Spectrometry

Subsequent to either dispensing scheme, loaded chips were held onto a MALDI-TOF source plate with a set of beveled screw mounted polycarbonated supports. The plate was transferred on the end of a probe to be held onto a 1 $\mu$m resolution, 1" travel xy stage (Newport) in the source region of a time-of-flight mass spectrometer. The instrument, normally operated with 18–26 kV extraction, could be operated in linear or curved field reflectron mode, and in continuous or delayed extraction mode.

RESULTS

Serial Dispensing with the Piezoelectric Pipette

While delivery of a saturated 3HPA solution can result in tip clogging as the solvent at the capillary-air interface evaporates, pre-mixing DNA and matrix sufficiently dilutes the matrix such that it remains in solution while stable sprays which could be maintained until the capillary was emptied were obtained; with 1:1 diluted (in $H_2O$) matrix solution, continuous spraying for >>10 minutes was possible. Turning off the piezo element so that the capillary sat inactive for >5 minutes, and reactivating the piezo element also did not result in a clogged capillary.

Initial experiments using stainless steel sample targets as provided by Finnigan Vision 2000 MALDI-TOF system run in reflectron mode utilized a pre-mixed solution of the matrix and DNA prior to dispensing onto the sample target. In a single microtiter well, 50 $\mu$L saturated matrix solution, 25 $\mu$L of a 51 $\mu$L solution of the 12-mer (ATCG)3 (SEQ ID No. 3), and 25 $\mu$L of a 51 $\mu$L solution of the 28-mer (ATCG)7 (SEQ ID No. 4) were mixed. A set of 10×10 arrays of 0.6 $\mu$L drops was dispensed directly onto a Finnigan Vision 2000 sample target disk; MALDI-TOF mass spectrum was obtained from a single array element which contained 750 attomoles of each of the two oligonucleotides. Interpretable mass spectra has been obtained for DNAs as large as a 53-mer (350 amol loaded, not shown) using this method.

Figure 10:
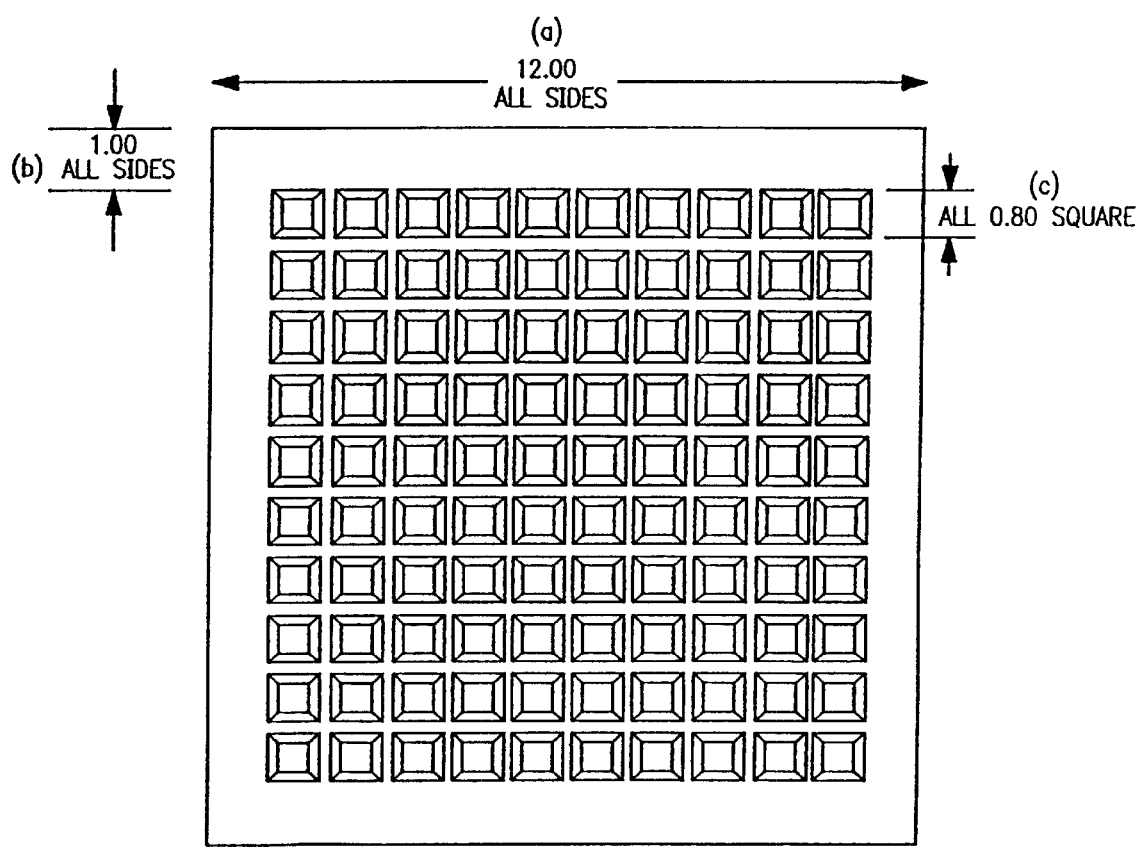
FIG. 10 depicts one embodiment of a substrate having wells etched therein that are suitable for receiving material for analysis.

Mass spectra were also obtained from DNAs microdispensed into the wells of a silicon chip. FIG. 10 shows a 12×12 mm silicon chip with 100 chemically etched wells; mask dimensions and etch time were set such that fustum (i.e., inverted flat top pyramidal) geometry wells with 800× 800 $\mu$m (top surface) and 100 $\mu$m depth were obtained. Optionally, the wells can be roughed or pitted. As described above, the chip edge was aligned against a raised surface on the stage to define the x and y coordinate systems with respect to the capillary. (Alternatives include optical alignment, artificial intelligence pattern recognition routines, and dowel-pin based manual alignment). Into each well was dispensed 20 droplets (~5 nL) of 3-HPA matrix solution without analyte; for the 50% $CH_3CN$ solution employed, evaporation times for each droplet were on the order of 5–10 seconds. Upon solvent evaporation, each microdispensed matrix droplet as viewed under a 120X stereomicroscope generally appeared as an amorphous and 'milky' flat disk; such appearances are consistent with those of droplets from which the FIG. 3b spectrum was obtained. Upon tip emptying, rinsing, and refilling with a 1.4 μm aqueous solution of a 23-mer DNA ($M_r$(calc)=6967 Da), the capillary was directed above each of the 100 spots of matrix where 5 nL of the aqueous DNA solution was dispensed directly on top of the matrix droplets. Employing visualization via a CCD camera, it appeared that the aqueous analyte solution mixed with and re-dissolved the matrix (complete evaporation took ~10 sec at ambient temperature and humidity). The amorphous matrix surfaces were converted to true micro-crystalline surfaces, with crystalline features on the order of <1 μm.

Figure 11:
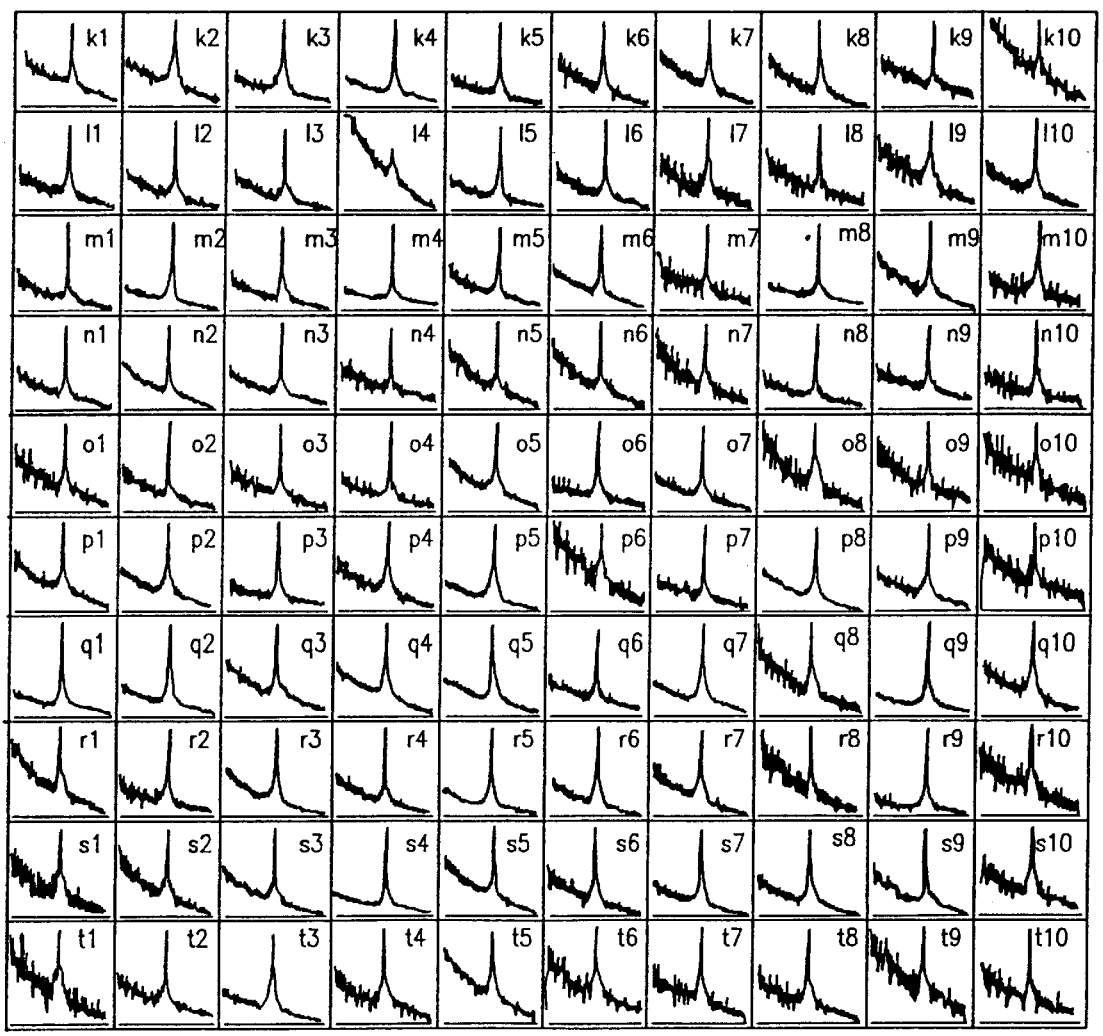
FIG. 11 depicts one example of spectra obtained from a linear time of flight mass spectrometer instrument and representative of the material composition of the sample material on the surface of the substrate depicted in FIG. 10.

Consistent with the improved crystallization afforded by the matrix re-dissolving method, mass spectrum acquisition appeared more reproducible than with pre-mixed matrix plus analyte solutions; each of the 100 five fmol spots of the 23-mer yielded interpreted mass spectra (FIG. 11), with 99/100 parent ion signals having signal to noise ratios of >5; such reproducibility was also obtained with the flat silicon and metallic surfaces tried (not shown). The FIG. 11 spectra were obtained on a linear TOF instrument operated at 26 kV. Upon internal calibration of the top left spectrum (well 'k1') using the singly and doubly charged molecular ions, and application of this calibration file to all other 99 spectra as an external calibration (FIG. 12), a standard deviation of <9 Da from the average molecular weight was obtained, corresponding to a relative standard deviation of ~0.1%.

Parallel Dispensing with the Robotic Pintool

Arrays were made with offset printing as described above. The velocity of the X and Y stages are 35 inches/sec, and the velocity of the Z stage is 5.5 inches/sec. It is possible to move the X and Y stages at maximum velocity to decrease the cycle times, however the speed of the Z stage is to be decreased prior to surface contact with the wafer to avoid damaging it. At such axes speeds, the approximate cycle time to spot 16 elements (one tool impression of the same solutions) on all ten wafers is 20 seconds, so to make an array of 256 elements would take ~5.3 minutes. When placing different oligonucleotide solutions on the array, an additional washing step much be incorporated to clean the pin tip prior to dipping in another solution, thus the cycle time would increase to 25 seconds or 6.7 minutes to make 10 wafers.

Sample delivery by the tool was examined using radio-labeled solutions and the phosphorimager as described previously; it was determined that each pin delivers approximately 1 nL of liquid. The spot-to-spot reproducibility is high. An array of 256 oligonucleotide elements of varying sequence and concentration was made on flat silicon wafers using the pintool, and the wafer was analyzed by MALDI-TOF MS.

EXAMPLE 3

Use of High Density Nucleic Acid Immobilization to Generate Nucleic Acid Arrays

Employing the high density attachment procedure described in EXAMPLE 1, an array of DNA oligomers amenable to MALDI-TOF mass spectrometry analysis was created on a silicon wafer having a plurality of locations, e.g., depressions or patches, on its surface. To generate the array, a free thiol-containing oligonucleotide primer was immobilized only at the selected locations of the wafer (e.g., see FIG. 13). Each location of the array contained one of three different oligomers. To demonstrate that the different immobilized oligomers could be separately detected and distinguished, three distinct oligonucleotides of differing lengths that are complementary to one of the three oligomers were hybridized to the array on the wafer and analyzed by MALDI-TOF mass spectrometry.

Oligodeoxynucleotides

Three sets of complementary oligodeoxynucleotide pairs were synthesized in which one member of the complementary oligonucleotide pair contains a 3'- or 5'-disulfide linkage (purchased from Operon Technologies or Oligos, Etc.). For example, Oligomer 1 (d(CTGATGCGTCGGATCATCTTTTTT-SS); SEQ ID NO: 5) contains a 3'-disulfide linkage whereas Oligomer 2 (d(SS-CCTCTTGGGAACTGTGTAGTATT); a 5'-disulfide derivative of SEQ ID NO: 6) and Oligomer 3 (d(SS-GAATTCGAGCTCGGTACCCGG); a 5'-disulfide derivative of SEQ ID NO: 1) each contain a 5'-disulfide linkage.

The oligonucleotides complementary to Oligomers 1–3 were designed to be of different lengths that are easily resolvable from one another during MALDI-TOF MS analysis. For example, a 23-mer oligonucleotide (SEQ ID NO: 7) was synthesized complementary to a portion of Oligomer 1, a 12-mer oligonucleotide (SEQ ID NO: 8) was synthesized complementary to a portion of Oligomer 2 and a 21-mer (SEQ ID NO: 2; sequence denoted "MJM6" in EXAMPLE 1) was synthesized complementary to a portion of Oligomer 3. In addition, a fourth 29-mer oligonucleotide (SEQ ID NO: 9) was synthesized that lacks complementarity to any of the three oligomers. This fourth oligonucleotide was used as a negative control.

Silicon Surface Chemistry and DNA Immobilization (a) 4×4 (16-location) array

A 2×2 $cm^2$ silicon wafer having 256 individual depressions or wells in the form of a 16×16 well array was purchased from a commercial supplier (Accelerator Technology Corp., College Station, Tex.). The wells were 800× 800 $μm^2$, 120 μm deep, on a 1.125 pitch. The silicon wafer was reacted with 3-aminopropyltriethoxysilane to produce a uniform layer of primary amines on the surface and then exposed to the heterobifunctional crosslinker SIAB resulting in iodoacetamido functionalities on the surface (e.g., see FIG. 7).

To prepare the oligomers for coupling to the various locations of the silicon array, the disulfide bond of each oligomer was fully reduced using 10 mM TCEP as depicted in EXAMPLE 1, and the DNA resuspended at a final concentration of 10 μM in a solution of 100 mM phosphate buffer, pH 8.0. Immediately following disulfide bond reduction, the free-thiol group of the oligomer was coupled to the iodoacetamido functionality at 16 locations on the wafer using the probe coupling conditions essentially as described in FIG. 7. To accomplish the separate coupling at 16 distinct locations of the wafer, the entire surface of the wafer was not flushed with an oligonucleotide solution but, instead, an ~30-nl aliquot of a predetermined modified oligomer was added in parallel to each of 16 locations (i.e., depressions) of the 256 wells on the wafer to create a 4×4 array of immobilied DNA using a pin tool as described herein (see e.g., the Detailed Description and Example 4 provided herein).

Figure 13:
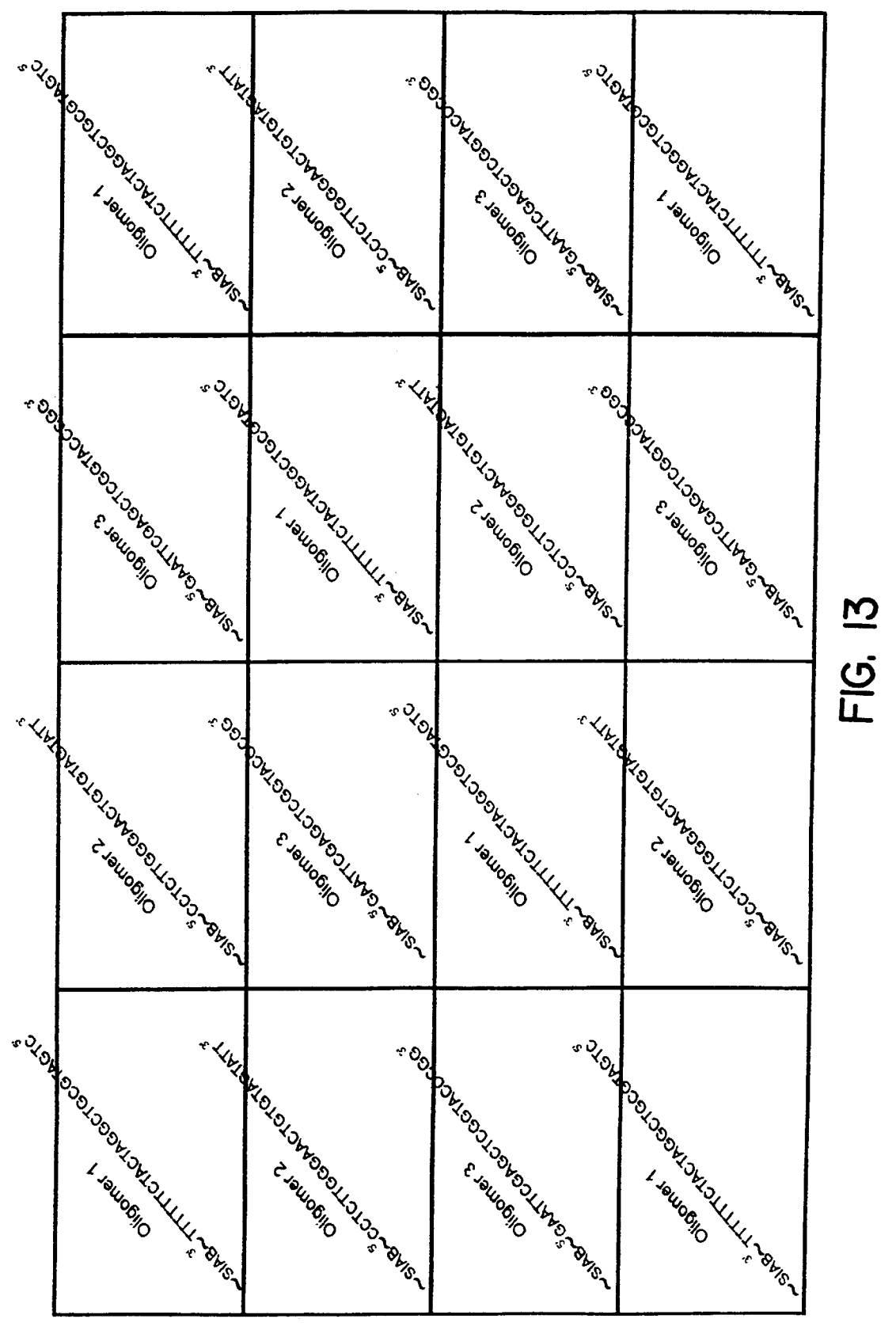

Thus, as shown in FIG. 13, one of modified Oligomers 1–3 was covalently immobilized to each of 16 separate wells of the 256 wells on the silicon wafer thereby creating a 4×4 array of immobilized DNA. For example, Oligomer 1 was conjugated at a well position in the upper left hand corner of the 4×4 array and Oligomer 2 was conjugated to the adjacent location, and so forth. An illustration of the completed array is shown in FIG. 13.

Figure 14:
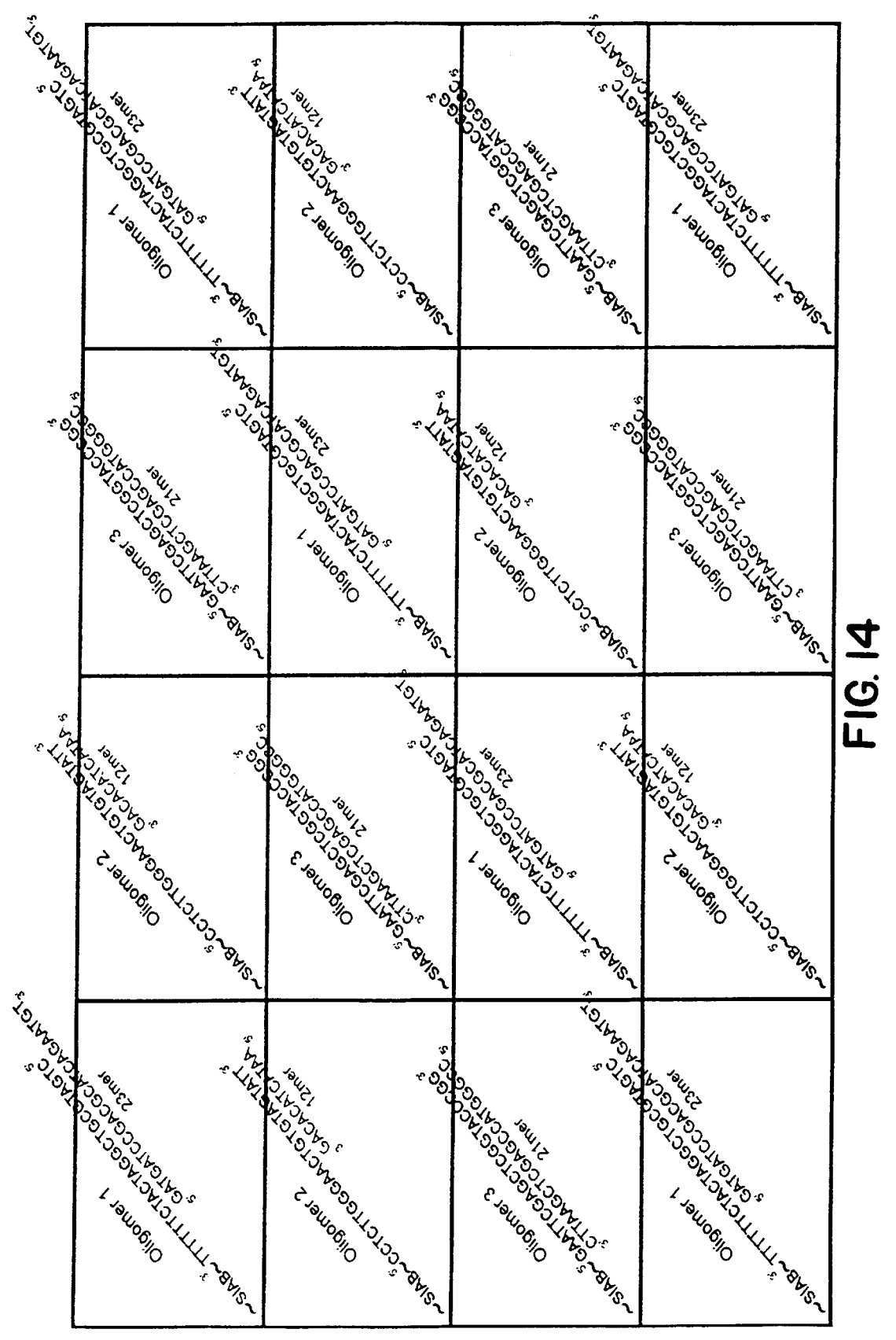

In carrying out the hybridization reaction, the three complementary oligonucleotides and the negative control oligonucleotide were mixed at a final concentration of 10 µM for each oligonucleotide in 1 ml of TE buffer (10 mM Tris-HCl, pH 8.0, 1 mM EDTA) supplemented with 1 M NaCl, and the solution was heated at 65° C. for 10 min. Immediately thereafter, the entire surface of the silicon wafer was flushed with 800 µl of the heated oligonucleotide solution. The complementary oligonucleotides were annealed to the immobilized oligomers by incubating the silicon array at ambient temperature for 1 hr, followed by incubation at 4° C. for at least 10 min. Alternatively, the oligonucleotide solution can be added to the wafer which is then heated and allowed to cool for hybridization. An illustration of the complementary oligonucleotides annealed to the specific oligomers covalently immobilized at each location is shown in FIG. 14.

The hybridized array was then washed with a solution of 50 mM ammonium citrate buffer for cation exchange to remove sodium and potassium ions on the DNA backbone (Pieles, U. et al., (1993) *Nucl. Acids Res.*, 21:3191–3196). A 6-nl aliquot of a matrix solution of 3-hydroxypicolinic acid (0.7 M 3-hydroxypicolinic acid-10% ammonium citrate in 50% acetonitrile; see Wu et al., *Rapid Commun. Mass Spectrom.* 7:142–146 (1993)) was added to each location of the array using a piezoelectric pipette as described herein.

The solution was allowed to dry at ambient temperature and thereafter a 6-nl aliquot of water was added to each location using a piezoelectric pipette to resuspend the dried matrix-DNA complex, such that upon drying at ambient temperature the matrix-DNA complex forms a uniform crystalline surface on the bottom surface of each location.

MALDI-TOF MS Analysis

Figure 15:
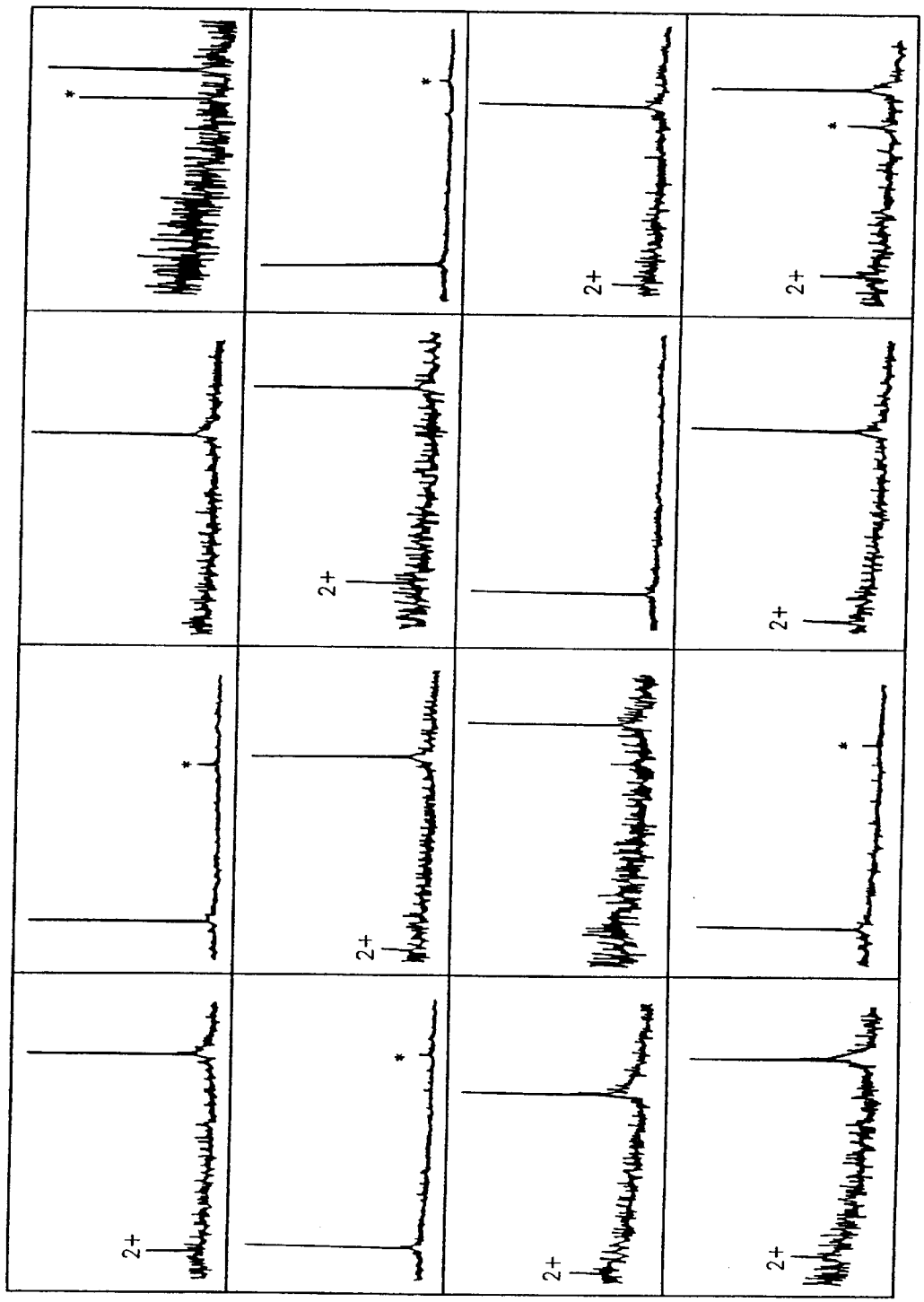
FIG. 15 is a representative MALDI-TOF mass spectrum of a 4×4 (16-location) DNA array on a silicon wafer shown schematically in FIG. 15. The spectrum reveals a single, predominant signal of an experimental mass-to-charge ratio in each location corresponding to the specific hybridized oligonucleotides. The 2+ indicates the position of a doubly charged molecule used as a reference standard during MALDI-TOF MS analysis. The * denotes residual amounts of contaminating oligonucleotide that remain on the surface of the chip following washing procedures. The relative position of the * signal reveals the approximate size of the contaminating oligonucleotide.

The MALDI-TOF MS analysis was performed in series on each of the 16 locations of the hybridization array illustrated in FIG. 14 essentially as described in EXAMPLE 1. The resulting mass spectrum of oligonucleotides that specifically hybridized to each of the 16 locations of the DNA hybridization array is shown in FIG. 15. The mass spectrum revealed a specific signal at each location representative of observed experimental mass-to-charge ratio corresponding to the specific complementary nucleotide sequence.

For example, in the locations that have only Oligomer 1 conjugated thereto, the mass spectrum revealed a predominate signal with an observed experimental mass-to-charge ratio of 7072.4 approximately equal to that of the 23-mer; the theoretical mass-to-charge ratio of the 23-mer is 7072.6 Da. Similarly, specific hybridization of the 1 2-mer oligonucleotide to the array, observed experimental mass-to-charge ratio of 3618.33 Da (theoretical 3622.4 Da), was detected only at those locations conjugated with Oligomer 2 whereas specific hybridization of MJM6 (observed experimental mass-to-charge ratio of 6415.4) was detected only at those locations of the array conjugated with Oligomer 3 (theoretical 6407.2 Da).

None of the locations of the array revealed a signal that corresponds to the negative control 29-mer oligonucleotide (theoretical mass-to-charge ratio of 8974.8) indicating that specific target DNA molecules can be hybridized to oligomers covalently immobilized to specific locations on the surface of the silicon array and a plurality of hybridization assays may be individually monitored using MALDI-TOF MS analysis.

(b) 8×8 (64location) array

A 2×2 $cm^2$ silicon wafer having 256 individual depressions or wells that form a 16×16 array of wells was purchased from a commercial supplier (Accelerator Technology Corp., College Station, Tex.). The wells were 800×800 $m^2$, 120 µm deep, on a 1.125 pitch. The silicon wafer was reacted with 3-aminopropyltriethoxysilane to produce a uniform layer of primary amines on the surface and then exposed to the heterobifunctional crosslinker SIAB resulting in iodoacetamido functionalities on the surface (e.g., see FIG. 7).

Figure 16:
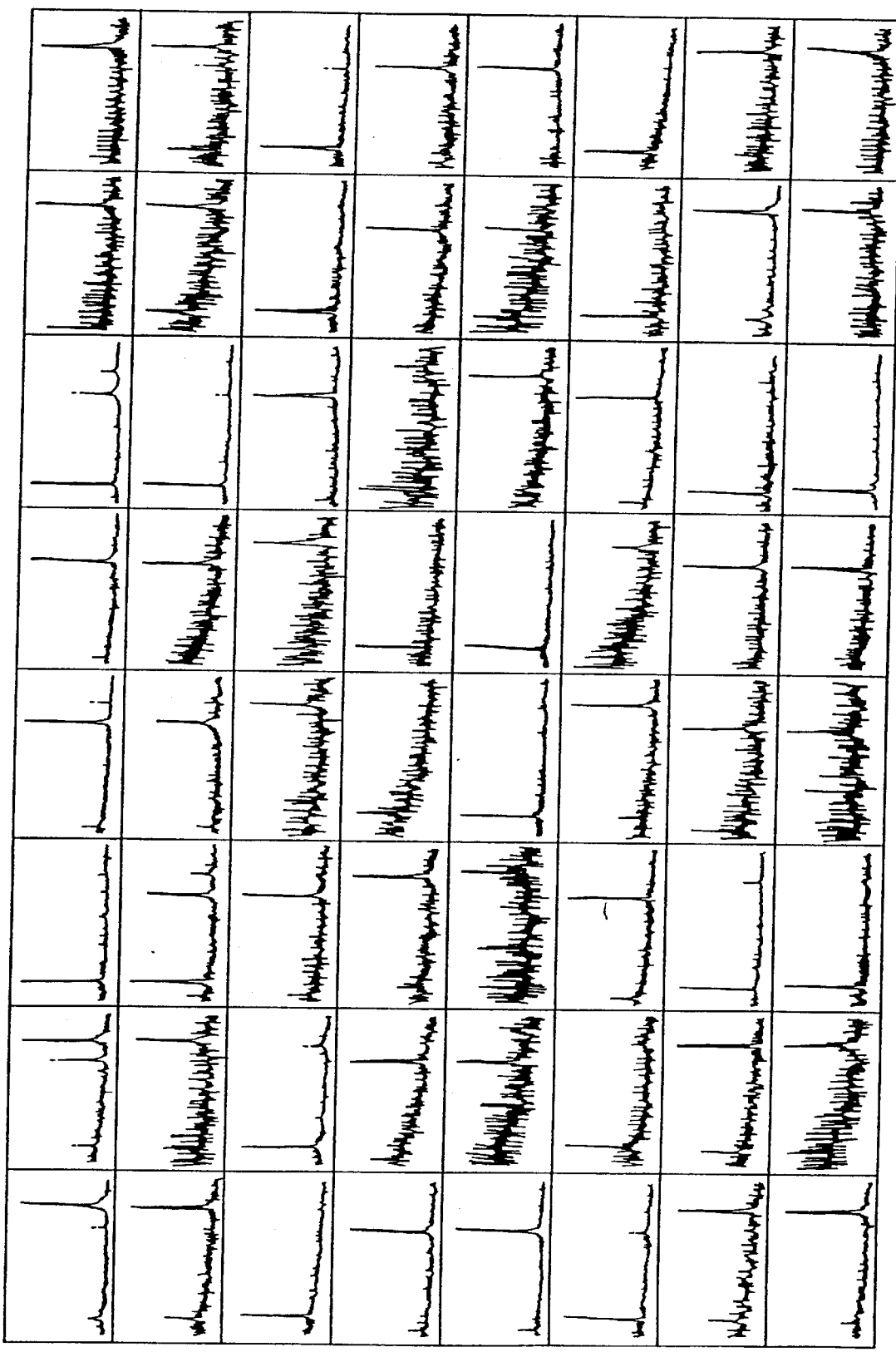
FIG. 16 is a representative MALDI-TOF mass spectrum of an 8×8 (64-location) DNA array. The spectrum reveals a single, predominant signal of an experimental mass-to-charge ratio corresponding to the predicted specific hybridized oligonucleotides. The * denotes residual amounts of contaminating oligonucleotide that remain on the surface of the wafer following washing procedures. The relative position of the * signal reveals the approximate size of the contaminating oligonucleotide.

Following the procedures described above for the preparation of the 16-location DNA array, Oligomers 1–3 were immobilized to 64 locations forming an 8×8 array on the 256 well silicon wafer, hybridized to complementary oligonucleotides and analyzed by MALDI-TOF MS analysis. FIG. 16 shows the mass spectrum of the 64-location DNA array analyzed in series by MALDI-TOF analysis. As shown for the 16-location array, specific hybridization of the complementary oligonucleotide to each of the immobilized thiol-containing oligomers was observed in each of the locations of the DNA array.

EXAMPLE 4

RNA Transcription of One-strand Nicked DNA Template

1. Design of Template and Primer Sequences

Figure 17:
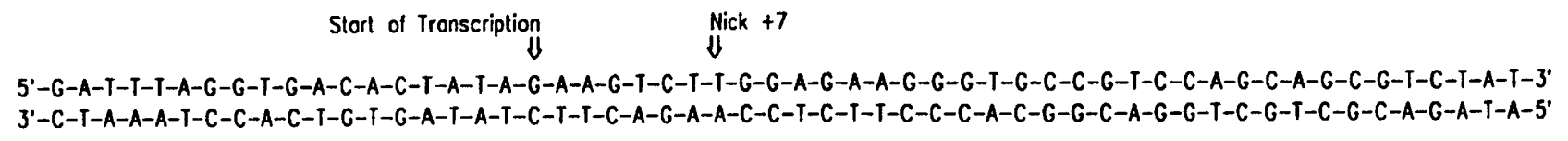

All primers were synthesized on a commercially available DNA Synthesizer using conventional phosphoroamidite chemistry (Sinha et al. (1984) *Nucleic Acid Res.* 12:4539). In vitro RNA transcription was performed on a synthetic 55 nucleotide double stranded DNA template. The template was assembled using three primer sequences; a 55 nucleotide noncoding strand (SEQ ID No: 10) and two additional primers which form the coding strand (SEQ ID Nos: 11 & 12). As shown in FIG. 17, the specific position of the nick in the coding strand at a defined by the length of the each of the coding stand primers.

2. Primer Hybridization and RNA Transcription

One strand nicked templates were produced the hybridization of the three single stranded oligonucleotides at a total DNA concentration of 10 µM (2 fold excess of primers over template) in 10 mM $MgCl_2$ by heating the reaction mixture at 70° C. for 10 minutes and cooling to room temperature for at least 4 hours. The position of the nick is determined by the corresponding lengths of the two coding strand (5'-3') DNA oligonucleotides.

In vitro transcription of the nicked DNA template was carried out in 20 µl reactions of 40 mM Tris-HCl (pH 7.0), 6 mM $MgCl_2$, 2 mM spermidine, 10 mM NaCl, 10 mM dithiothreitol, 1 unit/µl RNasin (Promega), 5 mM rNTP, 5 µCi (α-32P) rCTP, 1 unit/µl SP6 RNA polymerase (Amersham, Arlington Heights, Ill.) at 37° C. for 30 minutes. Abortive and full length RNA transcripts were separated by gel electrophoresis and quantified by measuring the radioactivity of individual RNA fragments by drying the polyacrylimide gel and measuring the radioactivity as compared to a known standard using a Phospholmager (Molecular Dynamics, Inc.). The efficiency of full-length RNA transcription of a nicked DNA template was calculated as a percentage the moles of full length RNA transcribed from a DNA template containing no nicks. The nick by pass efficiency of a nicked DNA template was calculated as a percentage of the moles full-length RNA transcript and the moles of RNA transcript stalled at the nick.

As illustrated in Table 1, the transcription of a full length RNA proceeds with 88–94% efficiency when a nick is introduced into the coding strand after nucleotides +7, +8, +9 or +19 relative to the start of transcription.

TABLE 1

| | 6-mer RNA (%) | Nick-stalled RNA (%) | Full-Length RNA (%) | Nick-Bypass Efficiency (%) |
|---|---|---|---|---|
| Ref. | 320 ± 93 | — | (100) | 100 ± 0 |
| 1N + 7U | 193.2 ± 46.3 | 12.45.4 | 95.8 ± 6.5 | 88.5 ± 5.1 |
| 1N + 8U | 187.4 ± 39.9 | 5.3 ± 4.2 | 87.1 ± 4.3 | 94.3 ± 0.5 |
| 1N + 9U | 232.7 ± 45.6 | 10.1 ± 1.1 | 65.7 ± 4.4 | 87.6 ± 1.8 |
| 1N + 19U | 279.6 ± 33.8 | 6.6 ± 0.3 | 64.8 ± 4.5 | 90.9 ± 0.4 |

EXAMPLE 5

DNA Sequencing Using T7 RNA Polymerase

1. Design of Template and Primer Sequences

All primers were synthesized on a commercially available DNA Synthesizer using conventional phosphoroamidite chemistry (Sinha et al. (1984) *Nucleic Acid Res.* 12:4539). In vitro RNA transcription was performed on a synthetic 276 nucleotide double stranded DNA template (SEQ ID No. 13).

2. DNA Sequencing

DNA sequencing of a target DNA template was carried out in 10 $\mu$l reactions of 40 mM Tris-HCl (pH 7.9), 6 mM $MgCl_2$, 2 mM neutralized spermidine, 5 mM dithiothreitol, 300 nM rCTP, 300 nM rATP, 300 nM rUTP, 300 nM rITP, 600 nM rGMP, 10 $\mu$Ci ($\alpha$-$^{32}$P) rCTP or UTP, 10–50 $\mu$M 3'-deoxynucleotide, 0.5–1.0 pmole linearized or supercoiled DNA emplate, 4 units RNasin (Promega), 10 unit/$\mu$l T7 RNA polymerase (USB) at 37° C. for 30 minutes. Chain termination fragments RNA transcripts were separated by gel electrophoresis using 8% or 13% polyacrylamide gel.

DNA sequencing ladders of RNA terminated fragment were generated up to 180–200 bases. This example shows that T7 RNA polymerase can specifically incorporate modified 3'-deoxyribonucleosides triphosphates as a base-specific chain terminator to generate nested RNA transcripts for sequencing nucleic acids.

We claim:

1. A method for determining the sequence of a target nucleic acid molecule, comprising:
   a) immobilizing a nucleic acid promoter-containing probe on a solid support, wherein:
      the nucleic acid promoter-containing probe comprises at least 5 nucleotides at the 3'-end of the coding strand that is complementary to a single stranded region at the 3'-end of the target nucleic acid, and a double-stranded portion that comprises the promoter, which is oriented to permit transcription of a hybridized target nucleic acid molecule;
   b) hybridizing the target nucleic acid to the single-stranded portion of the immobilized nucleic acid probe;
   c) transcribing the target nucleic acid with an RNA polymerase to produce a plurality of base-specifically terminated RNA transcripts, wherein the RNA polymerase recognizes the promoter;
   d) determining the molecular weight value of each base-specifically terminated RNA transcript by mass spectrometry; and
   e) determining the sequence of the nucleic acid by aligning the base-specifically terminated RNA transcripts according to molecular weight.

2. The method of claim 1, wherein at least two base-specifically terminated RNA transcripts are produced.

3. The method of claim 1, wherein the immobilized nucleic acid promoter-containing probe is produced by immobilizing a single-stranded molecule that comprises a promoter or the complement of a promoter and hybridizing a fragment that comprises the complement thereof, whereby the resulting double-stranded region comprises a promoter.

4. The method of claim 1, further comprising between steps b) and c):
   adding a ligase to form a phosphodiester bond between the 3' hydroxyl group and the 5' phosphate group of adjacent strands of the nucleic acid probe and the target nucleic acid.

5. The method of claim 1, wherein the promoter is selected from the group consisting of archaebacteria, eubacteria, bacteriophages, DNA viruses, RNA viruses, plants, plant viruses and eukaryotic promoters.

6. The method of claim 1, wherein the RNA polymerase is a DNA-dependent RNA polymerase.

7. The method of claim 1, wherein the RNA polymerase is an RNA-dependent RNA polymerase.

8. The method of claim 1, wherein the RNA polymerase is selected from the group consisting of archaebacteria, eubacteria, bacteriophages, DNA viruses, RNA viruses, plants and eukaryotic RNA polymerases.

9. The method of claim 1, wherein the RNA polymerase is selected from the group consisting of *Escherichia coli* RNA polymerase, T7 RNA polymerase, SP6 RNA polymerase, T3 RNA polymerase and Qβ replicase.

10. The method of claim 1, wherein prior to immobilization of the nucleic acid, the surface of the support is derivatized by reacting the surface with an aminosilane to produce primary amines on the surface of the support.

11. The method of claim 10, wherein the aminosilane is 3-amino-propyltriethoxysilane.

12. The method of claim 10, further comprising reacting the primary amines on the surface of the support with a thiol-reactive cross-linking reagent to form a thiol-reactive solid support.

13. The method of claim 12, wherein the thiol-reactive cross-linking reagent is N-succinimidyl (4-iodoacetyl) aminobenzoate (SIAB).

14. The method of claim 12, wherein the immobilization of the nucleic acid probe to a solid support is effected by reacting the thiol-reactive solid support with a nucleic acid probe having a free 5'- or 3'-thiol group, whereby a covalent bond between the thiol group and the thiol-reactive solid support is formed.

15. The method of claim 1, wherein the nucleic acid probe is covalently bound to a surface the solid support at a density of at least 20 fmol/mm$^2$.

16. The method of claim 1, wherein the nucleic acids are immobilized on the surface of the solid support in the form of an array.

17. The method of claim 1, wherein the solid support is silicon.

18. The method of claim 1, wherein the surface comprises a plurality of wells comprising the immobilized nucleic acid molecule.

19. The method of claim 18, wherein the wells have a rough interior surface.

20. The method of claim 18, wherein the solid support has a rough surface.

21. The method of claim 17, wherein the surface of the wells is etched.

22. The method of claim 1, wherein the mass spectrometry analysis is selected from the group consisting of Matrix Assisted Laser Desorption/Ionization, Time-of-Flight (MALDI-TOF) analysis, Electrospray (ES), Ion Cyclotron Resonance (ICR) and Fourier transform.

23. The method of claim 1, wherein transcription is performed in the presence of one or more 3'-deoxyribonucleotides.

24. The method of claim 1, further comprising:

adding a matrix material to the surface of the support, and determining the molecular weight of the synthesized single-stranded ribonucleic acid using mass spectrometry analysis.

25. The method of claim 1, wherein the hybridization of the nucleic acid to be sequence to the solid support results in the formation of a nick in the coding strand corresponding to positions beyond +6 relative to the start of transcription from the promoter.

26. The method of claim 25, wherein the nick is at position +7, +8, +9or +19.

27. The method of claim 1, wherein transcription is performed in the presence of at least one modified ribonucleoside triphosphate analog, whereby the resulting RNA molecule has decreased secondary structure compared to an RNA molecule produced from unmodified ribonucleotide triphosphates.

28. A method of identifying transcriptional terminator sequences or attenuator sequences in a target nucleic acid molecule, comprising:

a) immobilizing a nucleic acid promoter-containing probe on a solid support, wherein the nucleic acid promoter-containing probe comprises at least 5 nucleotides at the 3'-end of the coding strand that is complementary to a single stranded region at the 3'-end of the target nucleic acid, and a double-stranded portion that comprises the promoter, which is oriented to permit transcription of a hybridized target nucleic acid molecule;

b) hybridizing the target nucleic acid molecule to the immobilized nucleic acid probe;

c) transcribing the target nucleic acid with an RNA polymerase to produce a sequence-terminated RNA transcript, wherein the RNA polymerase recognizes the promoter; and d) determining the molecular weight value of the RNA transcript by mass spectrometry, wherein the observed mass of the RNA is indicative of the presence of a the terminator sequence or attenuator in the target nucleic acid molecule.

29. The method of claim 28 that is a method for identifying an attenuator, wherein the termination occurs prior to a coding sequence.

30. The method of claim 28 that is a method for identifying a terminator, wherein the termination occurs after or at the end of a coding sequence.

31. The method of claim 1, wherein in step c), the transcription is carried out in the presence of a modified ribonucleotide, whereby RNA polymerase turnover rate is increased.

32. The method of claim 31, wherein the modified ribonucleotide is selected from the group consisting of 4-thio UTP, 5-bromo UTP and 5-iodo CTP.

33. The method of claim 28, wherein in step c), the transcription is carried out in the presence of a modified ribonucleotide, whereby the RNA polymerase turnover rate is increased.

34. The method of claim 33, wherein the modified ribonucleotide is selected from the group consisting of 4-thio UTP, 5-bromo UTP and 5-iodo CTP.

* * * * *

UNITED STATES PATENT AND TRADEMARK OFFICE
CERTIFICATE OF CORRECTION

PATENT NO.   : 6,268,131 B1
DATED        : July 31, 2001
INVENTOR(S)  : Kang et al.

It is certified that error appears in the above-identified patent and that said Letters Patent is hereby corrected as shown below:

Title pages,
The following Assignee to be added to Item [73]:
-- Korea Advanced Institute of Science and Technology, Yusong-gu, Taejon (REPUBLIC OF KOREA) --

Item [56], U.S. PATENT DOCUMENTS,

| | | | |
|---|---|---|---|
| 4214159 | 01/22/80 | Hillenkamp et al. | 250/288 |
| 4778993 | 10/18/88 | Waugh | 250/287 |
| 4920264 | 04/24/90 | Becker | 250/282 |
| 5062935 | 11/05/91 | Schlag et al. | 204/157.41 |
| 5202561 | 04/13/93 | Giessmann et al. | 250/281 |
| 5373156 | 12/13/94 | Franzen | 250/288 |
| 5376788 | 12/27/94 | Standing et al. | 250/287 |
| 5510613 | 04/23/96 | Reilly et al. | 250/287 |
| 5625184 | 04/29/97 | Vestal et al. | 250/287 |
| 5627369 | 05/06/97 | Vestal et al. | 250/287 |
| 5760393 | 06/02/98 | Vestal et al. | 250/282 |
| 5777324 | 07/07/98 | Hillenkamp | 250/288 |
| 5777325 | 07/07/98 | Weinberger et al. | 250/287 |
| 5869242 | 02/09/99 | Kamb | 435/6 |

Item [56], FOREIGN PATENT DOCUMENTS,

| | | |
|---|---|---|
| 9507361 | 03/16/95 | PCT |
| 9636986 | 11/21/96 | PCT |
| 9636987 | 11/21/96 | PCT |
| 9820019 | 05/14/98 | PCT |
| 9820020 | 05/14/98 | PCT |

UNITED STATES PATENT AND TRADEMARK OFFICE
CERTIFICATE OF CORRECTION

PATENT NO. : 6,268,131 B1
DATED : July 31, 2001
INVENTOR(S) : Kang et al.

It is certified that error appears in the above-identified patent and that said Letters Patent is hereby corrected as shown below:

Item [56], OTHER PUBLICATIONS,
Braun et al., Detecting CFTR gene mutations by using primer oligo base extension and mass spectrometry, Clinical Chemistry 43:1151-1158 (1997).
Caldwell et al., Mid-infrared matrix assisted laser desorption ionization with a water/glycerol matrix, Applied Surface Science 127-129:242-247 (1998).
Ehring et al., Photochemical versus thermal mechanisms in matrix-assisted laser desorption/ionization probed by back side desorption, Rapid Comm in Mass Spect 10:821-824 (1996).
Fu et al., A DNA sequencing strategy which requires only five bases of known terminal sequence for priming, Paper presented, Genome Mapping and Sequencing, Cold Spring Harbor Laboratory.
Fu et al., Sequencing double-stranded DNA by strand displacement, Nucl Acids Res 25:677-679 (1997).
Gross J. et al., "Investigations of the metastable decay of DNA under ultraviolet matrix-assisted laser desorption/ionization conditions with post-source-decay analysis and hydrogen/deuterium exchange", J Am Soc Mass Spectrom. 9(9):866-78 (1998).
Haglund et al., Matrix-assisted laser-desorption mass spectrometry of DNA using an infrared free-electron laser, SPIE 1854 :117-128.
Ji et al., Two-dimensional electrophoretic analysis of proteins expressed by normal and cancerous human crypts: Application of mass spectrometry to peptide-mass fingerprinting, Electrophoresis 15:391-405 (1994).
Juhasz et al., Applications of delayed extraction matrix-assisted laser desorption ionization time-of-flight mass spectrometry to oligonucleotide analysis, Analy Chem 68:941-946 (1996).
Köster et al., Polymer support oligonucleotide synthesis --XV$^{1,2}$, Tetrahedron 40:102-112 (1984).
Köster et al., Some improvements in the synthesis of DNA of biological interest, Nucl Acids Res 7:39-59 (1980).
Lim, Janghoo et al., "DNA sequencing by base-specific abortion of the bacteriophase transcription", Biochemical Society of ROK Annual Fall Meeting, Abstracts p. 191, Taejon, Korea, 10.15-16 (1998).

UNITED STATES PATENT AND TRADEMARK OFFICE
CERTIFICATE OF CORRECTION

PATENT NO. : 6,268,131 B1
DATED : July 31, 2001
INVENTOR(S) : Kang et al.

It is certified that error appears in the above-identified patent and that said Letters Patent is hereby corrected as shown below:

Monforte and Becker, High-throughput DNA analysis by time-of-flight mass spectrometry, Nature Medicine 3:360-362 (1997).
Montforte *et al.*, Analysis of DNA adducts and mutation in transgenic mice exposed to benzo[a]pyrene, Environmental Molec. Mutagenesis 21 Supp 22:49 (1993).
Mosca *et al.*, Mass spectrometry and DNA analysis, Hemoglobin 17(3):261-268 (1993).
Olejnik *et al.*, "Photocleavable biotin phosphoramidite for 5'-end-labeling, affinity purification and phosphorylation of synthetic oligonucleotides", Nucleic Acids Res. 24:351-366 (1996).
Pomerantz *et al.*, Determination of oligonucleotide composition from mass spectrometrically measured molecular weight, Am. Soc. Mass Spectrom. 4:204-09 (1993).
Prome *et al.*, Use of combined mass spectrometry methods for the characterization of a new variant of human hemoglobin: The double mutant hemoglobin villeparisis beta 77 (EF1), J. American Society for Mass Spect 7(2):163-167 (1996).
Tang *et al.*, Improving mass resolution in MALDI/TOF analysis of DNA.
Thuong and Asseline, Oligonucleotides attached to intercalators, photoreactive and cleavage agents, Oligonucleotides and Analogues: A Practical Approach, Eckstein, edr., Oxford University Press Ch. 12, pp. 283-308 (1991)
Vorm *et al.*, Improved resolution and very high sensitivity in MALDI TOF of matrix surfaces made by fast evaporation, Anal. Chem. 66:3281-3287 (1994).

Column 3,
Line 43, please replace the first "a" with -- an --

Column 5,
Line 50, please replace "particluar" with -- particular --

Column 12,
Line 39, please replace "to" with -- . --

UNITED STATES PATENT AND TRADEMARK OFFICE
CERTIFICATE OF CORRECTION

PATENT NO. : 6,268,131 B1
DATED : July 31, 2001
INVENTOR(S) : Kang et al.

It is certified that error appears in the above-identified patent and that said Letters Patent is hereby corrected as shown below:

Column 15,
Line 13, please replace "08/746,053" with -- 08/746,055 --
Line 29, replace "disposes" with -- dispose --
Line 33, replace "instructions" with -- instruction --
Line 39, after "into", insert -- the --

Column 16,
Line 1, replace "access" with -- axis --
Line 37, after "upper block" insert -- 52 --
Line 62, replace "swagelok" with -- tube fitting (swagelok) --
Line 65, replace "than" with -- that --

Column 17,
Line 18, after "holding", insert -- a --
Lines 37-38, after "suitable", delete "for use with a pin assembly"

Column 18,
Line 3, replace "in" with -- is --

Column 21,
Line 6, please replace "Fig. 5" with -- Fig. 1 --
Line 7, replace "lll" with -- ml --

Column 22,
Line 7, please replace "decsribed" with -- described --

Column 23,
Line 36, please replace "derivatived" with -- derivatized --

Column 31,
Line 36, please replace "reproducibilty" with -- reproducibility --

UNITED STATES PATENT AND TRADEMARK OFFICE
CERTIFICATE OF CORRECTION

PATENT NO. : 6,268,131 B1
DATED : July 31, 2001
INVENTOR(S) : Kang et al.

It is certified that error appears in the above-identified patent and that said Letters Patent is hereby corrected as shown below:

Column 34,
Line 63, please replace "immobilied" with -- immobilized --

Column 38,
Line 15, please replace "emplate" with -- template --

Please delete claims 11 and 21 and replace with the following claims:
-- 11. The method of claim 10, wherein the aminosilane is 3-aminopropyltriethoxysilane. --
-- 21. The method of claim 18, wherein the surface of the wells is etched. --

Signed and Sealed this

Fifth Day of February, 2002

Attest:

Attesting Officer

JAMES E. ROGAN
Director of the United States Patent and Trademark Office

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
      (A) LENGTH: 21 base pairs
      (B) TYPE: nucleic acid
      (C) STRANDEDNESS: single
      (D) TOPOLOGY: unknown (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO: 1:

GAATTCGAGC TCGGTACCCG G           21

(2) INFORMATION FOR SEQ ID NO: 2:

(i) SEQUENCE CHARACTERISTICS:
      (A) LENGTH: 21 base pairs
      (B) TYPE: nucleic acid
      (C) STRANDEDNESS: single
      (D) TOPOLOGY: unknown (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO: 2:

CCGGGTACCG AGCTCGAATT C                                                      21

(2) INFORMATION FOR SEQ ID NO: 3:

(i) SEQUENCE CHARACTERISTICS:
            (A) LENGTH: 12 base pairs
            (B) TYPE: nucleic acid
            (C) STRANDEDNESS: unknown
            (D) TOPOLOGY: unknown (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO: 3:

ATCGATCGAT CG                                                                12

(2) INFORMATION FOR SEQ ID NO: 4:

(i) SEQUENCE CHARACTERISTICS:
            (A) LENGTH: 28 base pairs
            (B) TYPE: nucleic acid
            (C) STRANDEDNESS: single
            (D) TOPOLOGY: unknown (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO: 4:

ATCGATCGAT CGATCGATCG ATCGATCG                                               28

(2) INFORMATION FOR SEQ ID NO: 5:

(i) SEQUENCE CHARACTERISTICS:
            (A) LENGTH: 24 base pairs
            (B) TYPE: nucleic acid
            (C) STRANDEDNESS: single
            (D) TOPOLOGY: unknown (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO: 5:

CTGATGCGTC GGATCATCTT TTTT                                                   24

(2) INFORMATION FOR SEQ ID NO: 6:

(i) SEQUENCE CHARACTERISTICS:
    (A) LENGTH: 23 base pairs
    (B) TYPE: nucleic acid
    (C) STRANDEDNESS: unknown
    (D) TOPOLOGY: unknown (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO: 6:

CCTCTTGGGA ACTGTGTAGT ATT                                              23

(2) INFORMATION FOR SEQ ID NO: 7:

(i) SEQUENCE CHARACTERISTICS:
        (A) LENGTH: 23 base pairs
        (B) TYPE: nucleic acid
        (C) STRANDEDNESS: single
        (D) TOPOLOGY: unknown (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO: 7:

GATGATCCGA CGCATCAGAA TGT                                              23

(2) INFORMATION FOR SEQ ID NO: 8:

(i) SEQUENCE CHARACTERISTICS:
        (A) LENGTH: 12 base pairs
        (B) TYPE: nucleic acid
        (C) STRANDEDNESS: single
        (D) TOPOLOGY: unknown (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO: 8:

AATACTACAC AG                                                          12

(2) INFORMATION FOR SEQ ID NO: 9:

(i) SEQUENCE CHARACTERISTICS:
        (A) LENGTH: 29 base pairs
        (B) TYPE: nucleic acid
        (C) STRANDEDNESS: unknown
        (D) TOPOLOGY: unknown (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO: 9:

GATCTAGCTG GGCCGAGCTA GGCCGTTGA                                             29

(2) INFORMATION FOR SEQ ID NO: 10:

(i) SEQUENCE CHARACTERISTICS:
             (A) LENGTH: 55 base pairs
             (B) TYPE: nucleic acid
             (C) STRANDEDNESS: single
             (D) TOPOLOGY: unknown (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO: 10:

ATAGACGCTG CTGGACGGCA CCCTTCTCCA AGACTTCTAT AGTGTCACCT AAATC               55

(2) INFORMATION FOR SEQ ID NO: 11:

(i) SEQUENCE CHARACTERISTICS:
             (A) LENGTH: 25 base pairs
             (B) TYPE: nucleic acid
             (C) STRANDEDNESS: single
             (D) TOPOLOGY: unknown (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO: 11:

GATTTAGGTG ACACTATAGA AGTCT                                                25

(2) INFORMATION FOR SEQ ID NO: 12:

(i) SEQUENCE CHARACTERISTICS:
             (A) LENGTH: 30 base pairs
             (B) TYPE: nucleic acid
             (C) STRANDEDNESS: unknown
             (D) TOPOLOGY: unknown (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO: 12:

TGGAGAAGGG TGCCGTCCAG CAGCGTCTAT                                            30

(2) INFORMATION FOR SEQ ID NO: 13:

(i) SEQUENCE CHARACTERISTICS:
        (A) LENGTH: 276 base pairs
        (B) TYPE: nucleic acid
        (C) STRANDEDNESS: single
        (D) TOPOLOGY: unknown (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO: 13:

```
GCTCTAATAC GACTCACTAT AGGGAGACAA GCTTGCATGC CTGCAGGTCG ACTCTAGAGG      60

ATCCCCGGGT ACCGAGCTCG AATTCCTGGC AGTTTATGGC GGGCGTCTGC CACCCTCCGG     120

GCCGTTGCTT CGCAACGTTC AAATCCGCGT CCGGCGGATT TGTCCTACTC AGGAGAGCGT     180

TCACCCGACA AACAACAGAT AAAAAAAAAG CCCAGTCTTT CGACTGGGCC TTTCGTTTTA     240

TTTGATGCCT GGGAATTCGT ATTCTATTCT ATAGTG                               276
```